United States Patent
Kim et al.

(10) Patent No.: US 9,698,356 B2
(45) Date of Patent: Jul. 4, 2017

(54) HETEROARYL-BASED COMPOUND AND ORGANIC LIGHT-EMITTING DIODE INCLUDING THE SAME

(71) Applicant: Samsung Display Co., Ltd., Yongin, Gyeonggi-Do (KR)

(72) Inventors: Seul-Ong Kim, Yongin (KR); Dong-Woo Shin, Yongin (KR); O-Hyun Kwon, Yongin (KR); Kyul Han, Yongin (KR)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 571 days.

(21) Appl. No.: 13/947,922

(22) Filed: Jul. 22, 2013

(65) Prior Publication Data
US 2014/0306186 A1    Oct. 16, 2014

(30) Foreign Application Priority Data
Apr. 10, 2013  (KR) .................. 10-2013-0039518

(51) Int. Cl.
| | | |
|---|---|---|
| H01L 51/00 | (2006.01) | |
| C07D 401/14 | (2006.01) | |
| C07D 221/18 | (2006.01) | |
| C07D 401/04 | (2006.01) | |
| C07D 403/04 | (2006.01) | |
| C07D 403/10 | (2006.01) | |
| C07D 409/04 | (2006.01) | |
| C07D 241/38 | (2006.01) | |
| C09K 11/06 | (2006.01) | |
| H01L 51/50 | (2006.01) | |

(52) U.S. Cl.
CPC ........ *H01L 51/0072* (2013.01); *C07D 221/18* (2013.01); *C07D 241/38* (2013.01); *C07D 401/04* (2013.01); *C07D 401/14* (2013.01); *C07D 403/04* (2013.01); *C07D 403/10* (2013.01); *C07D 409/04* (2013.01); *C09K 11/06* (2013.01); *H01L 51/0061* (2013.01); *H01L 51/006* (2013.01); *H01L 51/0058* (2013.01); *H01L 51/5012* (2013.01)

(58) Field of Classification Search
None
See application file for complete search history.

(56) References Cited

U.S. PATENT DOCUMENTS

| | | | |
|---|---|---|---|
| 8,088,901 B2 | 1/2012 | Morishita et al. | |
| 2007/0237982 A1 | 10/2007 | Inoue et al. | |
| 2011/0114930 A1 | 5/2011 | Kim et al. | |
| 2011/0272684 A1 | 11/2011 | Parham et al. | |

FOREIGN PATENT DOCUMENTS

| | | | |
|---|---|---|---|
| KR | 10-2007-0035518 A | 3/2007 | |
| KR | 10-2010-0006071 A | 1/2010 | |
| KR | 10-2010-0088604 A | 8/2010 | |
| KR | 10-2011-0052947 A | 5/2011 | |
| KR | 10-2011-0122129 A | 11/2011 | |
| WO | WO-2006/065105 A1 * | 6/2006 | ............. C09K 11/06 |

* cited by examiner

*Primary Examiner* — J. L. Yang
(74) *Attorney, Agent, or Firm* — Knobbe Martens Olson & Bear LLP

(57) ABSTRACT

In an aspect, an organic compound and an organic light-emitting diode (OLED) including the same are provided.

21 Claims, 1 Drawing Sheet

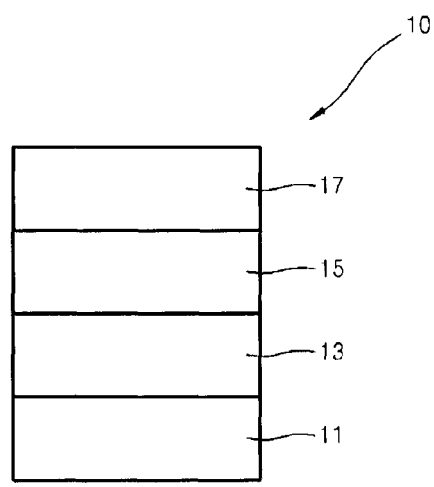

HETEROARYL-BASED COMPOUND AND ORGANIC LIGHT-EMITTING DIODE INCLUDING THE SAME

INCORPORATION BY REFERENCE TO ANY PRIORITY APPLICATIONS

Any and all priority claims identified in the Application Data Sheet, or any correction thereto, are hereby incorporated by reference under 37 CFR 1.57. For example, this application claims the benefit of Korean Patent Application No. 10-2013-0039518, filed on Apr. 10, 2013, in the Korean Intellectual Property Office, the disclosure of which is incorporated herein in its entirety by reference.

BACKGROUND

Field

The present invention relates to a compound of Formula 1 and an organic light-emitting diode including the same.

Description of the Related Technology

Organic light-emitting diodes (OLEDs), which are self-emitting diodes, have advantages such as wide viewing angles, excellent contrast, quick response, high brightness, excellent driving voltage characteristics, and can provide multicolored images.

A typical OLED has a structure including a substrate, and an anode, a hole transport layer, an emission layer, an electron transport layer, and a cathode which are sequentially stacked on the substrate. The hole transport layer, the emission layer, and the electron transport layer may be organic thin films formed of organic compounds.

An operating principle of an OLED having such a structure is as follows.

When a voltage is applied between the anode and the cathode, holes injected from the anode move to the emission layer via the hole transport layer, and electrons injected from the cathode move to the emission layer via the electron transport layer. The holes and electrons, which are carriers, are recombined in the emission layer to generate excitons. When the excitons transition from an excited state to a ground state, light is generated.

SUMMARY

Provided is a high-quality organic light-emitting diode (OLED).

According to an embodiment of the present disclosure, a compound represented by Formula 1 is provided:

Formula 1

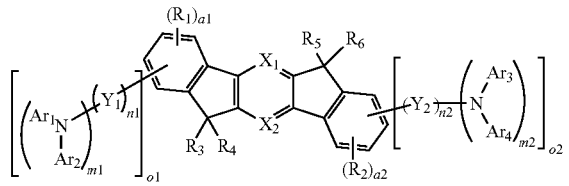

wherein, in Formula 1, $X_1$ may be selected from $C(R_{11})$ and N (nitrogen); $X_2$ is selected from $C(R_{12})$ and N (nitrogen), provided that $X_1$ is $C(R_{11})$ and $X_2$ is $C(R_{12})$ is excluded;

$Y_1$ and $Y_2$ are each independently selected from a substituted or unsubstituted $C_6$-$C_{30}$ arylene group and a substituted or unsubstituted $C_2$-$C_{30}$ heteroarylene group;

n1 and n2 are each independently an integer of 0 to 5, and when n1 is an integer of 2 or more, a plurality of $Y_1$ may be identical to or different from each other, and when n2 is an integer of 2 or more, a plurality of $Y_2$ may be identical to or different from each other;

$Ar_1$ to $Ar_4$ are each independently selected from a substituted or unsubstituted $C_6$-$C_{30}$ aryl group and a substituted or unsubstituted $C_2$-$C_{30}$ heteroaryl group;

$R_{11}$, $R_{12}$ and $R_1$ to $R_6$ are each independently selected from a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a substituted or unsubstituted $C_1$-$C_{30}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$heterocyclo alkyl group, a substituted or unsubstituted $C_3$-$C_{10}$ cycloalkenyl group, a substituted or unsubstituted $C_2$-$C_{10}$heterocycloalkenyl group, a substituted or unsubstituted $C_6$-$C_{30}$ aryl group, and a substituted or unsubstituted $C_2$-$C_{30}$ heteroaryl group;

m1 and m2 are each independently an integer of 1 or 2, and when m1 is 2, two of a moiety represented by

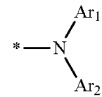

(wherein, * indicates a linking site to $Y_1$) may be identical to or different from each other, and when m2 is 2, two of a moiety represented by

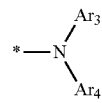

(wherein, * indicates a linking site to $Y_2$) may be identical to or different from each other; o1 and o2 are each independently an integer of 0 to 5, and when o1 is an integer of 2 or more, a plurality of moieties each represented by

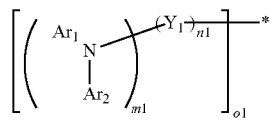

(wherein, * indicates a linking site) may be identical to or different from each other, and when o2 is an integer of 2 or more, a plurality of moieties each represented by

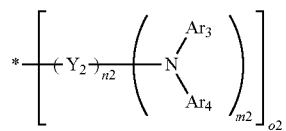

(wherein, * indicates a linking site) may be identical to or different from each other, provided that o1 and o2 are not 0 at the same time;

a1 is an integer of 0 to 4, and when a1 is an integer of 2 or more, a plurality of $R_1$ may be identical to or different from each other; and a2 is an integer of 0 to 4, and when a2 is an integer of 2 or more, a plurality of $R_2$ may be identical to or different from each other.

According to another embodiment of the present disclosure, provided is an organic light-emitting diode (OLED) including: a substrate, a first electrode; a second electrode facing the first electrode; and an organic layer disposed between the first electrode and the second electrode and including an emission layer, wherein the organic layer includes at least one compound represented by Formula 1.

BRIEF DESCRIPTION OF THE DRAWINGS

The above and other features and advantages of the present invention will become more apparent by describing in detail exemplary embodiments thereof with reference to the FIGURE, which is a schematic view of the structure of an organic light-emitting diode (OLED) according to an embodiment of the present invention.

DETAILED DESCRIPTION

As used herein, the term "and/or" includes any and all combinations of one or more of the associated listed items. Expressions such as "at least one of," when preceding a list of elements, modify the entire list of elements and do not modify the individual elements of the list.

Some embodiments provide a compound represented by Formula 1 below:

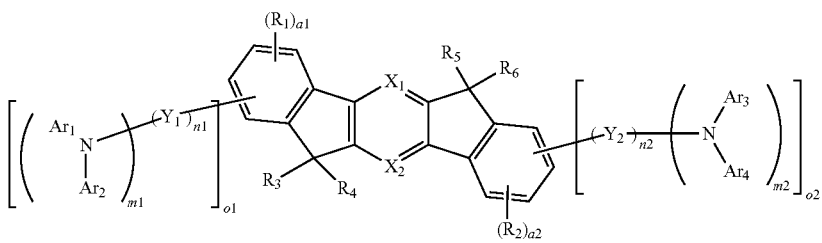

Formula 1 wherein, in Formula 1, $X_1$ is selected from $C(R_{11})$ and N (nitrogen); $X_2$ is selected from $C(R_{12})$ and N (nitrogen); and simultaneously, a case in which $X_1$ is $C(R_{11})$ and $X_2$ is $C(R_{12})$ is excluded.

For example, in Formula 1, $X_1$ is $C(R_{11})$ and $X_2$ is N (nitrogen), but $X_1$ and $X_2$ are not limited thereto.

As another example, in Formula 1, $X_1$ is N (nitrogen) and $X_2$ is $C(R_{12})$, but $X_1$ and $X_2$ are not limited thereto.

As another example, in Formula 1, $X_1$ and $X_2$ may be N (nitrogen) at the same time, but $X_1$ and $X_2$ are not limited thereto.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, and a $C_1$-$C_{10}$ alkyl group; a $C_1$-$C_{10}$ alkyl group substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof; a $C_6$-$C_{16}$ aryl group and a $C_2$-$C_{16}$ heteroaryl group; and a $C_6$-$C_{16}$ aryl group and a $C_2$-$C_{16}$ heteroaryl group, each substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_6$-$C_{16}$ aryl group, and a $C_2$-$C_{16}$ heteroaryl group.

In Formula 1, $Y_1$ and $Y_2$ may be each independently selected from a substituted or unsubstituted $C_6$-$C_{30}$ arylene group and a substituted or unsubstituted $C_2$-$C_{30}$ heteroarylene group.

For example, $Y_1$ and $Y_2$ in Formula 1 may be each independently selected from a substituted or unsubstituted phenylene, a substituted or unsubstituted pentalenylene, a substituted or unsubstituted indenylene, a substituted or unsubstituted naphtylene, a substituted or unsubstituted azulenylene, a substituted or unsubstituted heptalenylene, a substituted or unsubstituted indacenylene, a substituted or unsubstituted acenaphtylene, a substituted or unsubstituted fluorenylene, a substituted or unsubstituted spiro-fluorenylene, a substituted or unsubstituted phenalenylene, a substituted or unsubstituted phenanthrenylene, a substituted or unsubstituted anthrylene, a substituted or unsubstituted fluoranthenylene, a substituted or unsubstituted triphenylenylene, a substituted or unsubstituted pyrenylene, a substituted or unsubstituted chrysenylene, a substituted or unsubstituted naphthacenylene, a substituted or unsubstituted picenylene, a substituted or unsubstituted perylenylene, a substituted or unsubstituted pentaphenylene, a substituted or unsubstituted hexacenylene, a substituted or unsubstituted pyrrolylene, a substituted or unsubstituted imidazolylene, a substituted or unsubstituted pyrazolylene, a substituted or unsubstituted pyridinylene, a substituted or unsubstituted pyrazinylene, a substituted or unsubstituted pyrimidinylene, a substituted or unsubstituted pyridazinylene, a substituted or unsubstituted isoindolylene, a substituted or unsubstituted indolylene, a substituted or unsubstituted indazolylene, a substituted or unsubstituted purinylene, a substituted or unsubstituted quinolinylene, a substituted or unsubstituted benzoquinolinylene, a substituted or unsubstituted phthalazinylene, a substituted or unsubstituted naphthyridinylene, a substituted or unsubstituted quinoxalinylene, a substituted or unsubstituted quinazolinylene, a substituted or unsubstituted cinnolinylene, a substituted or unsubstituted carbazolylene, a substituted or unsubstituted phenanthridinylene, a substituted or unsubstituted acridinylene, a substituted or unsubstituted phenanthrolinylene, a substituted or unsubstituted phenazinylene, a substituted or unsubstituted benzooxazolylene, a substituted or unsubstituted benzoimidazolylene, a substituted or unsubstituted furanylene, a substituted or unsubstituted benzofuranylene, a substituted or unsubstituted thiophenylene, a substituted or unsubstituted benzothiophenylene, a substituted or unsubstituted thienothiophenylene, a substituted or unsubstituted thiazolylene, a substituted or unsubstituted isothiazolylene, a substituted or unsubstituted benzothiazolylene, a substituted or unsubstituted isoxazolylene, a substituted or unsubstituted oxazolylene, a substituted or unsubstituted triazolylene, a substituted or unsubstituted tetrazolylene, a substituted or unsubstituted oxadiazolylene, a substituted or unsubstituted triazinylene, a substituted or unsubstituted benzooxazolylene, a substituted or unsubstituted dibenzopuranylene, a substituted or unsubstituted dibenzothiophenylene, and a substituted or unsubstituted benzocarbazolylene, but are not limited thereto.

As another example, $Y_1$ and $Y_2$ in Formula 1 may be each independently selected from phenylene, naphthylene, anthracenylene, phenanthrenylene, fluorenylene, pyridinylene, pyrazinylene, indolyl, carbazolyl, quinolinylene, thiophenylene, and thienothiophenylene; and phenylene, naphthylene, anthracenylene, phenanthrenylene, fluorenylene, pyridinylene, pyrazinylene, indolyl, carbazolyl, quinolinylene, thiophenylene, and thienothiophenylene, each substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof and a $C_1$-$C_{10}$ alkyl group; a $C_1$-$C_{10}$ alkyl group, each substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof; a $C_6$-$C_{16}$ aryl group and a $C_2$-$C_{16}$ heteroaryl group; and a $C_6$-$C_{16}$ aryl group and a $C_2$-$C_{16}$ heteroaryl group, each substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_6$-$C_{16}$ aryl group, and a $C_2$-$C_{16}$ heteroaryl group, but $Y_1$ and $Y_2$ are not limited thereto.

As another example, $Y_1$ and $Y_2$ in Formula 1 may be each independently selected from phenylene, naphthylene, phenanthrenylene, pyridinylene, indolyl, carbazolyl, quinolinylene, thiophenylene and thienothiophenylene; and phenylene, naphthylene, phenanthrenylene, pyridinylene, indolyl, carbazolyl, quinolinylene, thiophenylene and thienothiophenylene, each selected from at least one of a deuterium atom, a halogen atom, a cyano group, a nitro group, a methyl group, an ethyl group, an n-propyl group, an i-propyl group, an n-butyl group, an i-butyl group, a t-butyl group, a phenyl group, a naphthyl group, an anthryl group, a fluorenyl group, a pyridinyl group, a pyrazinyl group, a pyrimidinyl group, and a pyridazinyl group, but $Y_1$ and $Y_2$ are not limited thereto.

As another example, $Y_1$ and $Y_2$ in Formula 1 may be each independently selected from phenylene, naphthylene, phenanthrenylene, pyridinylene, indolyl, carbazolyl, quinolinylene, thiophenylene, and thienothiophenylene; and phenylene and carbazolyl, each substituted with at least one of a methyl group and a phenyl group, but $Y_1$ and $Y_2$ are not limited thereto.

In Formula 1, n1 refers to the number of $Y_1$ and n2 refers to the number of $Y_2$, n1 and n2 in Formula 1 are each independently an integer of 0 to 5, and when n1 is an integer of 2 or more, a plurality of $Y_1$ may be identical to or different from each other, and when n2 is an integer of 2 or more, a plurality of $Y_2$ may be identical to or different from each other.

For example, n1 and n2 in Formula 1 are each independently an integer of 1 or 2, but n1 and n2 are not limited thereto.

For example, moieties represented by $(Y_1)_{n1}$ and $(Y_2)_{n2}$ in Formula 1 may be each independently one of Formulae 2a to 2q below, but are not limited thereto:

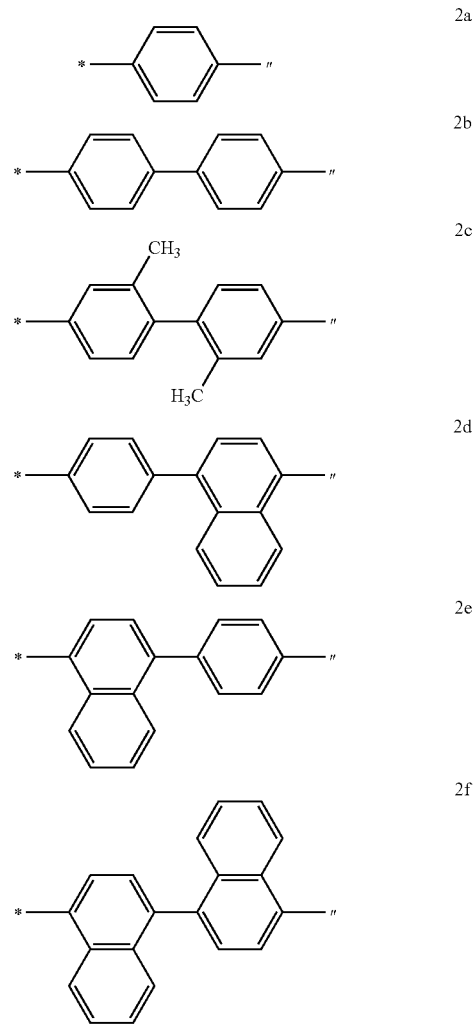

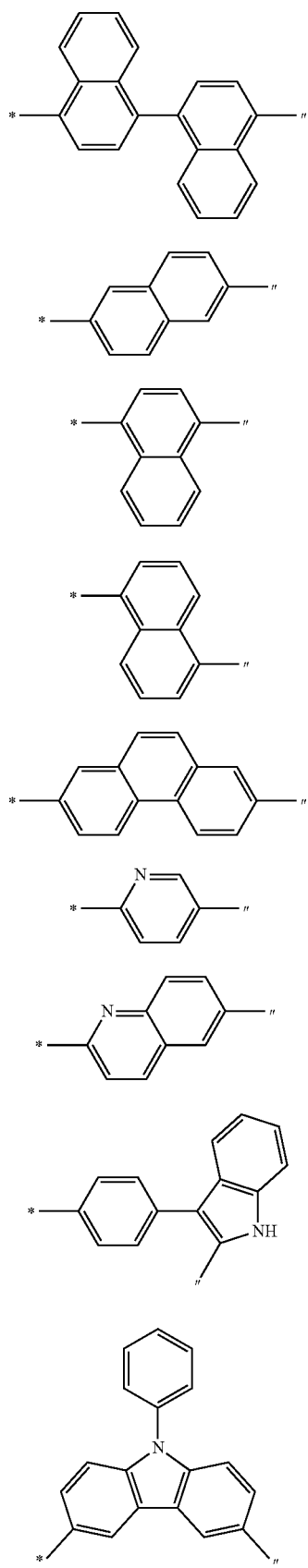

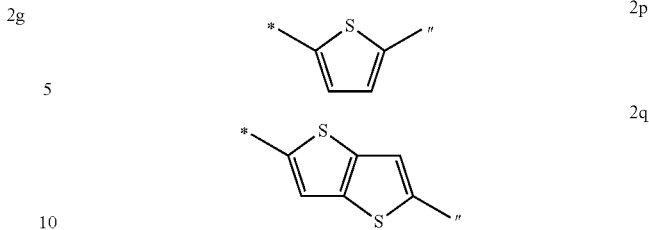

* in Formulae 2a to 2q indicates a binding site to a diindenopyrazin ring or a diindenopyridin ring, and *' indicates a binding site to N (nitrogen).

In some embodiments, $Ar_1$ to $Ar_4$ in Formula 1 may be each independently selected from a substituted or unsubstituted $C_6$-$C_{30}$ aryl group and a substituted or unsubstituted $C_2$-$C_{30}$ heteroaryl group.

For example, $Ar_1$ to $Ar_4$ in Formula 1 may be each independently selected from a substituted or unsubstituted phenyl, a substituted or unsubstituted pentalenyl, a substituted or unsubstituted indenyl, a substituted or unsubstituted a naphtyl, a substituted or unsubstituted azulenyl, a substituted or unsubstituted heptalenyl, a substituted or unsubstituted indacenyl, a substituted or unsubstituted acenaphtyl, a substituted or unsubstituted fluorenyl, a substituted or unsubstituted spiro-fluorenyl group, a substituted or unsubstituted phenalenyl, a substituted or unsubstituted phenanthrenyl, a substituted or unsubstituted anthryl, a substituted or unsubstituted fluoranthenyl, a substituted or unsubstituted triphenylenyl, a substituted or unsubstituted pyrenyl, a substituted or unsubstituted chrysenyl, a substituted or unsubstituted naphthacenyl, a substituted or unsubstituted picenyl, a substituted or unsubstituted perylenyl, a substituted or unsubstituted a pentaphenyl, a substituted or unsubstituted hexacenyl, a substituted or unsubstituted pyrrolyl, a substituted or unsubstituted imidazolyl, a substituted or unsubstituted pyrazolyl, a substituted or unsubstituted pyridinyl, a substituted or unsubstituted pyrazinyl, a substituted or unsubstituted pyrimidinyl, a substituted or unsubstituted pyridazinyl, a substituted or unsubstituted isoindolyl, a substituted or unsubstituted indolyl, a substituted or unsubstituted indazolyl, a substituted or unsubstituted purinyl, a substituted or unsubstituted quinolinyl, a substituted or unsubstituted benzoquinolinyl, a substituted or unsubstituted phthalazinyl, a substituted or unsubstituted naphthyridinyl, a substituted or unsubstituted quinoxalinyl, a substituted or unsubstituted quinazolinyl, a substituted or unsubstituted cinnolinyl, a substituted or unsubstituted carbazolyl, a substituted or unsubstituted phenanthridinyl, a substituted or unsubstituted acridinyl, a substituted or unsubstituted phenanthrolinyl, a substituted or unsubstituted phenazinyl, a substituted or unsubstituted benzoimidazolyl, a substituted or unsubstituted furanyl, a substituted or unsubstituted benzofuranyl, a substituted or unsubstituted thiophenyl, a substituted or unsubstituted benzothiophenyl, a substituted or unsubstituted thiazolyl, a substituted or unsubstituted isothiazolyl, a substituted or unsubstituted benzothiazolyl, a substituted or unsubstituted isoxazolyl, a substituted or unsubstituted oxazolyl, a substituted or unsubstituted triazolyl, a substituted or unsubstituted tetrazolyl, a substituted or unsubstituted oxadiazolyl, a substituted or unsubstituted triazinyl, a substituted or unsubstituted benzooxazolyl, a substituted or unsubstituted dibenzofuranyl, a substituted or unsubstituted dibenzothiophenyl, and a substituted or unsubstituted benzocarbazolyl, but $Ar_1$ to $Ar_4$ are not limited thereto.

In some embodiments, $Ar_1$ to $Ar_4$ in Formula 1 may be each independently selected from a phenyl group, a naphthyl group, an anthryl group, a fluorenyl group, a pyridyl group, a benzofuranyl group, a benzothiophenyl group, a dibenzofuranyl group, and a dibenzothiophenyl group; and a phenyl group, a naphthyl group, an anthryl group, a fluorenyl group, a pyridyl group, a benzofuranyl group, a benzothiophenyl group, a dibenzofuranyl group, and a dibenzothiophenyl group, each substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, and a $C_1$-$C_{10}$ alkyl group; a $C_1$-$C_{10}$ alkyl group substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof; a $C_6$-$C_{16}$ aryl group and a $C_2$-$C_{16}$ heteroaryl group; and a $C_6$-$C_{16}$ aryl group and a $C_2$-$C_{16}$ heteroaryl group, each substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_6$-$C_{16}$ aryl group, and a $C_2$-$C_{16}$ heteroaryl group, but $Ar_1$ to $Ar_4$ are not limited thereto.

In some embodiments, $Ar_1$ to $Ar_4$ in Formula 1 may be each independently selected from a phenyl group, a naphthyl group, a fluorenyl group, a pyridyl group, and a dibenzothiophenyl group; and a phenyl group, a naphthyl group, a fluorenyl group, a pyridyl group, and a dibenzothiophenyl group, each substituted with at least one of a deuterium atom, —F, a cyano group, a nitro group, a methyl group, an ethyl group, an n-propyl group, an i-propyl group, an n-butyl group, a sec-butyl group, an i-butyl group, a t-butyl group, a phenyl group, a naphthyl group, and an anthryl group, but $Ar_1$ to $Ar_4$ are not limited thereto.

In some embodiments, $Ar_1$ to $Ar_4$ in Formula 1 may be each independently one of Formulae 3a to 3k below, but are not limited thereto:

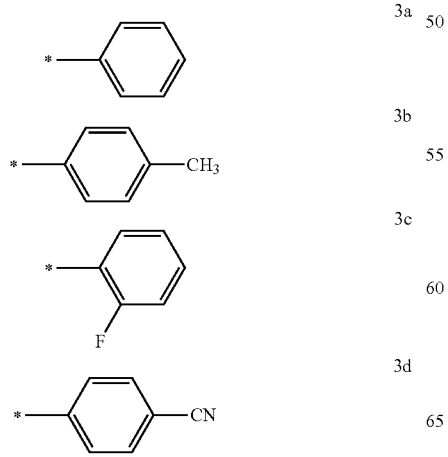

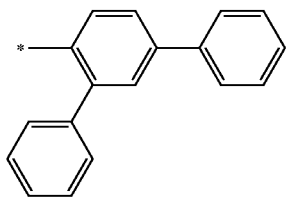

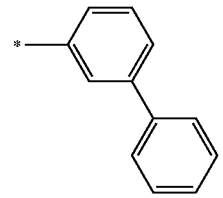

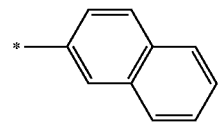

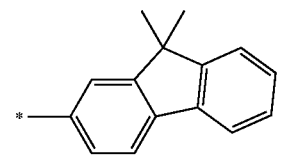

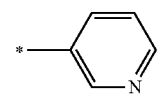

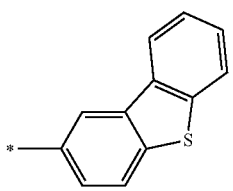

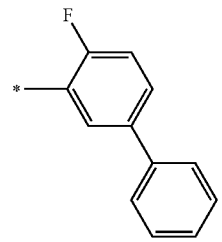

* in Formulae 3a to 3k is a binding site to N (nitrogen).

In some embodiments, $R_{11}$, $R_{12}$ and $R_1$ to $R_6$ in Formula 1 may be each independently selected from a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a substituted or unsubstituted $C_1$-$C_{30}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ hetero cycloalkyl group, a substituted or unsubstituted $C_3$-$C_{10}$ cycloalkenyl group, a substituted or unsubstituted $C_2$-$C_{10}$ hetero cycloalkenyl group, a substituted or unsubstituted $C_6$-$C_{30}$ aryl group, and a substituted or unsubstituted $C_2$-$C_{30}$ heteroaryl group.

In some embodiments, $R_{11}$ and $R_{12}$ in Formula 1 may be each independently selected from a hydrogen atom, a deuterium atom, a halogen atom, a cyano group, and a nitro group; a $C_1$-$C_{10}$ alkyl group substituted with at least one of a hydrogen atom, a deuterium atom, a halogen atom, a cyano group and a nitro group; a $C_6$-$C_{16}$ aryl group, and a $C_2$-$C_{16}$ heteroaryl group; and a $C_6$-$C_{16}$ aryl group and a $C_2$-$C_{16}$ heteroaryl group, each substituted with at least one of a deuterium atom, a halogen atom, a cyano group, a nitro group, and a $C_1$-$C_{60}$ alkyl group, but $R_{11}$ and $R_{12}$ are not limited thereto.

In some embodiments, $R_{11}$ and $R_{12}$ may be each independently selected from a hydrogen atom, a deuterium atom, —F, a cyano group, and a nitro group; a methyl group, an ethyl group, an n-propyl group, an iso-propyl group, an n-butyl group, a sec-butyl group, an iso-butyl group, and a tert-butyl group, each substituted with at least one of a hydrogen atom, a deuterium atom, —F, a cyano group and nitro group; a phenyl group, a naphthyl group, and a pyridyl group; a phenyl group, a naphthyl group and a pyridyl group, each substituted with at least one of a hydrogen atom, a deuterium atom, —F, a cyano group, a nitro group, a methyl group, an ethyl group, an n-propyl group, an iso-propyl group, an n-butyl group, a sec-butyl group, an iso-butyl group, and a tert-butyl group; but $R_{11}$ and $R_{12}$ are not limited thereto.

In some embodiments, $R_{11}$ and $R_{12}$ may be each independently selected from a hydrogen atom and a deuterium atom, but are not limited thereto.

In some embodiments, $R_1$ and $R_2$ in Formula 1 may be each independently selected from a hydrogen atom, a deuterium atom, a halogen atom, a cyano group and a nitro group; a $C_6$-$C_{16}$ aryl group and a $C_2$-$C_{16}$ heteroaryl group; and a $C_6$-$C_{16}$ aryl group and a $C_2$-$C_{16}$ heteroaryl group, each substituted with at least one of a hydrogen atom, a deuterium atom, a halogen atom, a cyano group, a nitro group, a $C_6$-$C_{16}$ aryl group, and a $C_2$-$C_{16}$ heteroaryl group, but are not limited thereto.

In some embodiments, $R_1$ and $R_2$ in Formula 1 may be each independently selected from a hydrogen atom, a deuterium atom, —F, a cyano group and a nitro group; a phenyl group, a naphthyl group, an anthracenyl group, a phenanthrenyl group, a triazinyl group, a carbazole group, a pyridyl group, a quinoline group, an isoquinoline group, a benzothiophenyl group, and a dibenzothiophenyl group; and a phenyl group, a naphthyl group, an anthracenyl group, a phenanthrenyl group, a triazinyl group, a carbazole group, a pyridyl group, a quinoline group, an isoquinoline group, benzothiophenyl group, and a dibenzothiophenyl group, each substituted with at least one of a hydrogen atom, a deuterium atom, —F, a cyano group, nitro group, a phenyl group, a naphthyl group, an anthracenyl group, a pyridyl group, a carbazole group, and a thiophene group, but are not limited thereto.

In some embodiments, $R_1$ and $R_2$ in Formula 1 may be each independently selected from a hydrogen atom and a deuterium atom; and a phenyl group, a naphthyl group, a phenanthrenyl group, a triazinyl group, a carbazole group, an isoquinoline group, and a dibenzothiophenyl group; and a phenyl group, a naphthyl group, a phenanthrenyl group, a carbazole group, a triazinyl group, an isoquinoline group, and a dibenzothiophenyl group, each substituted with at least one of a phenyl group, a naphthyl group, an anthracenyl group, and a carbazole group, but are not limited thereto.

In some embodiments, $R_3$ to $R_6$ in Formula 1 may be each independently selected from a hydrogen atom, a deuterium atom, a halogen atom, a hydroxyl group, a cyano group and nitro group; a $C_1$-$C_{30}$ alkyl group; a $C_1$-$C_{30}$ alkyl group substituted with at least one of a hydrogen atom, a deuterium atom, a halogen atom, a hydroxyl group, a cyano group, and a nitro group; a $C_6$-$C_{30}$ aryl group; and a $C_6$-$C_{30}$ aryl group substituted with at least one of a hydrogen atom, a deuterium atom, a halogen atom, a hydroxyl group, a cyano group, a nitro group and a $C_1$-$C_{30}$ alkyl group, but are not limited thereto.

In some embodiments, $R_3$ to $R_6$ in Formula 1 may be each independently selected from a hydrogen atom, a deuterium atom, a halogen atom, a hydroxyl group, a cyano group, and a nitro group; a $C_1$-$C_{30}$ alkyl group; a $C_1$-$C_{30}$ alkyl group substituted with at least one of a hydrogen atom, a deuterium atom, a halogen atom, a hydroxyl group, a cyano group, and a nitro group; a $C_6$-$C_{30}$ aryl group; and a $C_6$-$C_{30}$ aryl group substituted with at least one of a hydrogen atom, a deuterium atom, a halogen atom, a hydroxyl group, a cyano group, a nitro group, and a $C_1$-$C_{30}$ alkyl group, but is not limited thereto.

In some embodiments, $R_3$ to $R_6$ in Formula 1 may be each independently selected from a methyl group, an ethyl group, an n-propyl group, an iso-propyl group, an n-butyl group, an iso-butyl group, a sec-butyl group, and a tert-butyl group; a phenyl group, a naphthyl group, and an anthryl group; and a phenyl group, a naphthyl group, and an anthryl group, each substituted with at least one of a hydrogen atom, a deuterium atom, a methyl group, an ethyl group, an n-propyl group, an iso-propyl group, an n-butyl group, an iso-butyl group, a sec-butyl group, and a tert-butyl group, but are not limited thereto.

In some embodiments, $R_3$ to $R_6$ in Formula 1 may be each independently selected from a methyl group and a phenyl group, but are not limited thereto.

In Formula 1, m1 indicates the number of a moiety represented by

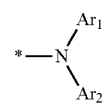

(wherein, * indicates a binding site to $Y_1$), and m2 indicates the number of a moiety represented by

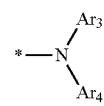

(wherein, * indicates a binding site to $Y_2$). m1 and m2 in Formula 1 are each independently an integer of 1 or 2, and when m1 is 2, two of a moiety represented by

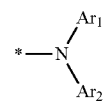

(wherein, * indicates a linking site to $Y_1$) may be identical to or different from each other, and when m2 is 2, two of a moiety represented by

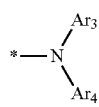

(wherein, * indicates a linking site to $Y_2$) may be identical to or different from each other.

In some embodiments, m1 and m2 in Formula 1 may be 1, but is not limited thereto.

In Formula 1, o1 indicates the number of a moiety represented by

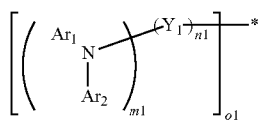

(wherein, * indicates a linking site), and o2 indicates the number of a moiety represented by

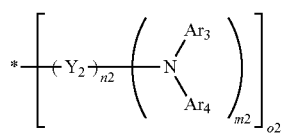

(wherein, * indicates a linking site). o1 and o2 in Formula 1 are each independently an integer of 0 to 5, and when o1 is an integer of 2 or more, a plurality of moieties each represented by

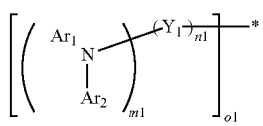

(wherein, * indicates a linking site) may be identical to or different from each other, and when o2 is an integer of 2 or more, a plurality of moieties each represented by

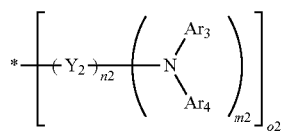

(wherein, * indicates a linking site) may be identical to or different from each other, provided that o1 and o2 are not 0 at the same time.

In some embodiments, o1 and o2 in Formula 1 are each independently 0 or 1, provided that o1 and o2 are not 0 at the same time, but are not limited thereto.

In Formula 1, a1 indicates the number of $R_1$, and a2 indicates the number of $R_2$. a1 and a2 in Formula 1 are each independently an integer of 0 to 4, and when a1 is an integer of 2 or more, a plurality of $R_1$ may be identical to or different from each other; and when a2 is an integer of 2 or more, a plurality of $R_2$ may be identical to or different from each other.

In some embodiments, a1 and a2 in Formula 1 may be each independently 0 or 1, but are not limited thereto. As another example, a1 and a2 in Formula 1 may be 0, but are not limited thereto.

As another example, in Formula 1, o1 is 1, o2 is 1, a1 is 0, and a2 is 0, but an embodiment of the present invention is not limited thereto.

As another example, in Formula 1, o1 is 1, o2 is 0, a1 is 0, and a2 is 1, but an embodiment of the present invention is not limited thereto.

In some embodiments, the compound of Formula 1 may be represented by Formula 1a below, but an embodiment of the present invention is not limited thereto:

Formula 1a

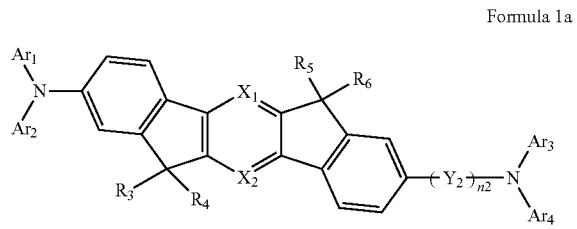

wherein, in Formula 1a, $X_1$ is $C(R_{11})$ and $X_2$ is N (nitrogen); or $X_1$ is N (nitrogen) and $X_2$ is $C(R_{12})$, provided that a case in which $X_1$ is $C(R_{11})$ and $X_2$ is $C(R_{12})$ is excluded; and a moiety represented by $(Y_2)_{n2}$ may be one of Formulae 2a to 2q below;

2a

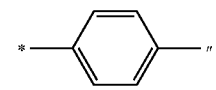

2b

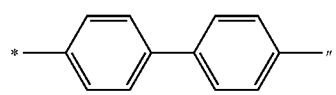

2c

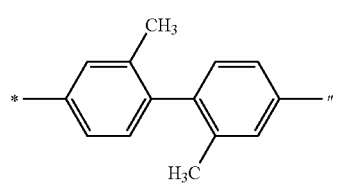

2d

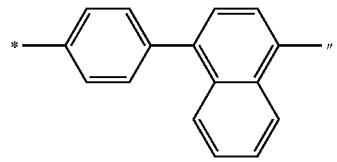

2e

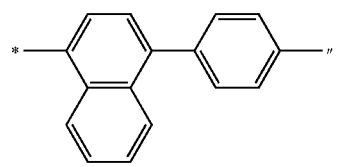

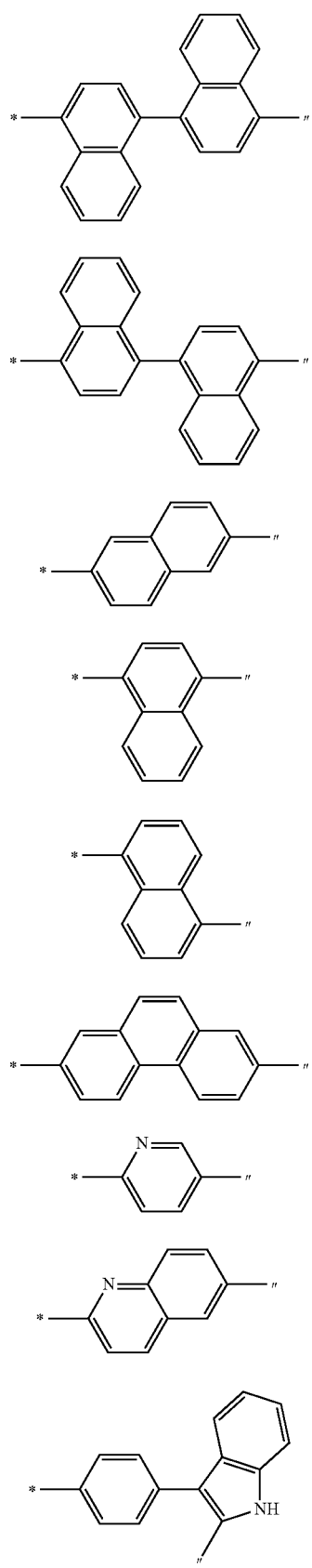
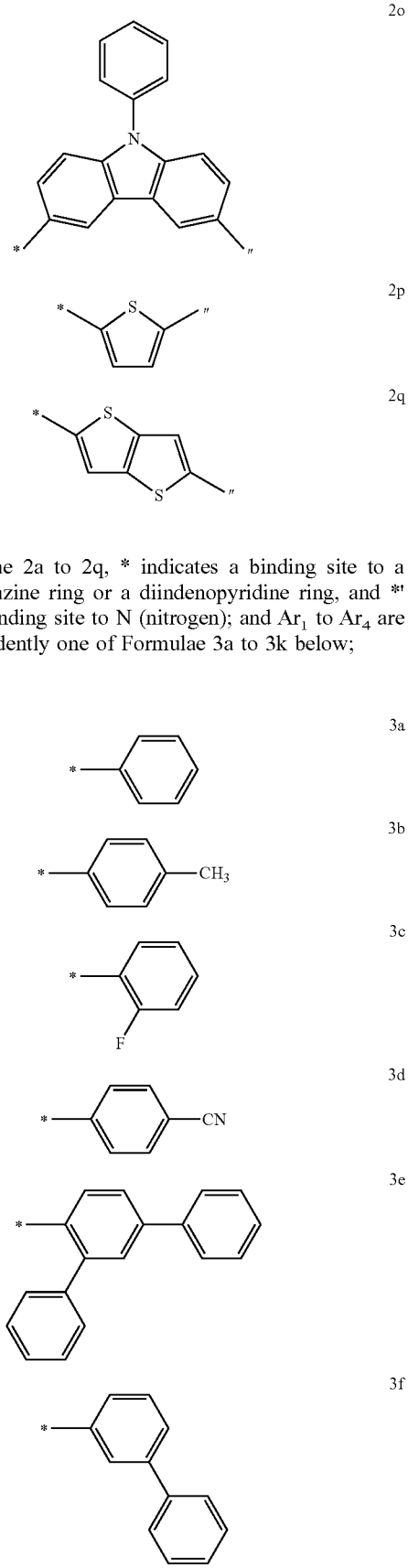
In Formulae 2a to 2q, * indicates a binding site to a diindeno pyrazine ring or a diindenopyridine ring, and *″ indicates a binding site to N (nitrogen); and $Ar_1$ to $Ar_4$ are each independently one of Formulae 3a to 3k below;

-continued

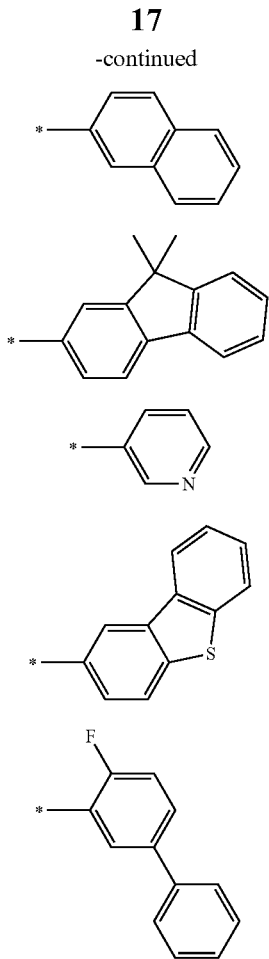

3g

3h

3i

3j

3k

In Formulae 3a to 3k, * indicates a binding site to N (nitrogen); $R_{11}$ and $R_{12}$ are selected from a hydrogen atom and a deuterium atom; and $R_3$ to $R_6$ may be each independently selected from a methyl group and a phenyl group.

In some embodiments, the compound of Formula 1 may be represented by Formula 1b below, but is not limited thereto:

Formula 1b

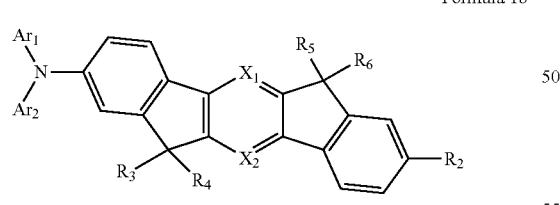

in Formula 1b, $X_1$ is $C(R_{11})$ and $X_2$ is N (nitrogen), or $X_1$ is N (nitrogen) and $X_2$ is $C(R_{12})$, provided that a case in which $X_1$ is $C(R_{11})$ and $X_2$ is $C(R_{12})$ is excluded; and $Ar_1$ and $Ar_2$ may be one of Formulae 3a to 3k below;

3a

-continued

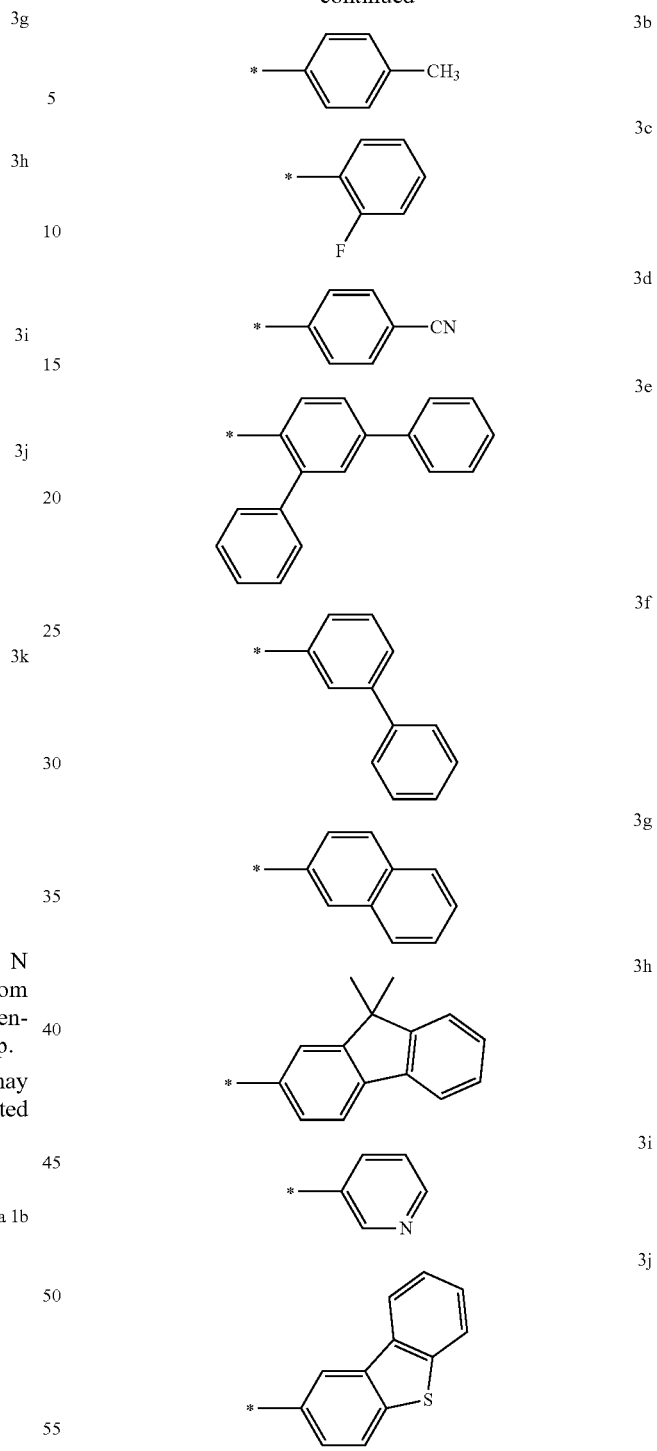

3b

3c

3d

3e

3f

3g

3h

3i

3j

3k

* in Formulae 3a to 3k indicates a binding site to N (nitrogen);
$R_{11}$ and $R_{12}$ may be each independently selected from a hydrogen atom and a deuterium atom; $R_2$ may be independently selected from a hydrogen atom and a deuterium atom;
a phenyl group, a naphthyl group, a phenanthrenyl group, a triazinyl group, a carbazole group, an isoquinoline group, and a dibenzothiophenyl group; and a phenyl group, a naphthyl group, a phenanthrenyl group, a carbazole group, a triazinyl group, an isoquinoline group, and a dibenzothiophenyl group, each substituted with at least one of a phenyl group, a naphthyl group, an anthracenyl group, and a carbazole group.

In some embodiments, the compound of Formula 1 may be selected from Compounds 1 to 90 below, and is not limited thereto:

1

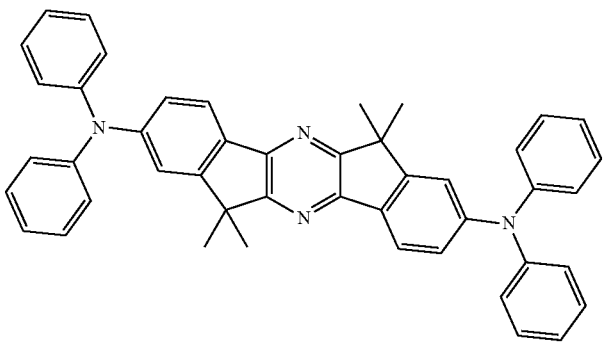

2

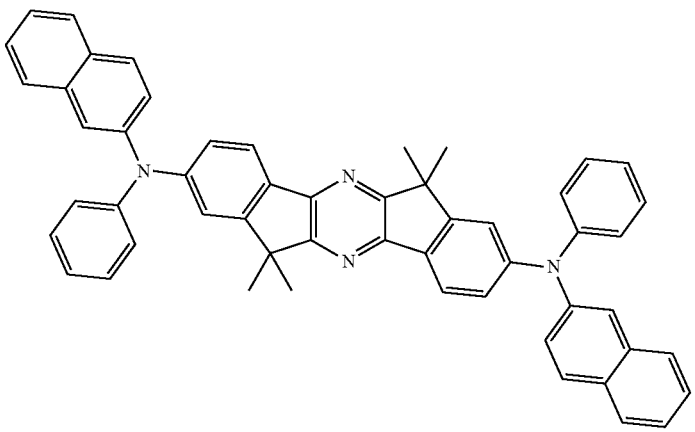

3

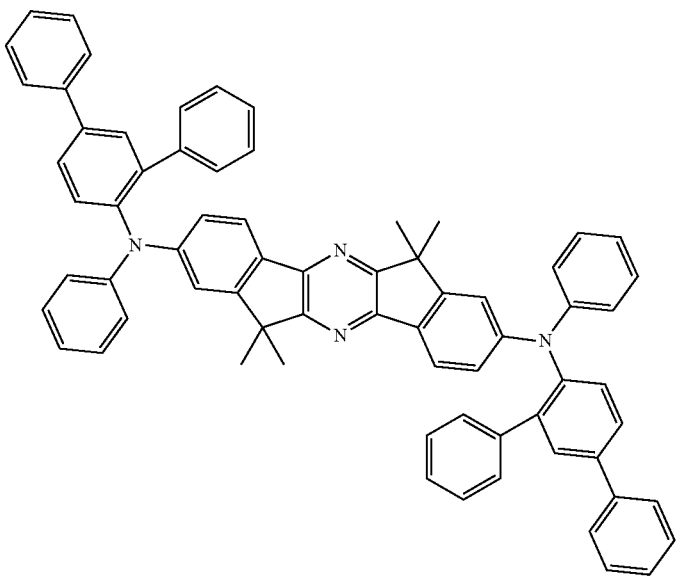

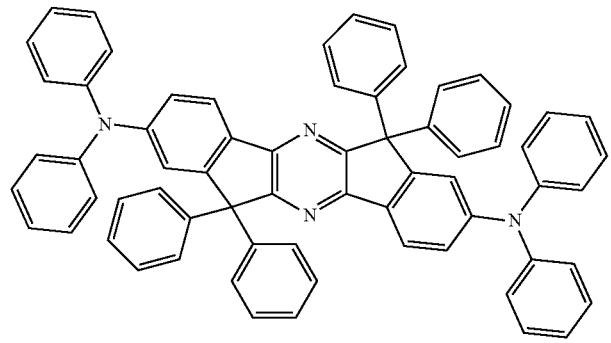
4
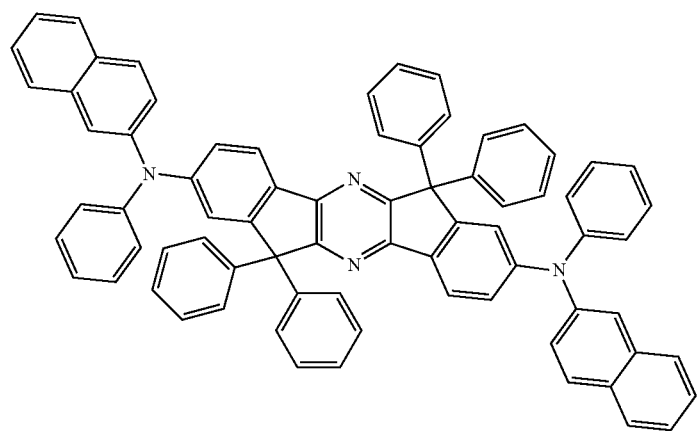
5
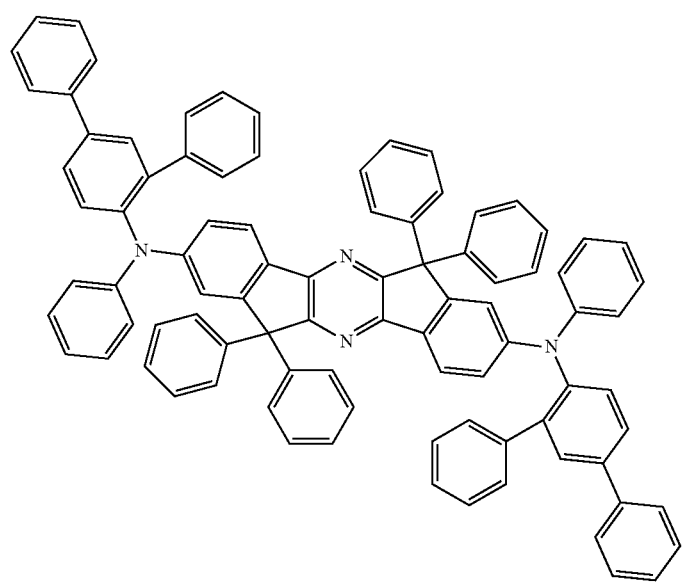
6

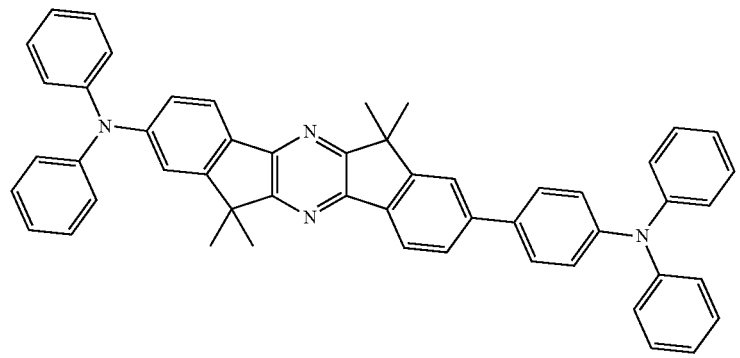
7
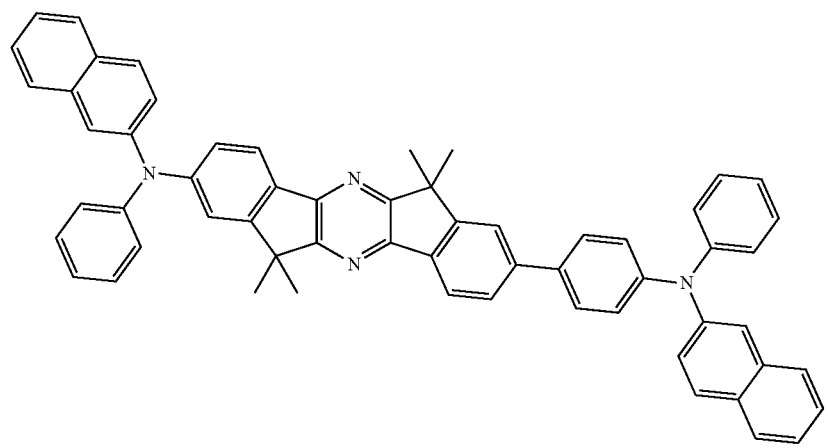
8
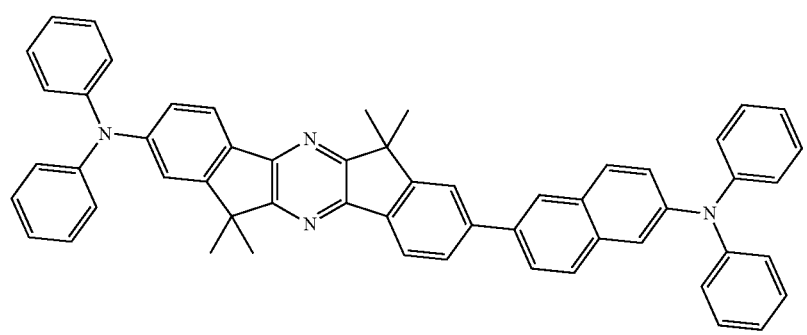
9
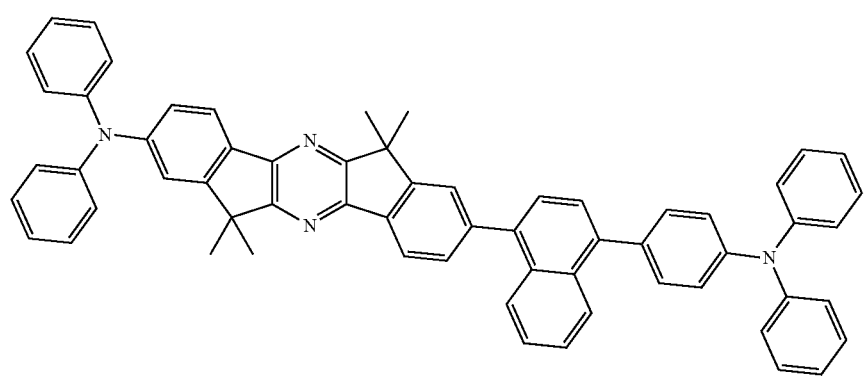
10

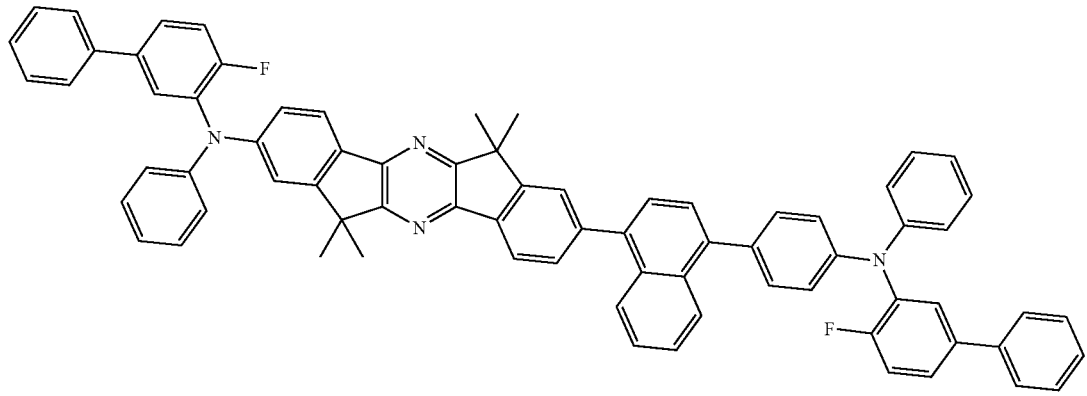
11
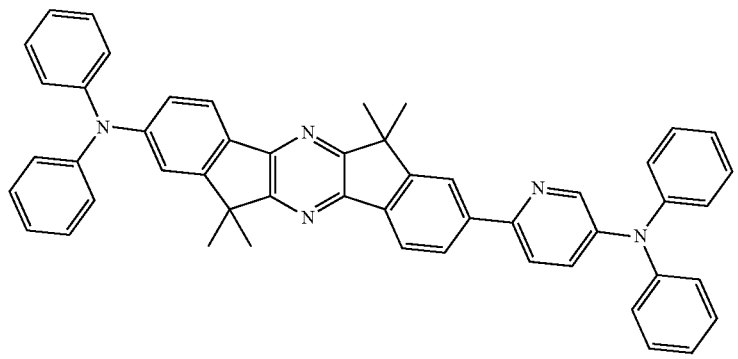
12
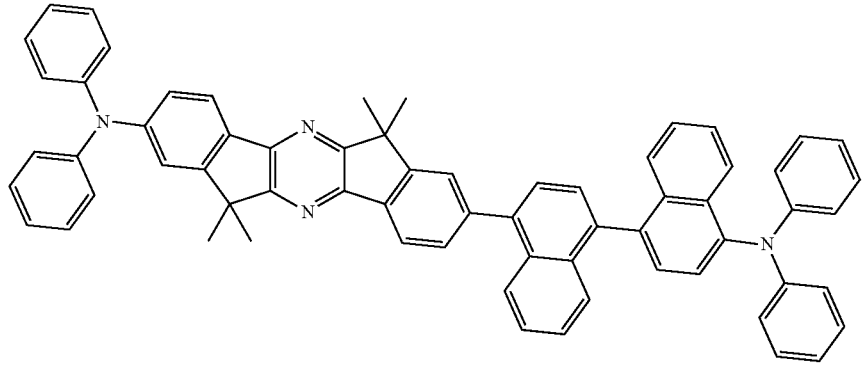
13
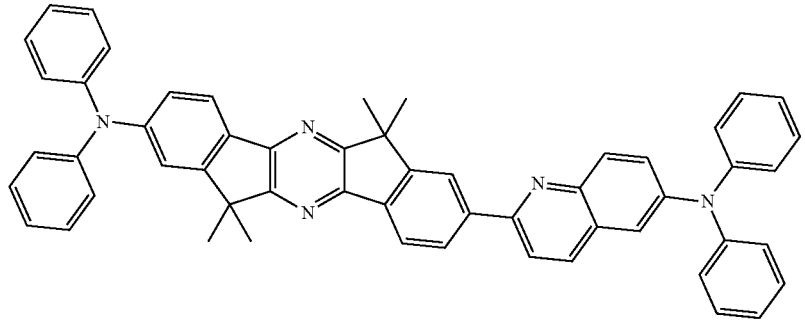
14

-continued
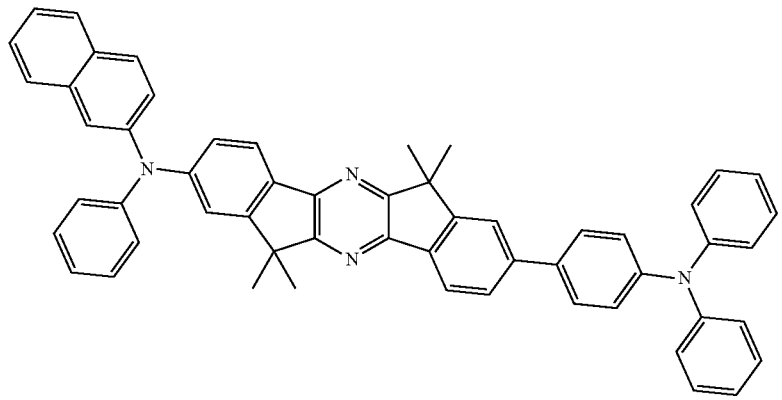
15
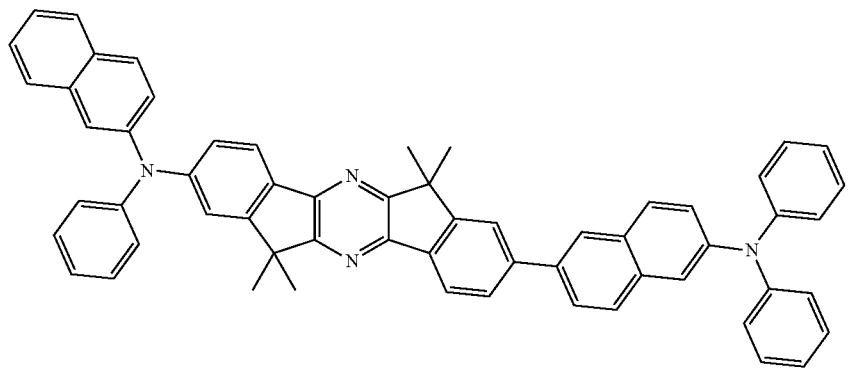
16
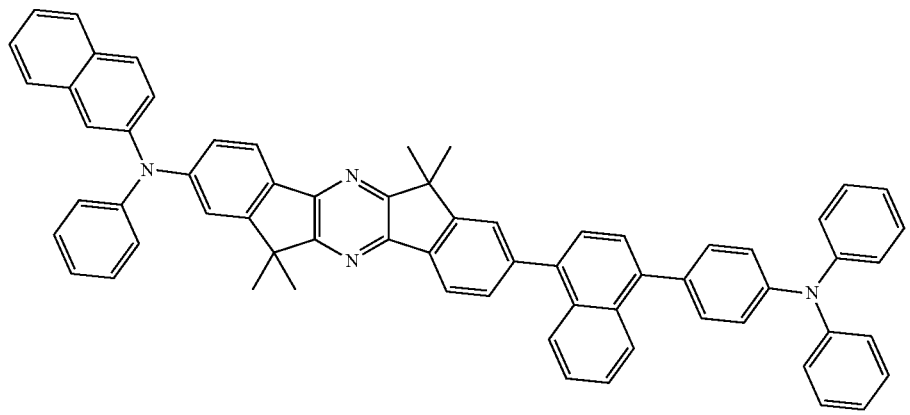
17
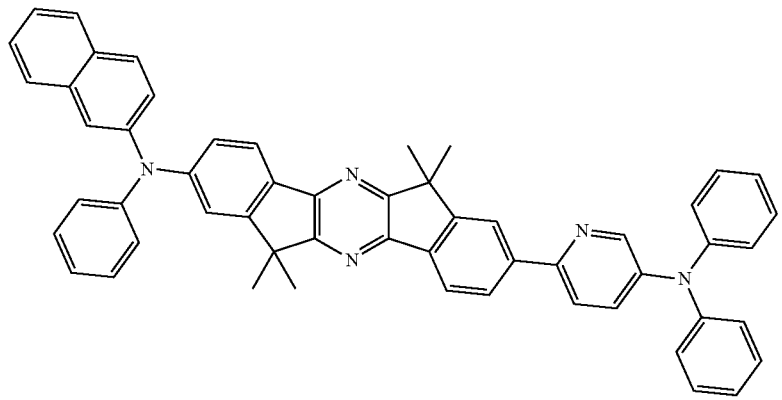
18

-continued
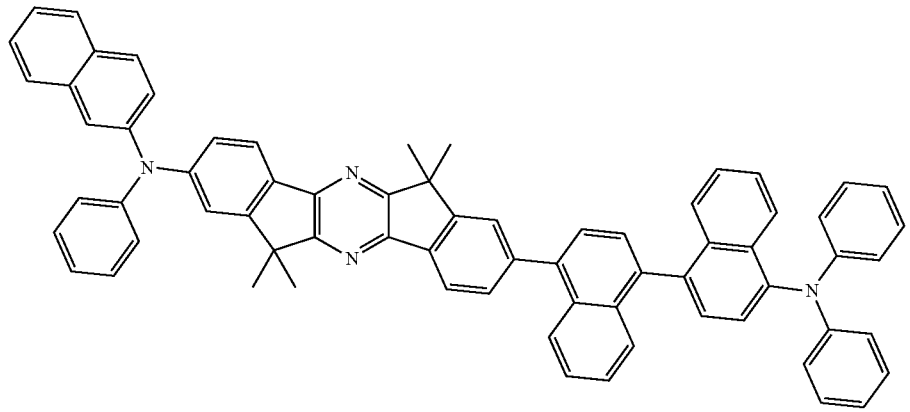
19
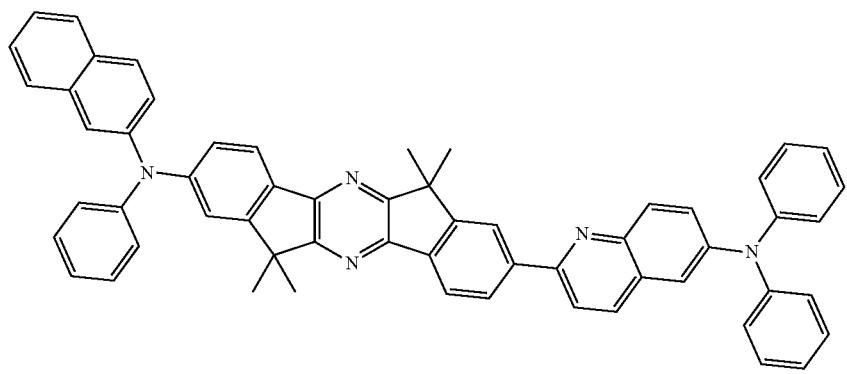
20
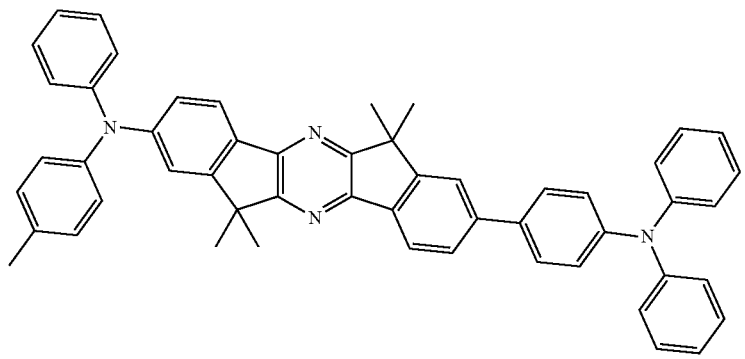
21
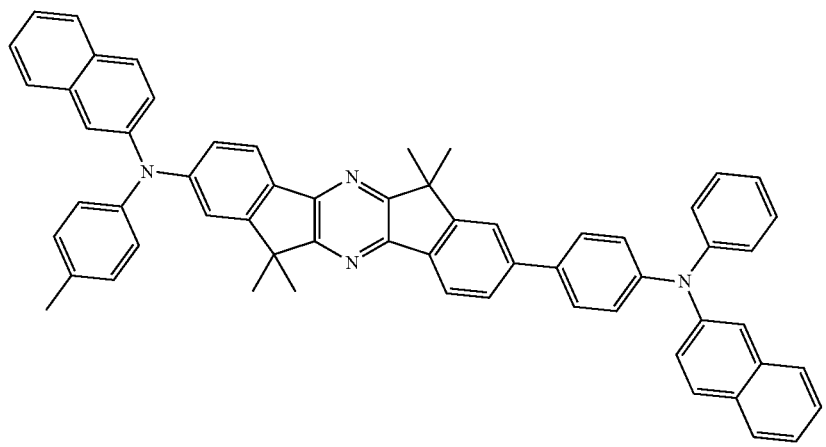
22

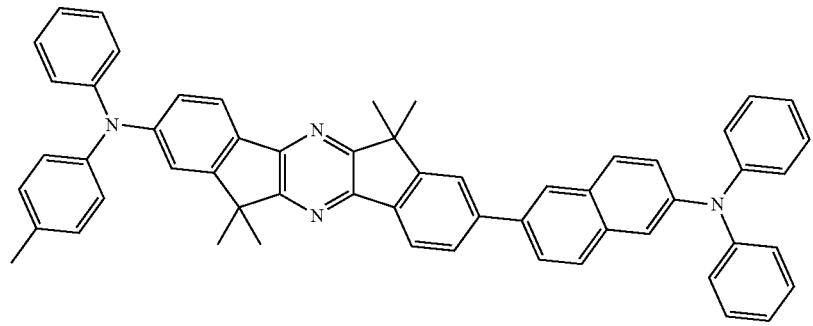
23
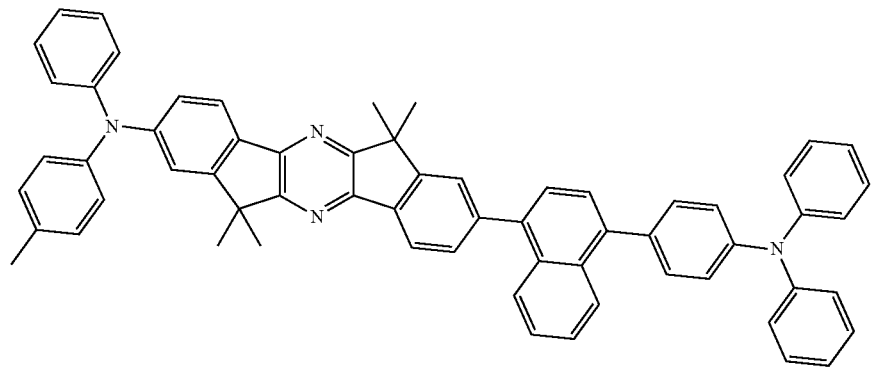
24
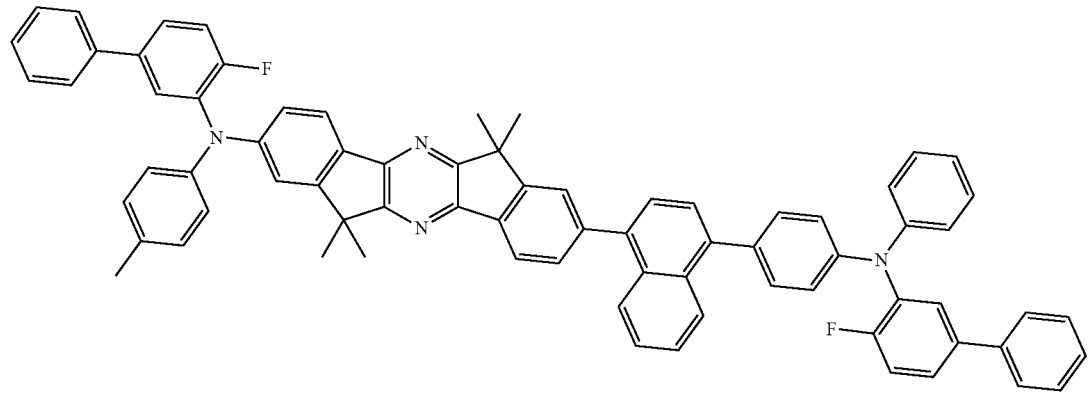
25
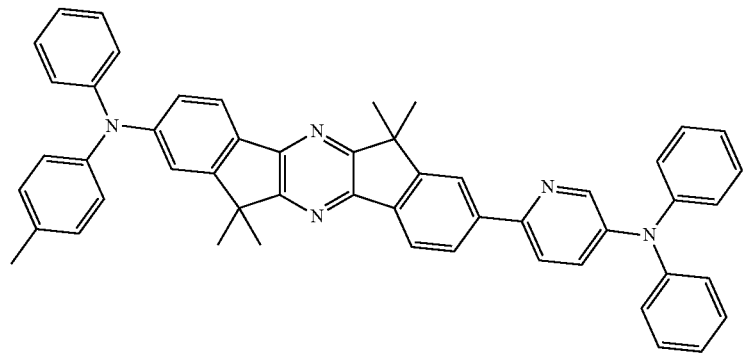
26

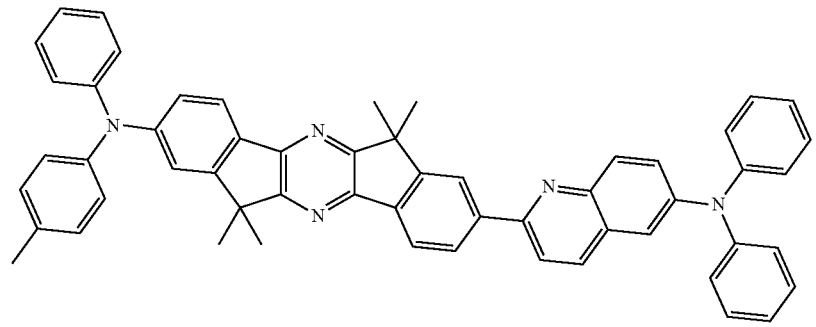
27
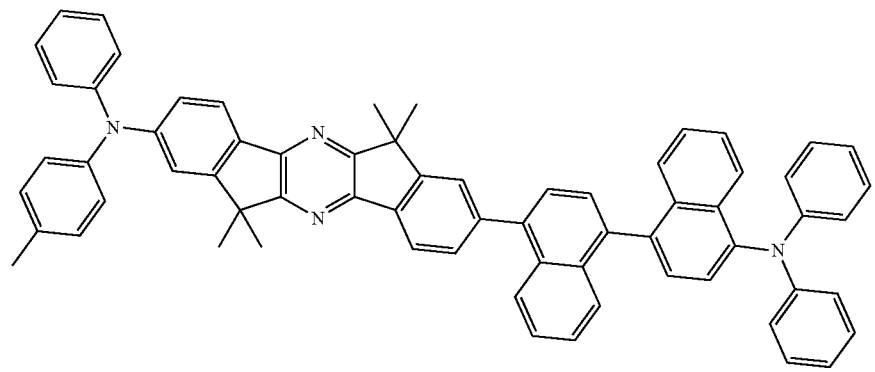
28
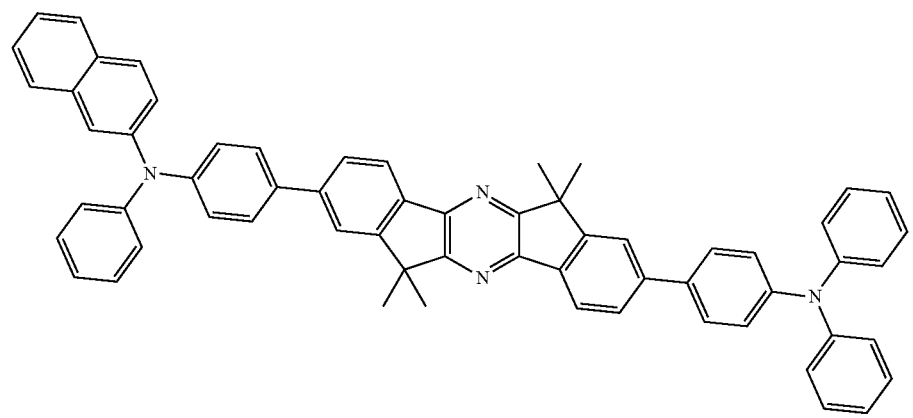
29
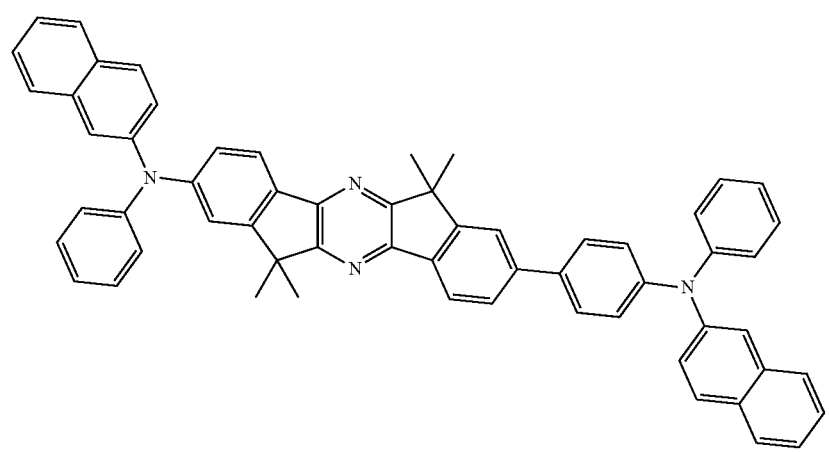
30

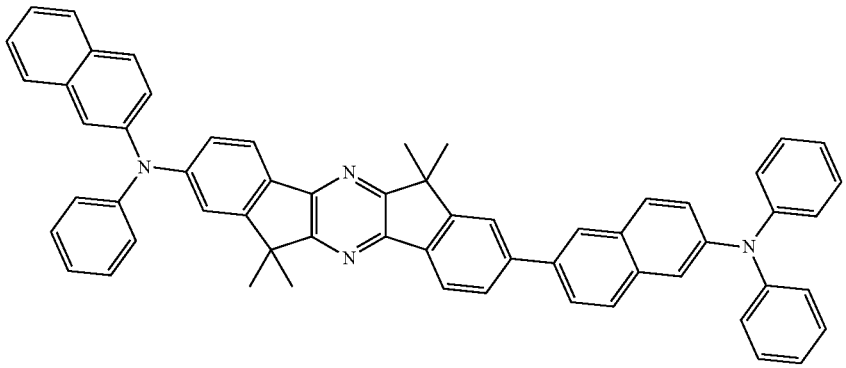
31
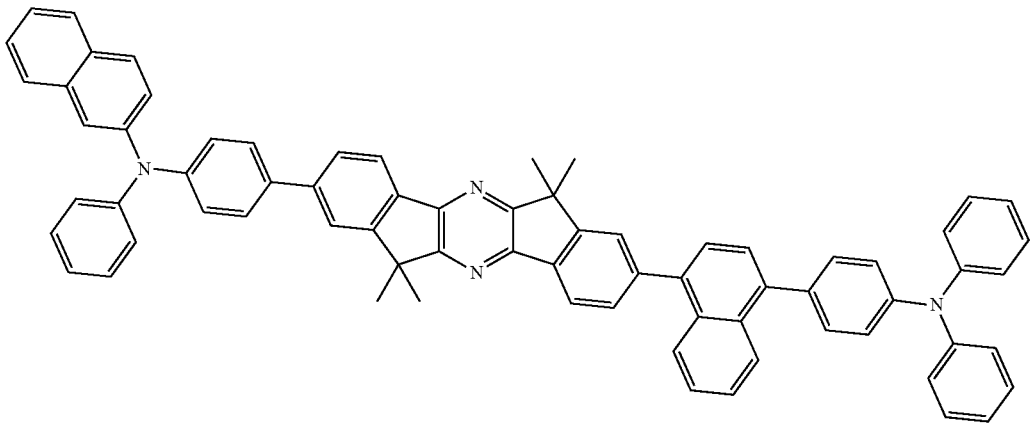
32
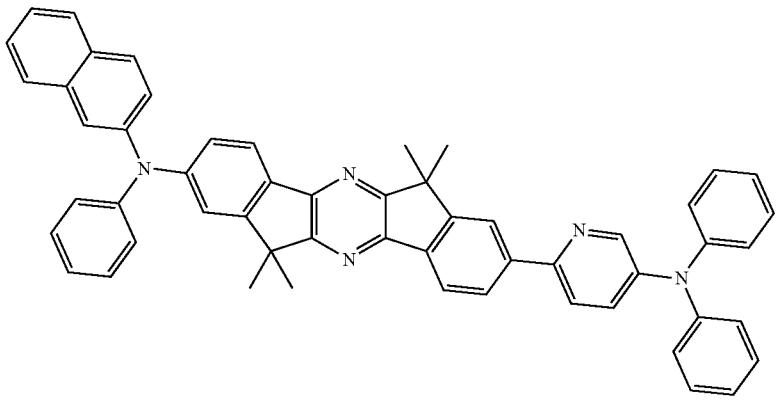
33
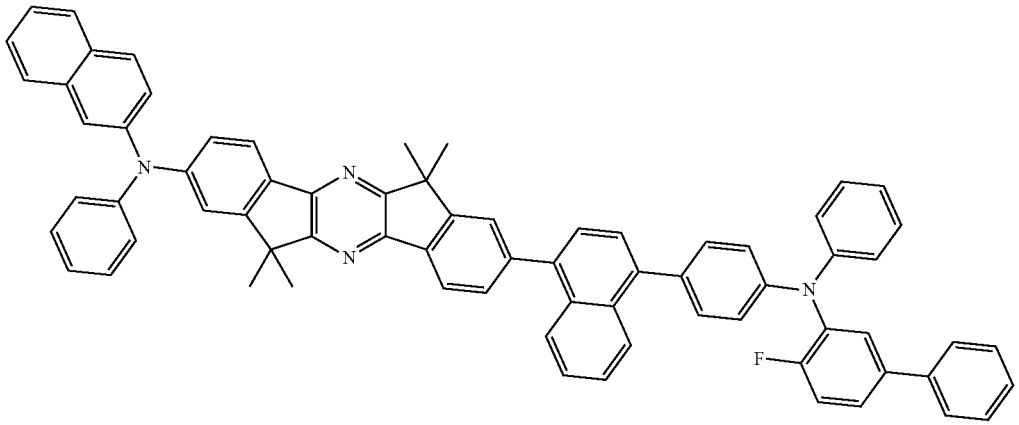
34

35
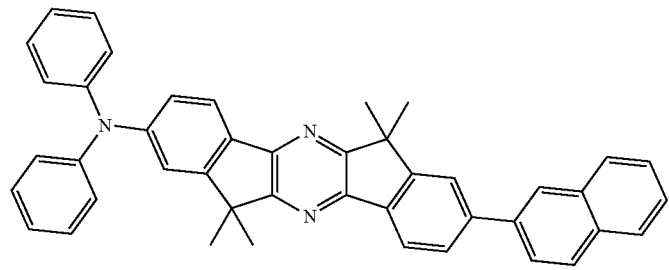
36
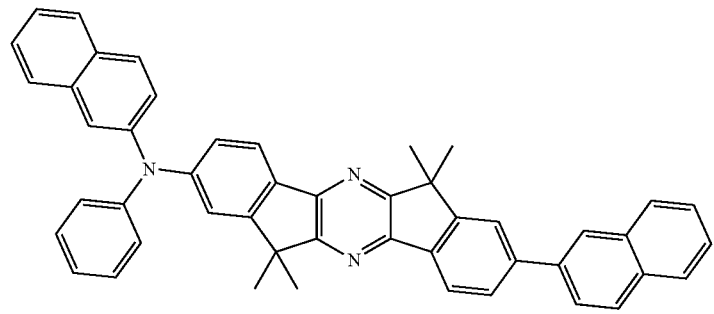
37
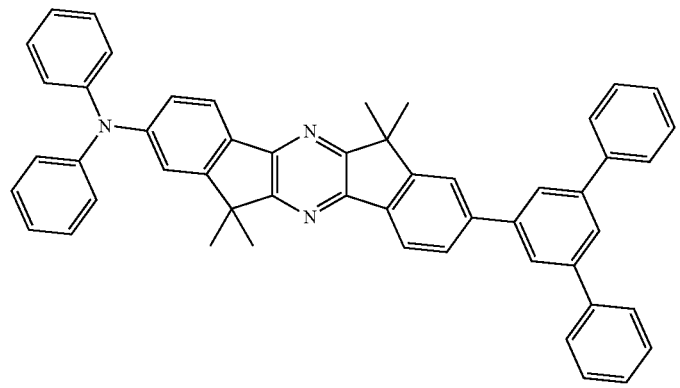
38
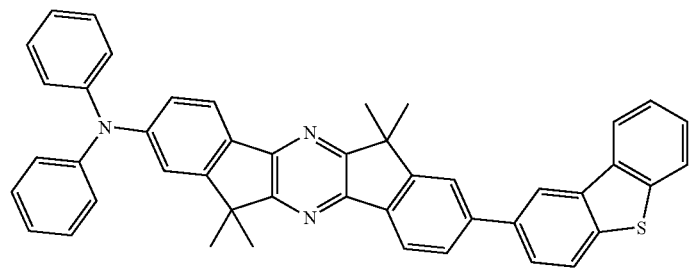
39
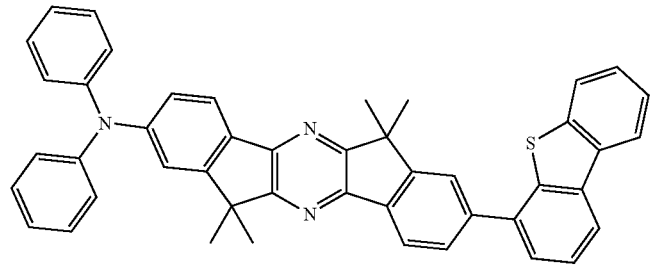

-continued
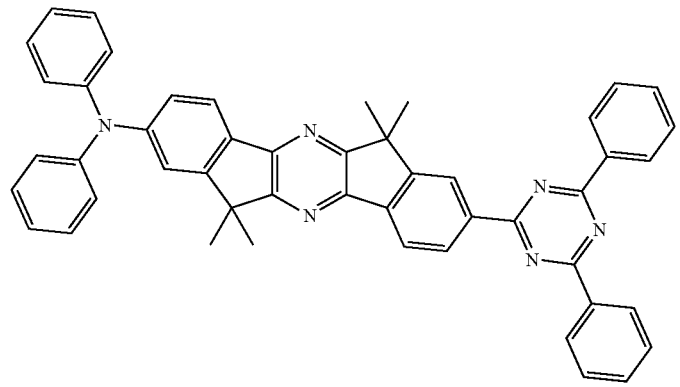
40
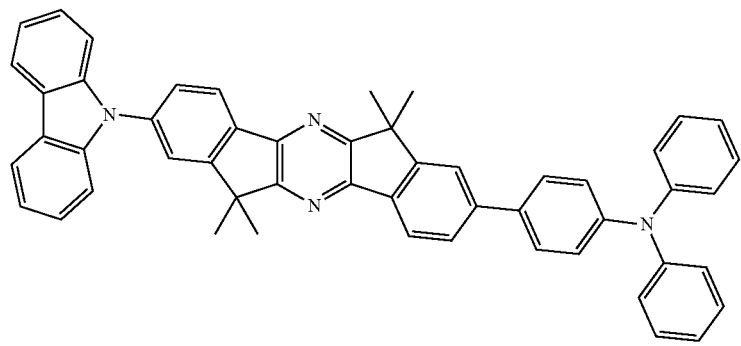
41
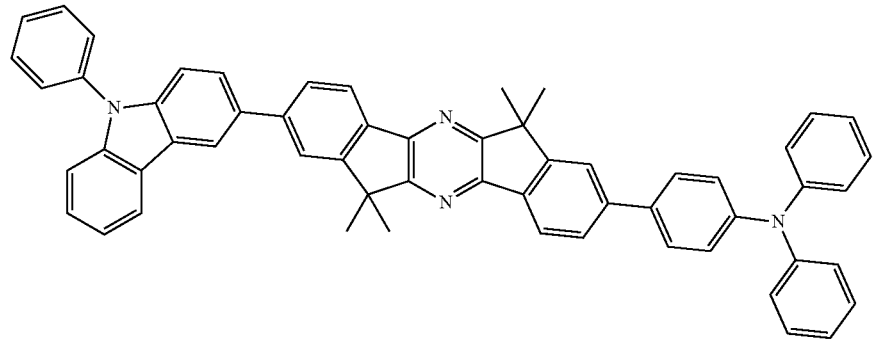
42
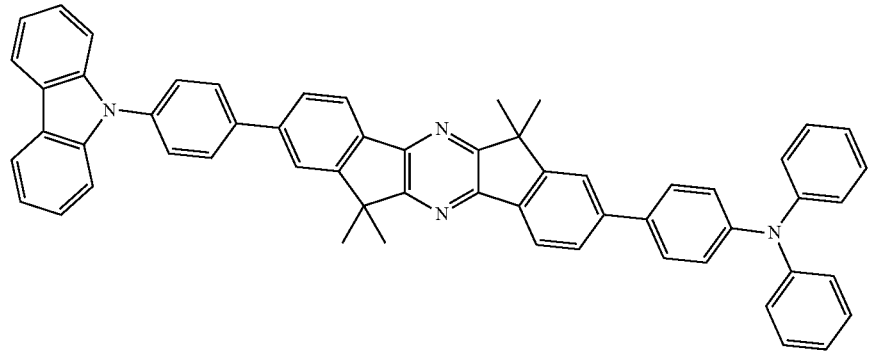
43

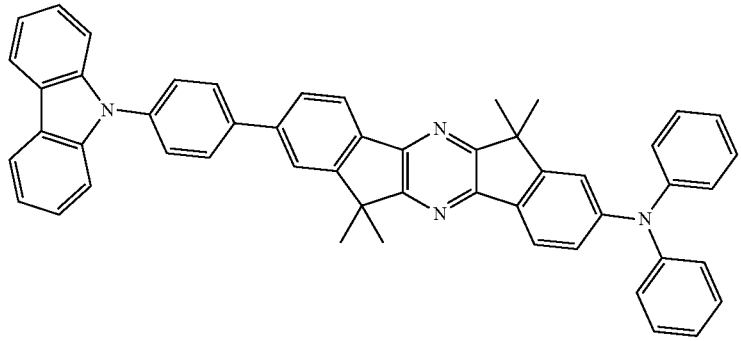
44
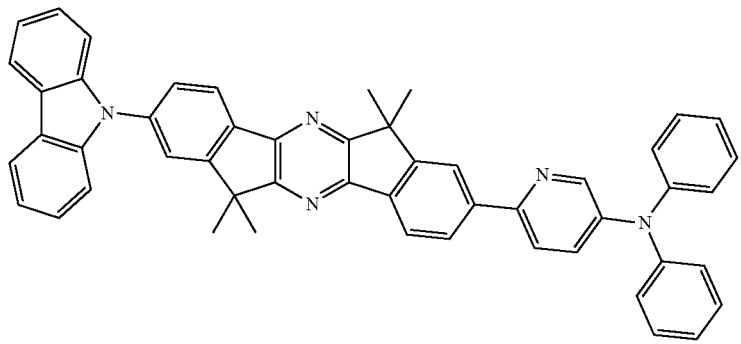
45
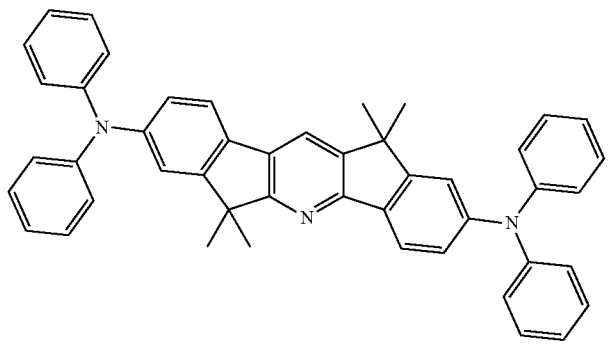
46
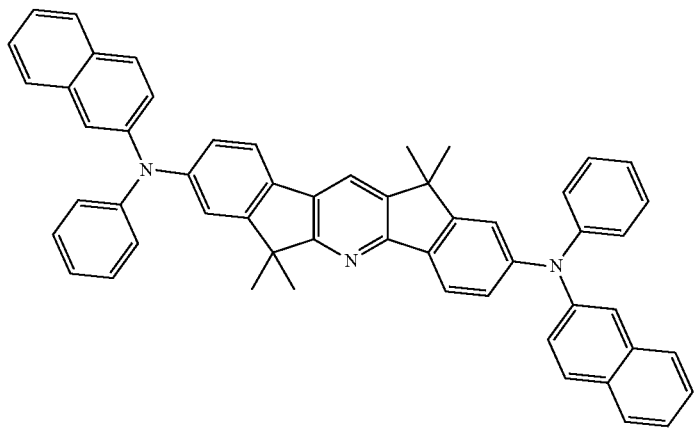
47

-continued
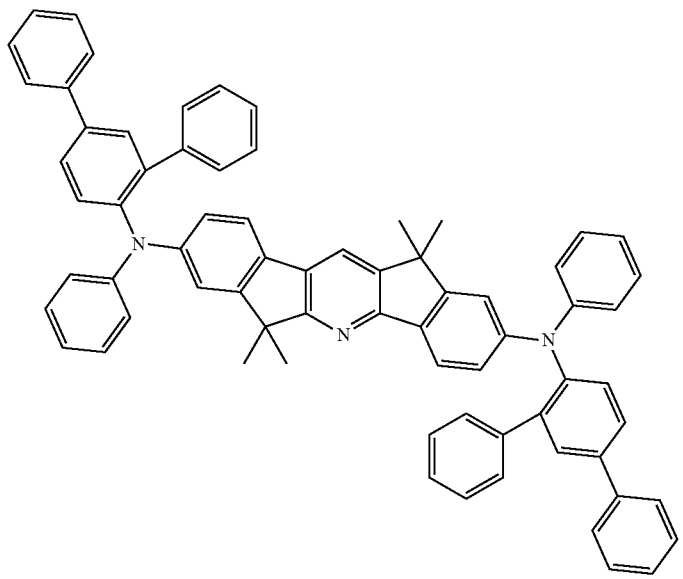
48
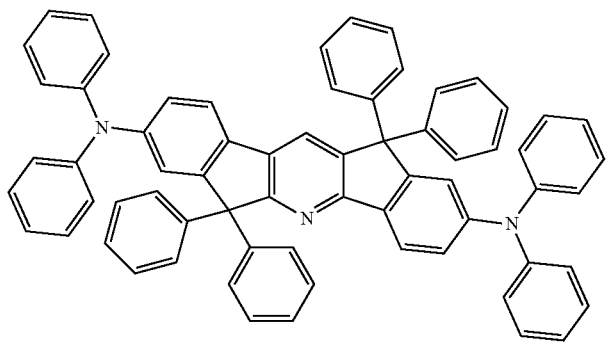
49
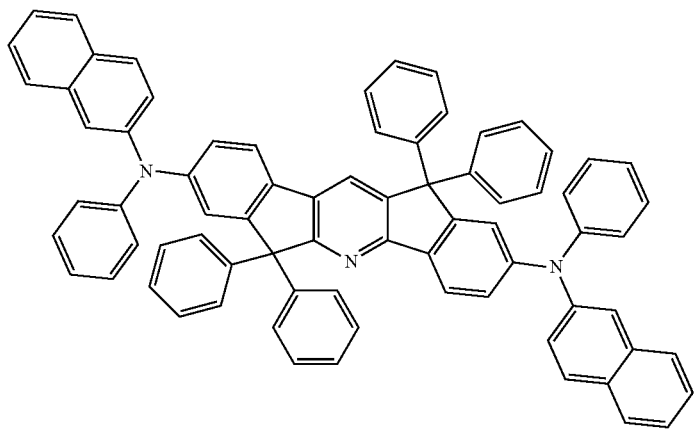
50

-continued
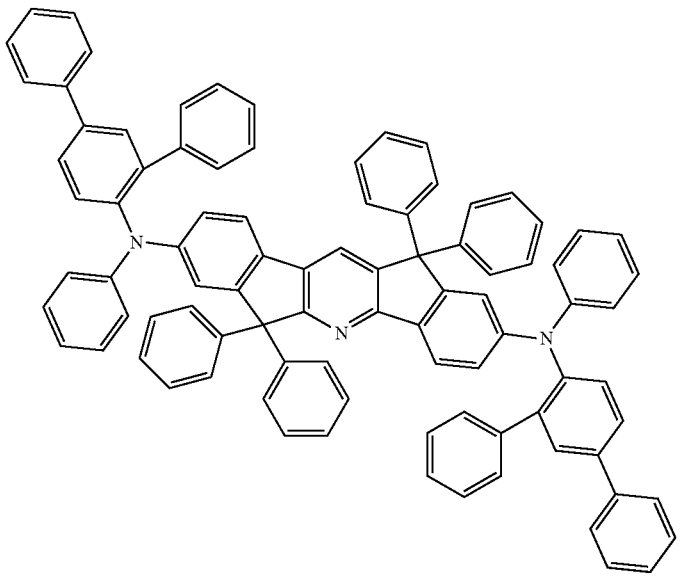
51
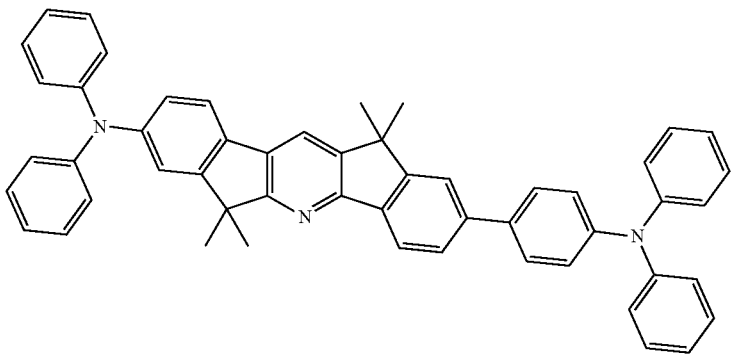
52
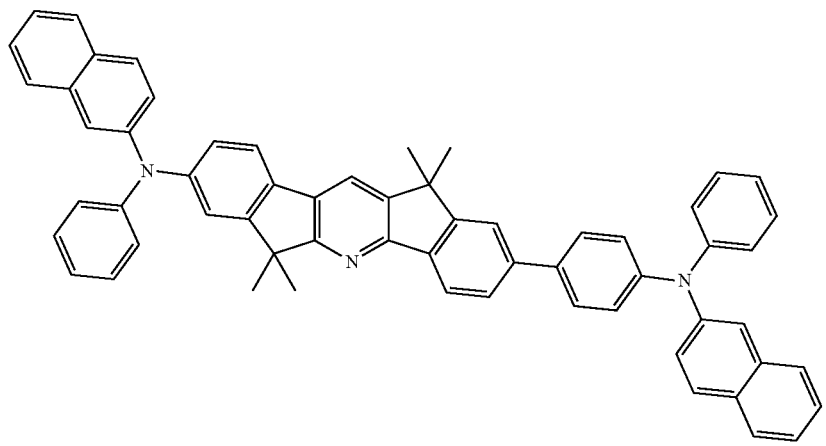
53

54
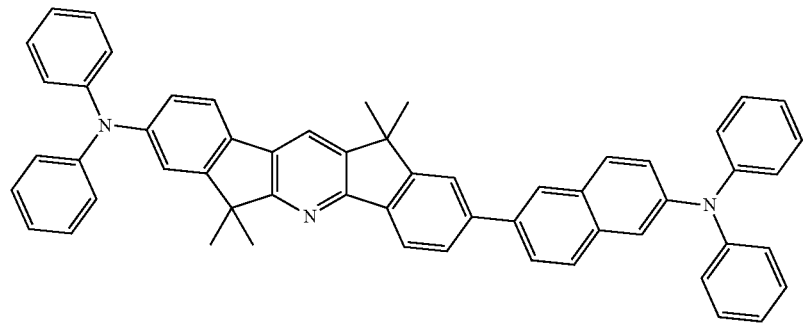
55
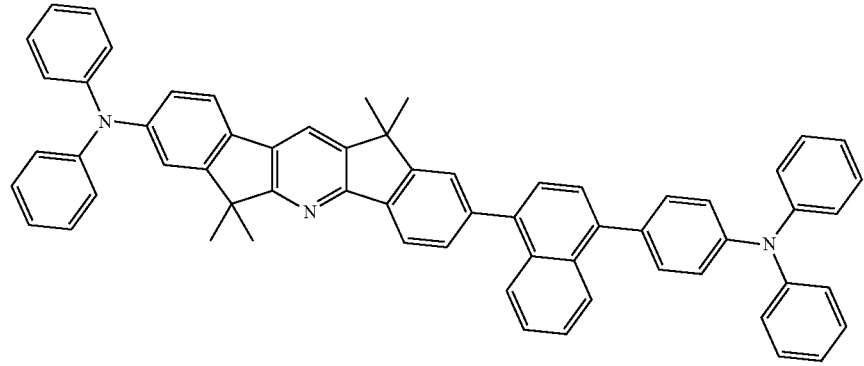
56
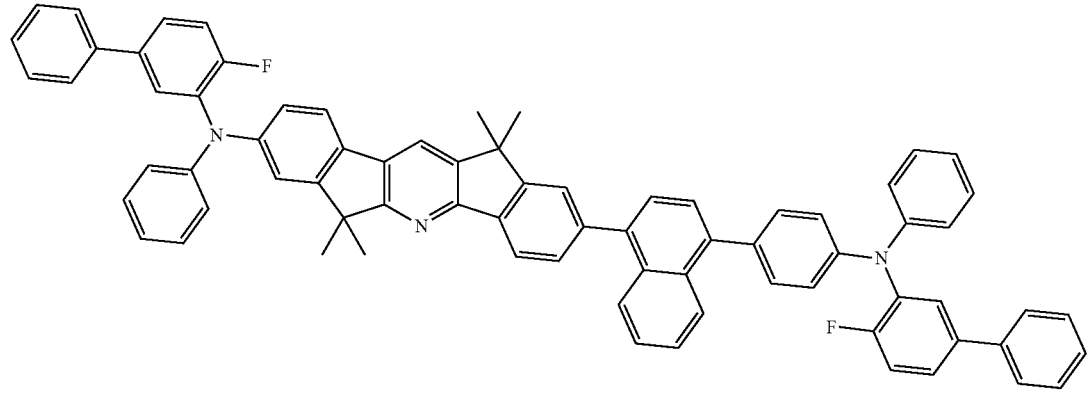
57
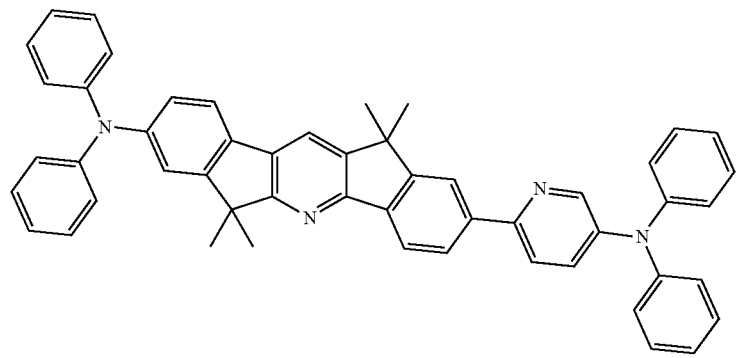

58
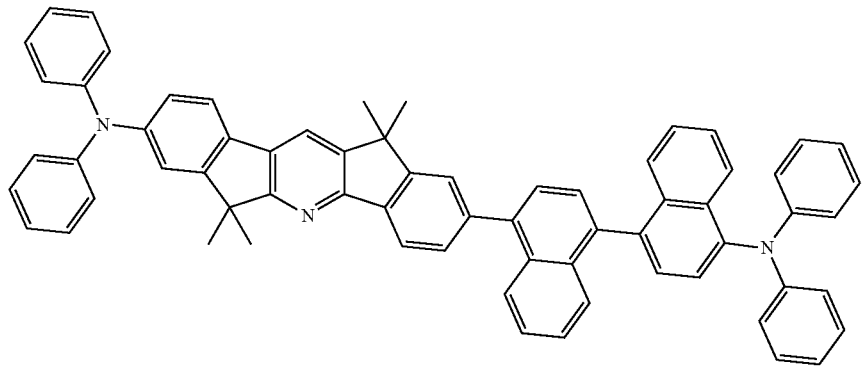
59
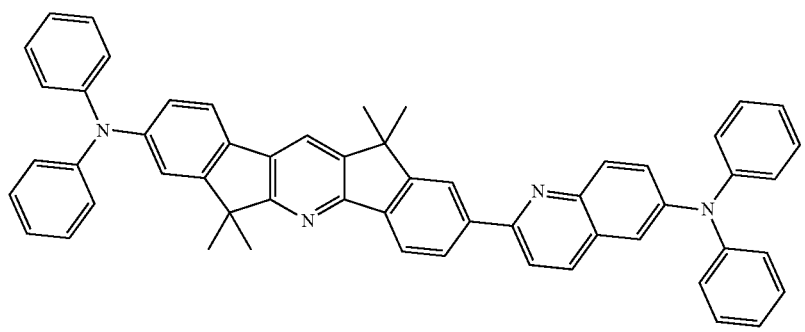
60
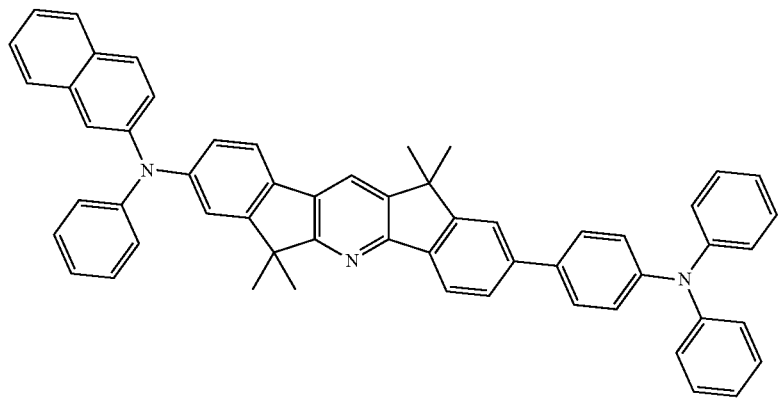
61
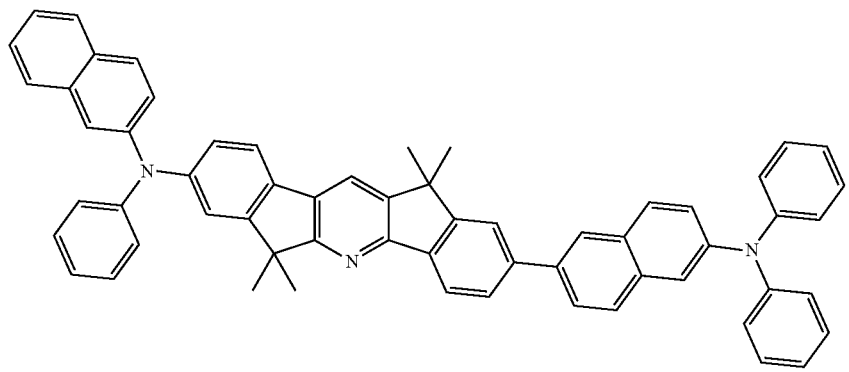

-continued
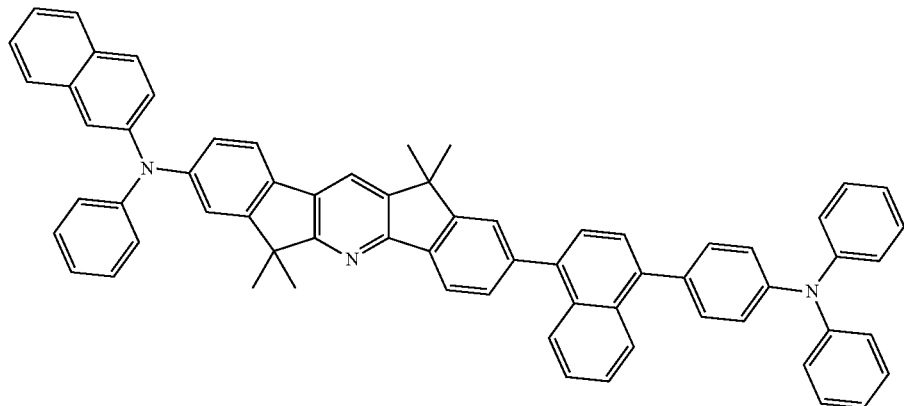
62
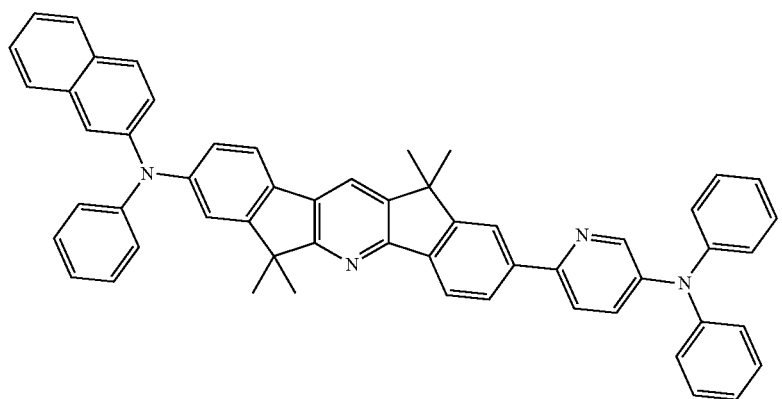
63
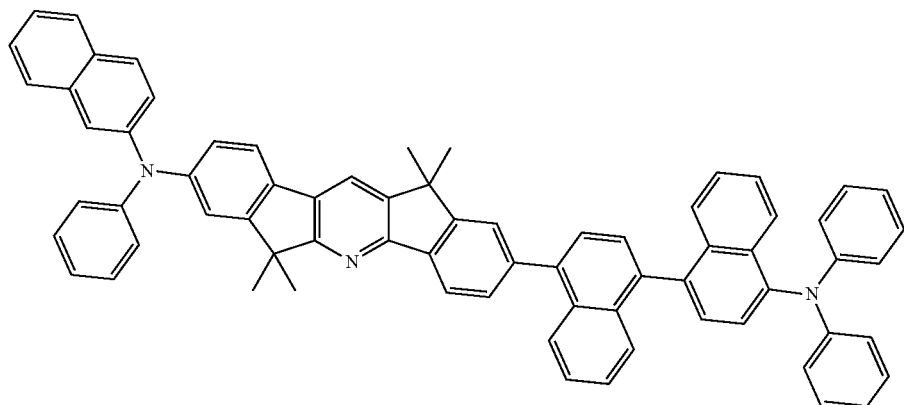
64
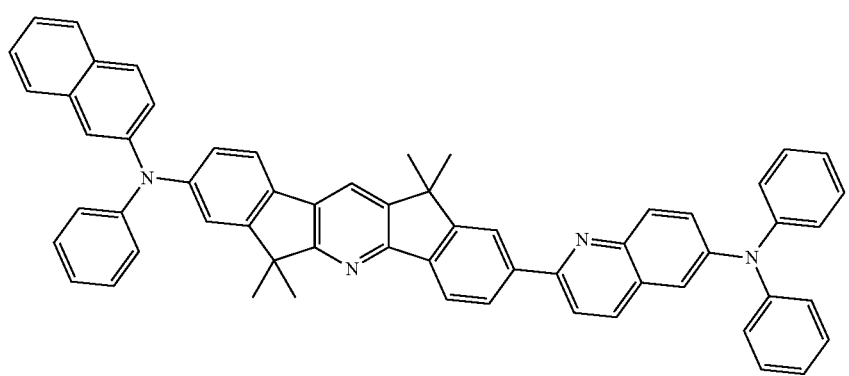
65

66
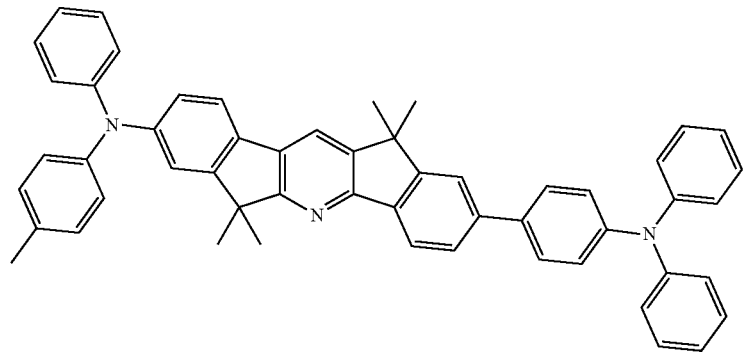
67
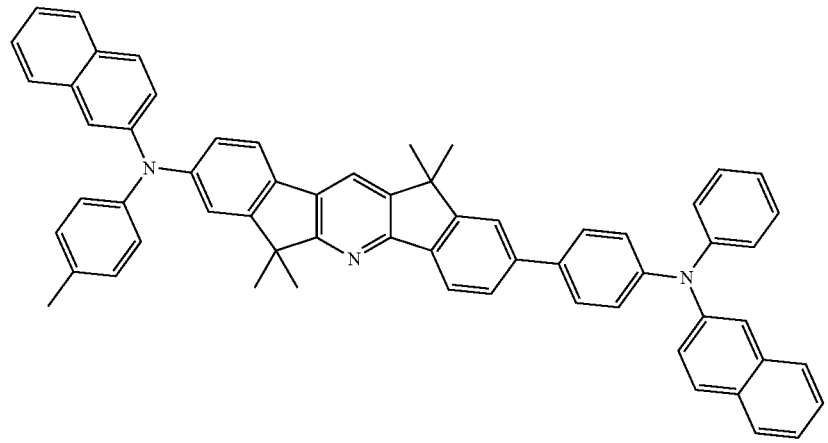
68
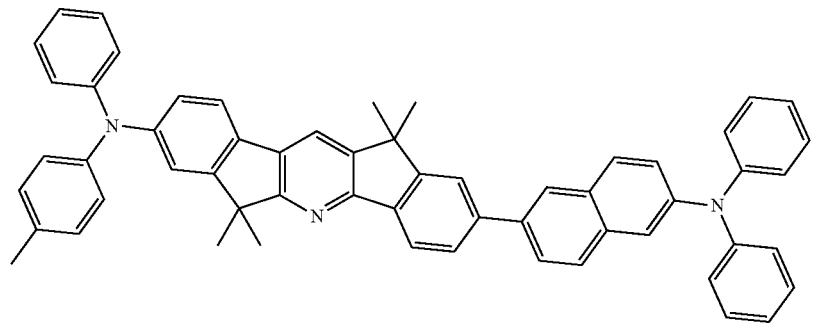
69
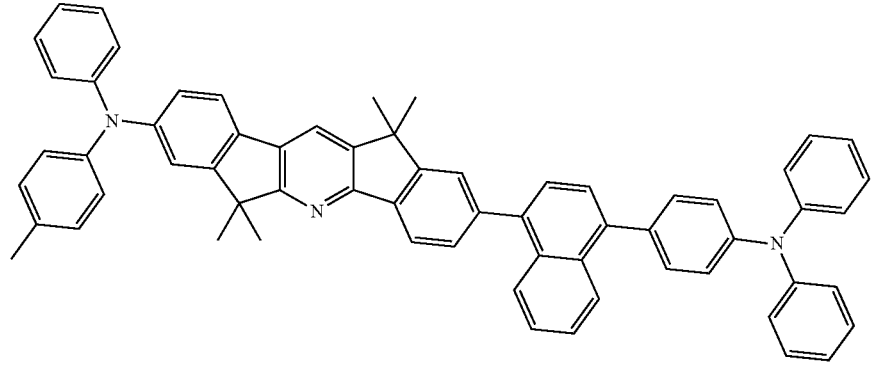

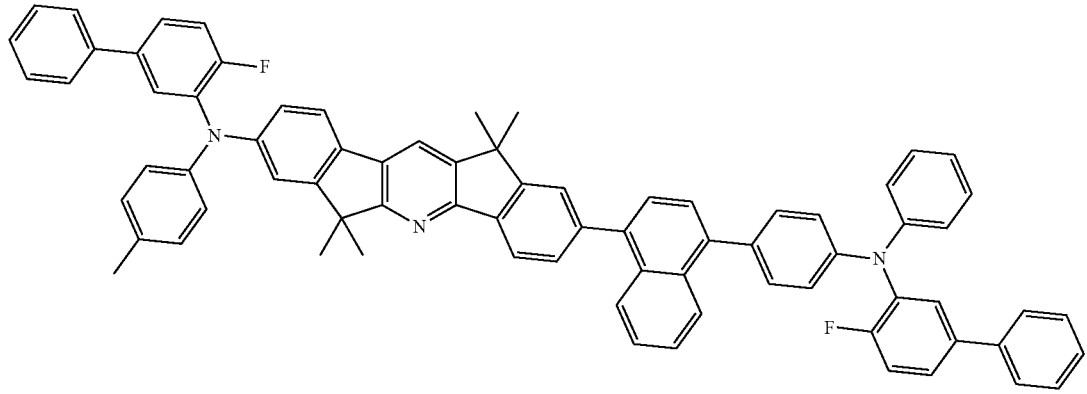
70
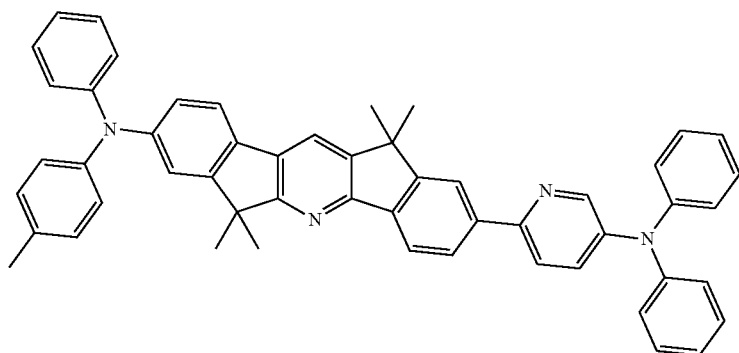
71
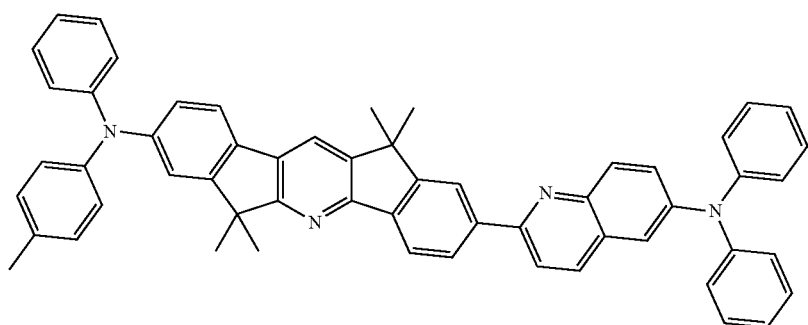
72
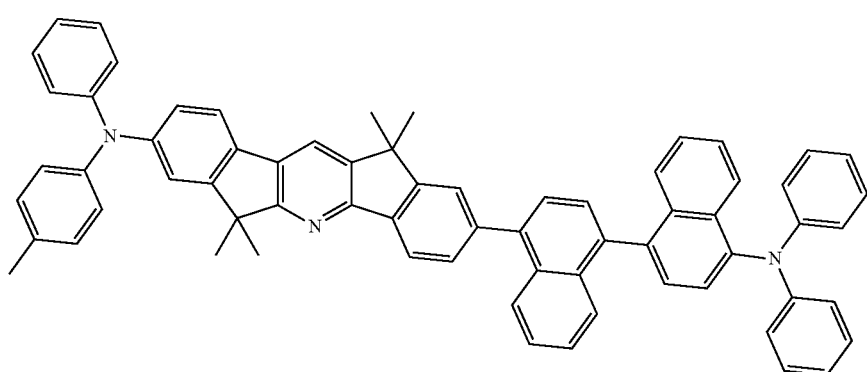
73

-continued
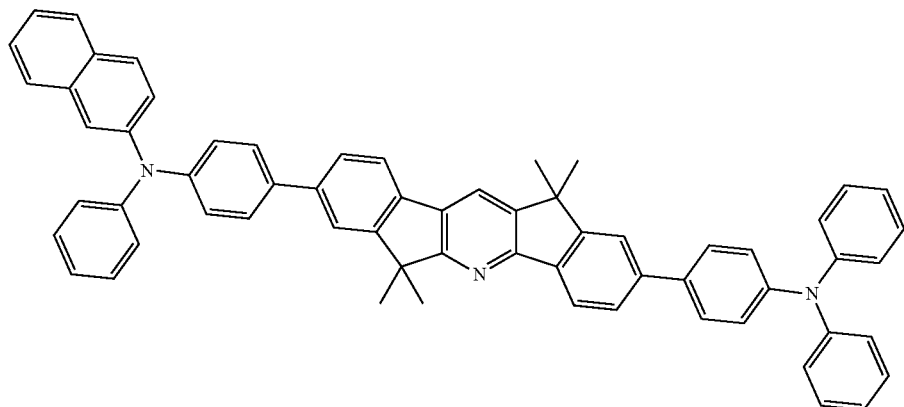
74
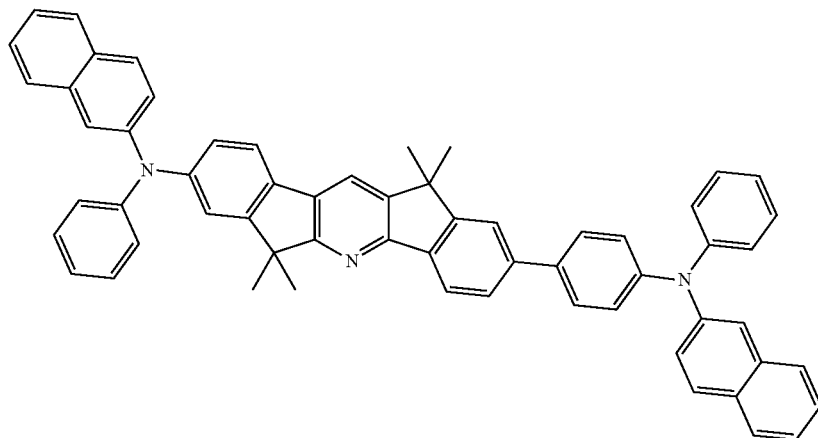
75
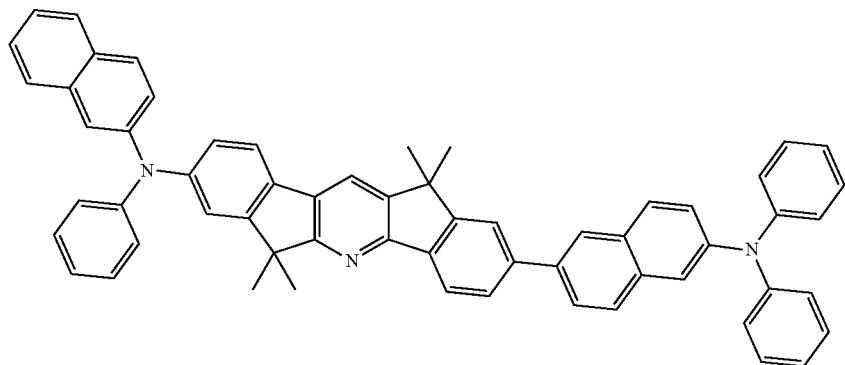
76
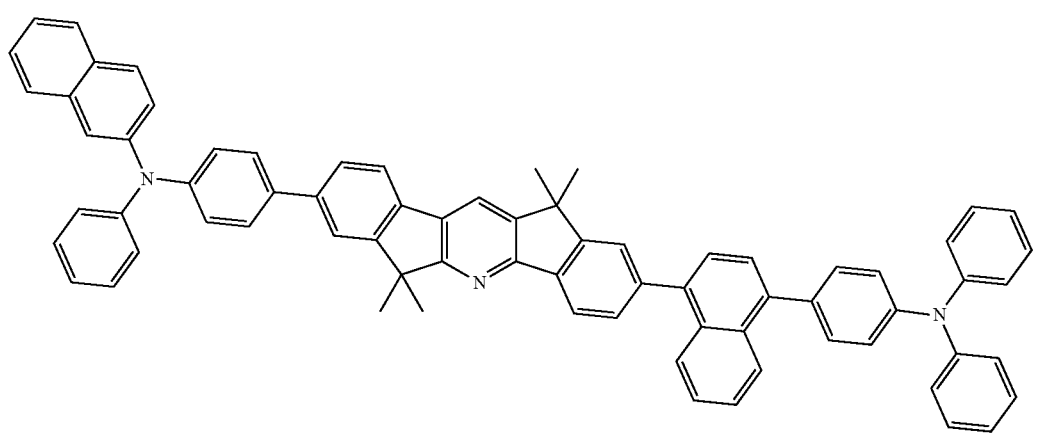
77

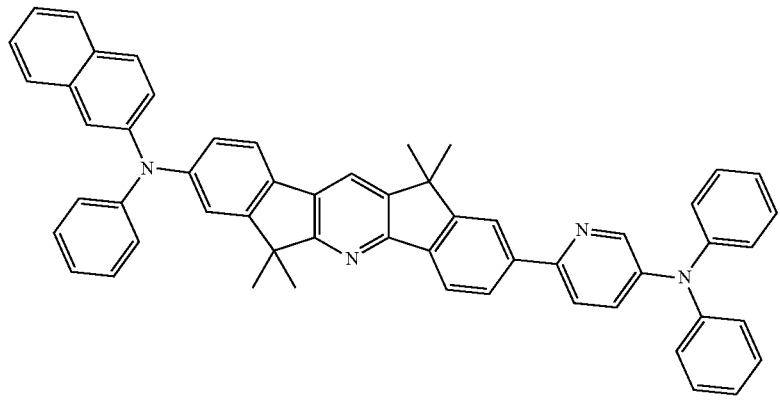
78
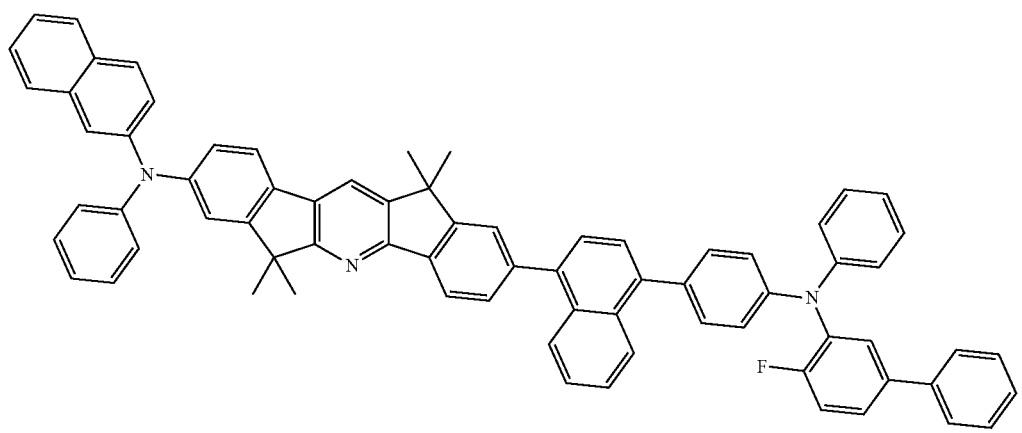
79
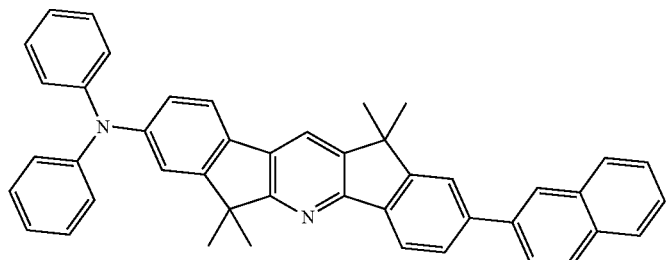
80
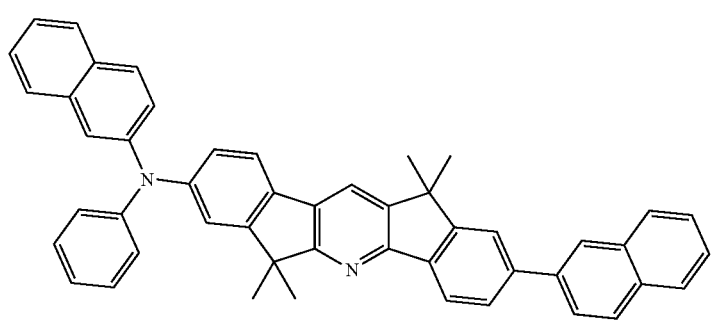
81

82
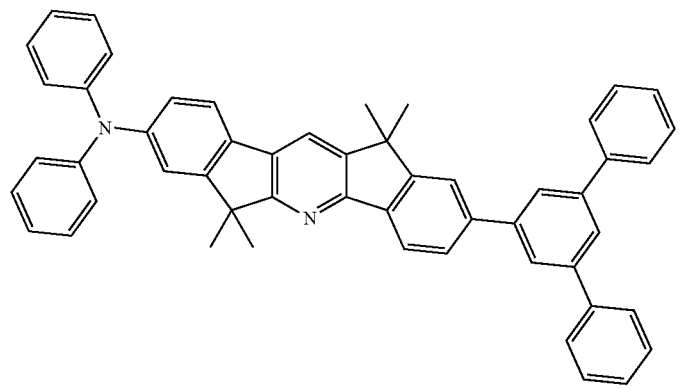
83
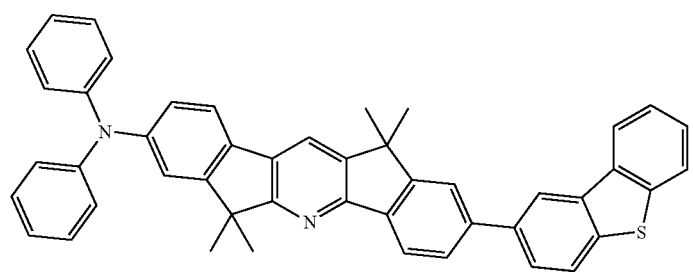
84
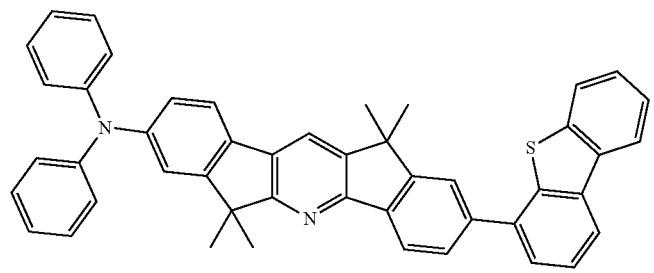
85
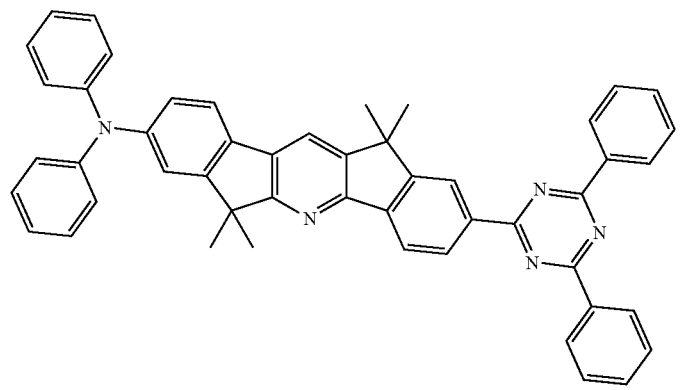

86
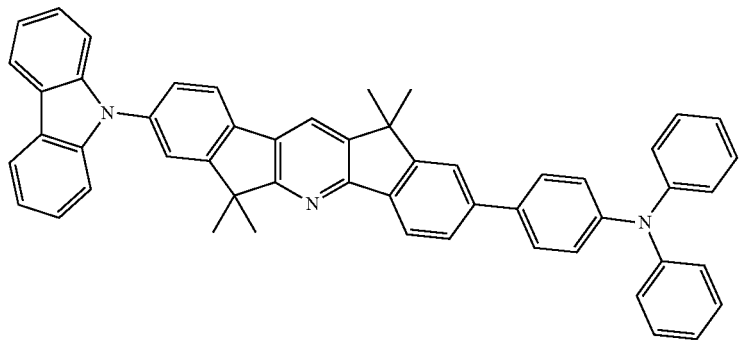
87
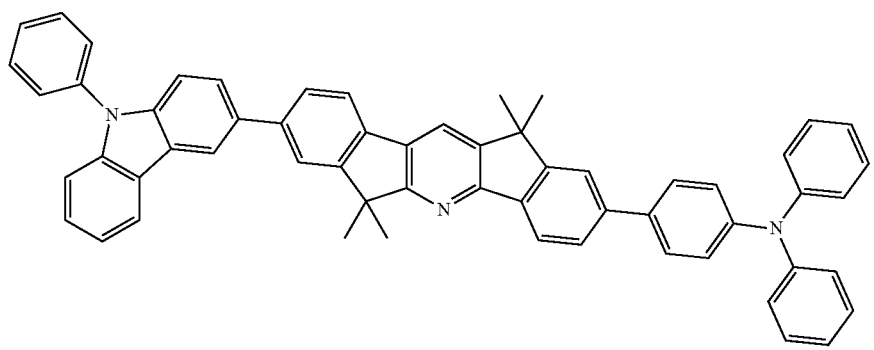
88
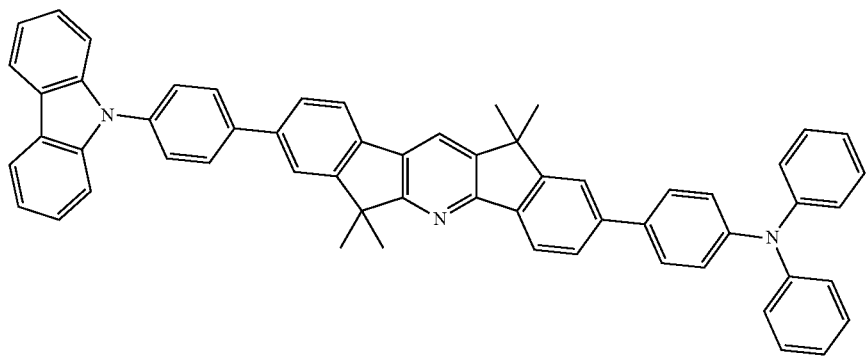
89
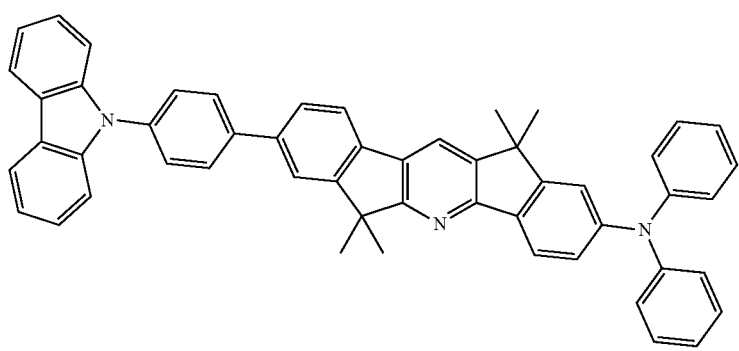

-continued

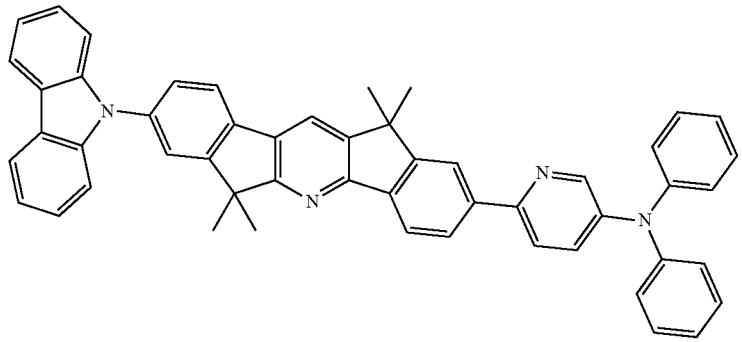

90

In some embodiments, the compound represented by Formula 1 may include a diindenopyrazine ring or a diindenopyridine ring. Accordingly, the compound may be suitable for manufacturing an organic light-emitting diode (OLED) emitting a short wavelength of light, and may provide an OLED with high color purity. Also, a heteroaryl structure including nitrogen in its skeleton may have, in addition to hole mobility of conventional amine derivatives, electron mobility. Accordingly, such a heteroaryl structure may provide excellent holes and electron injection or transportation characteristics. Due to such characteristics, a manufactured OLED may have a lower driving voltage and a higher luminescent efficiency.

In some embodiments, the compound represented by Formula 1 contains a heteroaryl ring (for example, diindenopyridine ring or diindenopyrazine ring) linked to an amine group. In some embodiments, a compound including a nitrogen-containing heteroaryl ring may allow electrons to move easily compared to a compound containing an aryl ring. Also, a compound containing an arylamine group may allow holes to move easily. Accordingly, the compound containing a nitrogen-containing heteroaryl ring and an aryl amine group may allow electrons and holes to move easily. Accordingly, excitons are easily formed in an emission layer, and thus, a manufactured OLED may have a lower driving voltage and higher efficiency.

Also, a compound having an asymmetric structure to a heteroaryl ring may have a three-dimensional steric structure compared to a compound having a symmetric structure thereto. Accordingly, since compounds having such an asymmetric structure are not packed, an OLED using such compounds may embody high-purity blue light. Due to introduction of different substituents to opposite sides of the heteroaryl ring, compounds with various properties may be provided. From among such compounds, a compound with high efficiency and long lifespan characteristics may be used.

In some embodiments, the compound represented by Formula 1 may be synthesized by using a known organic synthesis method.

In some embodiments, at least one of the compounds represented by Formula 1 may be used between a pair of electrodes of an OLED. For example, at least one of a compound of Formula 1 may be used in an emission layer, but an embodiment of the present invention is not limited thereto.

In some embodiments, the emission layer may further include a host, and the compound of Formula 1 may act as a dopant, but an embodiment of the present invention is not limited thereto.

In some embodiments, the host and the compound of Formula 1 may be co-deposited, but is not limited thereto.

Accordingly, provided is an OLED including: a substrate, a first electrode; a second electrode facing the first electrode; and an organic layer interposed between the first electrode and the second electrode and including an emission layer, wherein the organic layer includes at least one of a compound represented by Formula 1.

The wording that "(an organic layer) includes at least one compound of Formula 1" used herein means that "(an organic layer) may include one compound represented by Formula 1 or two or more compounds represented by Formula 1".

In some embodiments, the organic layer may include only Compound 1 as the compound of Formula 1. In this regard, Compound 1 may exist in an emission layer of the OLED. According to another embodiment of the present disclosure, the organic layer may include Compound 1 and Compound 2 as the compound of Formula 1. In this regard, Compound 1 and Compound 2 may exist in an identical layer (for example, emission layer).

In some embodiments, the organic layer may include a hole transportation region that is disposed between the first electrode and the emission layer and that includes at least one of a hole injection layer (HIL), a hole transportation layer (HTL), a functional layer having a hole injection capability and a hole transport capability (hereinafter, referred to as a H-functional layer), a buffer layer, and an electron blocking layer, and an electron transportation region that is disposed between the emission layer and the second electrode and that includes at least one of a hole blocking layer (HBL), an electron transportation layer (ETL), and an electron injection layer (EIL).

The term "organic layer" used herein refers to a single layer and/or a plurality of layers disposed between a first electrode and a second electrode of an OLED.

The FIGURE is a schematic sectional view of an OLED 10 according to an embodiment of the present invention. Hereinafter, the structure of an OLED according to an embodiment of the present invention and a method of manufacturing an OLED according to an embodiment of the present invention will be described in connection with the FIGURE.

In some embodiments, substrate 11, which may be any substrate that is used in general OLEDs, may be a glass substrate or a transparent plastic substrate with excellent mechanical strength, thermal stability, transparency, surface smoothness, ease of handling, and water resistance.

In some embodiments, a first electrode 13 may be formed by depositing or sputtering a material for a first electrode on the substrate 11. When the first electrode 13 is an anode, the material for the first electrode may be selected from materials with a high work function to enable ease of hole injection. In some embodiments, the first electrode 13 may be a reflective electrode or a transmission electrode. The material for the first electrode may be a transparent material with high conductivity, and examples of such a material are indium tin oxide (ITO), indium zinc oxide (IZO), tin oxide ($SnO_2$), and zinc oxide (ZnO). When magnesium (Mg), aluminum (Al), aluminum-lithium (Al—Li), calcium (Ca), magnesium-indium (Mg—In), magnesium-silver (Mg—Ag), or the like is used, the first electrode 13 may be used as a reflective electrode.

In some embodiments, the first electrode 13 may have a single-layer structure or a multi-layer structure including two or more layers. For example, the first electrode 13 may have a three-layered structure of ITO/Ag/ITO, but the structure of the first electrode 13 is not limited thereto.

In some embodiments, an organic layer 15 may be disposed on the first electrode 13.

In some embodiments, the organic layer 15 may include a HIL, a HTL, a H-functional layer, a buffer layer, an emission layer, an ETL, and an EIL.

In some embodiments, the HIL may be formed on the first electrode 13 by using various methods, such as vacuum deposition, spin coating, casting, Langmuir-Blodgett (LB) deposition, or the like.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about 10-8 torr to about 10-3 torr, and a deposition rate of about 0.01 to about 100 Å/sec. However, the deposition conditions are not limited thereto.

When the HIL is formed using spin coating, the coating conditions may vary according to the compound that is used to form the HIL, and the desired structure and thermal properties of the HIL to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto.

For use as a hole injection material, a known hole injection material may be used, and such a known hole material may be, for example, N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methylphenylphenylamino) triphenylamine (m-MTDATA), N,N'-di(1-naphthyl)-N,N'-diphenylbenzidine (NPB), TDATA, 2-TNATA, polyaniline/dodecylbenzenesulfonic acid (pani/DBSA), poly(3,4-ethylenedioxythiophene)/poly(4-styrenesulfonate) (PEDOT/PSS), polyaniline/camphor sulfonicacid (pani/CSA), or (polyaniline)/poly(4-styrenesulfonate) (PANI/PSS), but is not limited thereto.

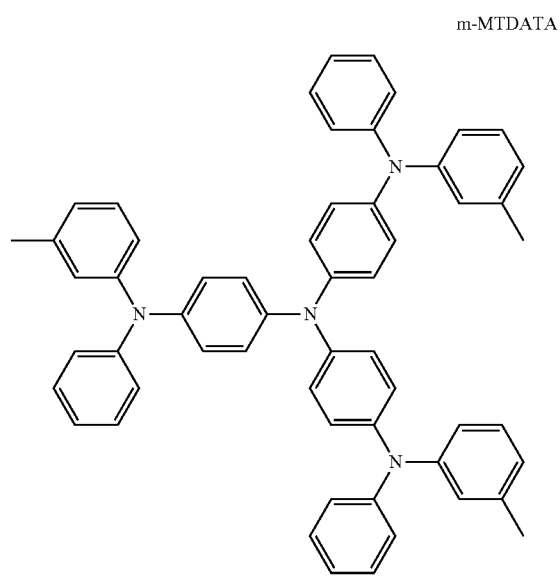

m-MTDATA

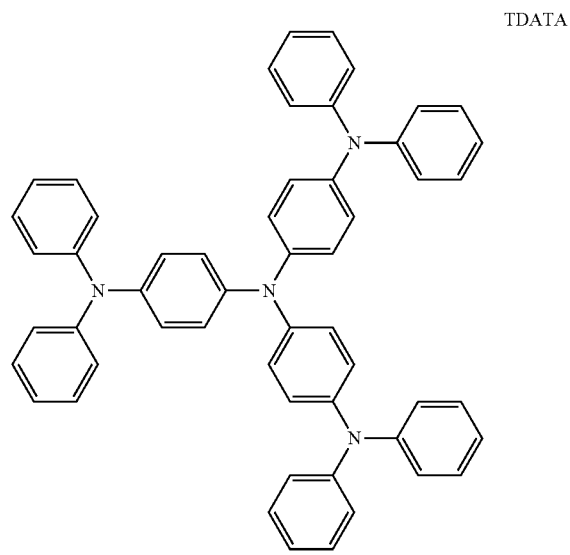

TDATA

2-TNATA

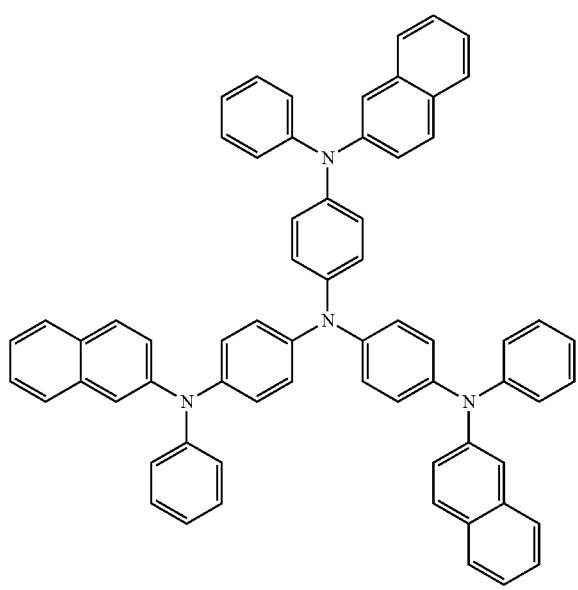

NPB

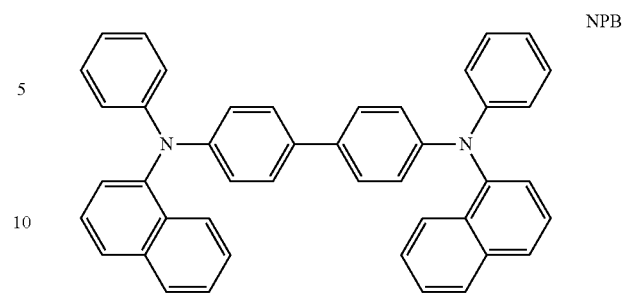

In some embodiments, a thickness of the HIL may be in a range of about 100 Å to about 10000 Å, for example, about 100 Å to about 1000 Å. When the thickness of the HIL is within these ranges, the HIL may have a satisfactory electron injection ability without a substantial increase in driving voltage.

Then, a HTL may be formed on the HIL by using vacuum deposition, spin coating, casting, LB deposition, or the like. When the HTL is formed using vacuum deposition or spin coating, the deposition and coating conditions may be similar to those for the formation of the HIL, though the deposition and coating conditions may vary according to a compound that is used to form the HTL.

Examples of a known hole transport material are a carbazole derivative, such as N-phenylcarbazole or polyvinylcarbazol, N,N'-bis(3-methylphenyl)-N,N'-diphenyl-[1,1-biphenyl]-4,4'-diamine (TPD), 4,4',4''-tris(N-carbazolyl)triphenylamine (TCTA), and N,N'-di(1-naphthyl)-N,N'-diphenylbenzidine (NPB), but are not limited thereto.

In some embodiments, a thickness of the HTL may be in a range of about 50 Å to about 2000 Å, for example, about 100 Å to about 1500 Å. When the thickness of the HTL is within these ranges, the HTL may have a satisfactory electron transporting ability without a substantial increase in driving voltage.

In some embodiments, a H-functional layer (a functional layer having a hole injection ability and a hole transport ability) may include one or more materials selected from the materials for the HIL and the materials for the HTL. In some embodiments, a thickness of the H-functional layer may be in a range of about 500 Å to about 10,000 Å, for example, about 100 Å to about 1,000 Å. When the thickness of the H-functional layer is within these ranges, the H-functional layer may have satisfactory hole injection and transport characteristics without a substantial increase in driving voltage.

In some embodiments, at least one of the HIL, the HTL, and the H-functional layer may further include a charge-generating material to increase conductivity of a layer, in addition to such known hole injecting materials, known hole transport materials, and/or materials having both hole injection and hole transport capabilities.

In some embodiments, the charge generating material may be one of quinine derivatives, metal oxides, and compounds with a cyano group, but is not limited thereto. Non-limiting examples of the charge generating material are a quinone derivative, such as tetracyanoquinonedimethane (TCNQ) or 2,3,5,6-tetrafluoro-tetracyano-1,4-benzoquinonedimethane (F4-TCNQ); a metal oxide, such as tungsten oxide or molybdenum oxide; and a cyano group-containing compound, such as Compound 200 below, but are not limited thereto.

TPD

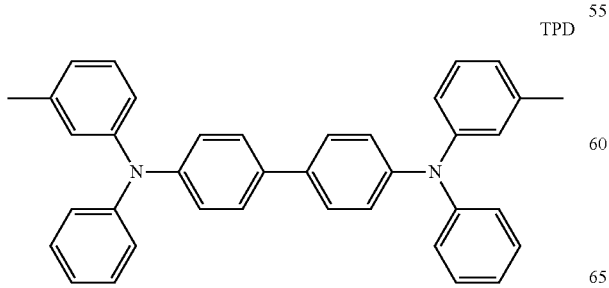

Compound 200

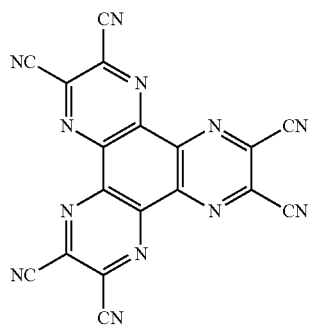

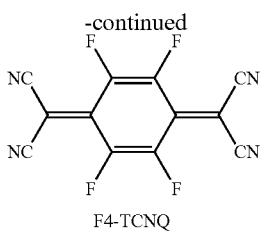

F4-TCNQ

When the HIL, the HTL, or the H-functional layer further includes a charge-generating material, the charge-generating material may be homogeneously dispersed or non-homogeneously distributed in the HIL, the HTL, and the H-functional layer.

In some embodiments, a buffer layer may be disposed between at least one of the HIL, the HTL, and the H-functional layer, and the emission layer. In some embodiments, the buffer layer may compensate for an optical resonance distance of light according to a wavelength of the light emitted from the emission layer, and thus may increase efficiency. In some embodiments, the buffer layer may include any hole injecting materials or hole transporting materials that are widely known. Also, the buffer layer may include a material that is the same as materials included in the HIL, the HTL, and the H-functional layer which are disposed under the buffer layer.

Subsequently, an emission layer (EML) may be formed on the HTL, the H-functional layer, or the buffer layer by spin coating, casting, or a LB method. When the EML is formed using vacuum deposition or spin coating, the deposition and coating conditions may be similar to those for the formation of the HIL, though the conditions for deposition and coating may vary according to the material that is used to form the EML.

In some embodiments, the EML may include a known luminescent material. For example, the EML may include a known host and a known dopant.

Examples of a known host are Alq$_3$, 4,4'-N,N'-dicarbazol-biphenyl(CBP), poly(n-vinylcarbazol)(PVK), 9,10-di(naphthalene-2-yl)anthracene (DNA), TCTA, 1,3,5-tris(N-phenyl-benzimidazole-2-yl)benzene (TPBI), 2-methyl-9,10-di-naphthalene-2-yl-anthracene(MADN), 3-tert-butyl-9,10-di (naphth-2-yl)anthracene (TBADN), mCP, and OXD-7, but are not limited thereto.

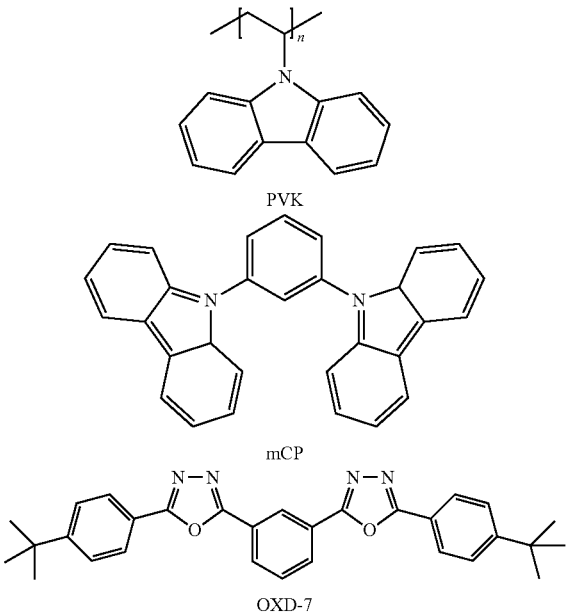

In some embodiments, the dopant may be at least one of a fluorescent dopant and a phosphorescent dopant. The phosphorescent dopant may be an organic metallic complex including Ir, Pt, Os, Re, Ti, Zr, Hf, or a combination of at least two of these, but is not limited thereto.

Examples of a known blue dopant are F$_2$Irpic, (F$_2$ppy)$_2$Ir (tmd), Ir(dfppz)$_3$, ter-fluorene, 4,4'-bis(4-diphenylaminos-tyryl)biphenyl (DPAVBi), 2,5,8,11-tetra-tert-butyl perylene (TBPe), and DPVBi, but are not limited thereto.

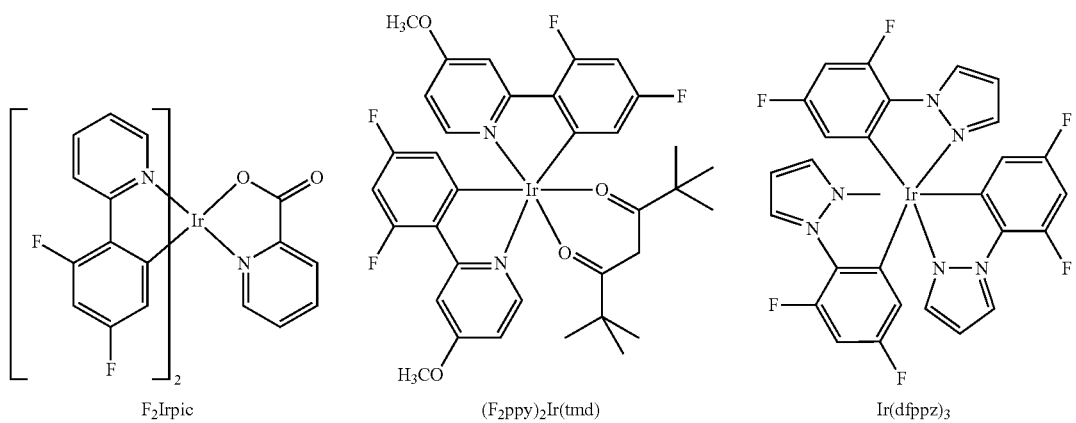

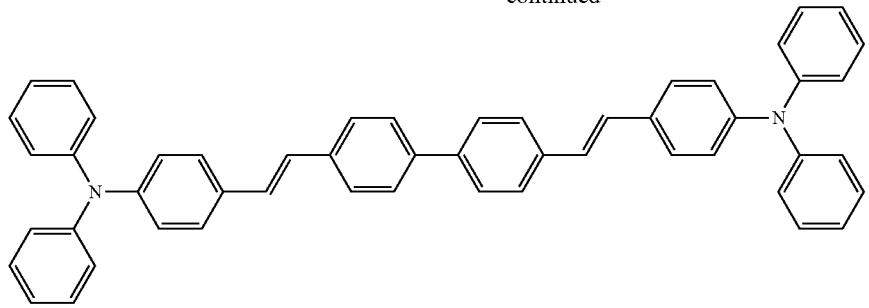
DPAVBi
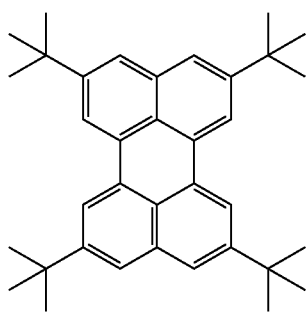
TBPe
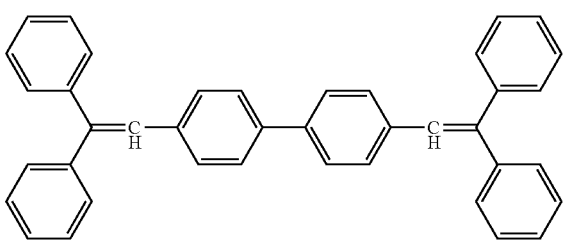
DPVBi
Examples of a known red dopant are PtOEP, Ir(piq)$_3$, and BtpIr, but are not limited thereto.
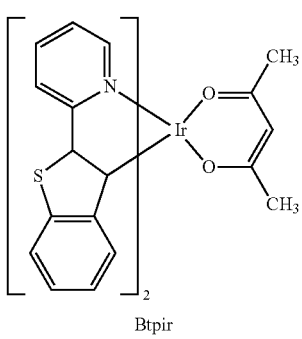
Btpir
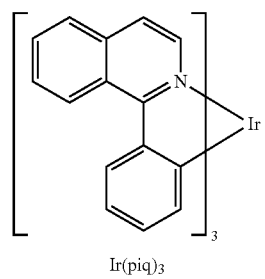
Ir(piq)$_3$
Examples of a known green dopant are Ir(ppy)$_3$ (ppy=phenylpyridine), Ir(ppy)$_2$(acac), and Ir(mpyp)$_3$, but are not limited thereto.
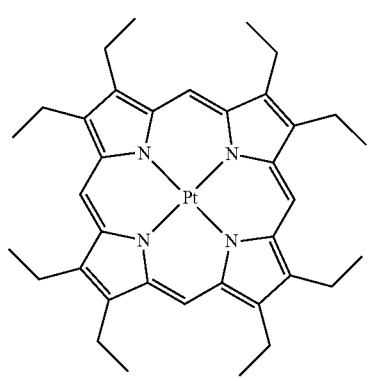
PtOEP
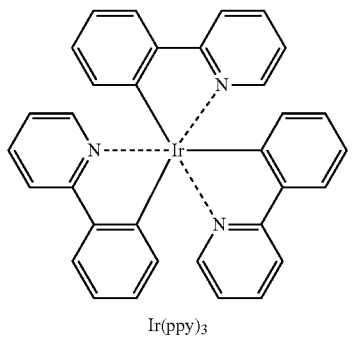
Ir(ppy)$_3$

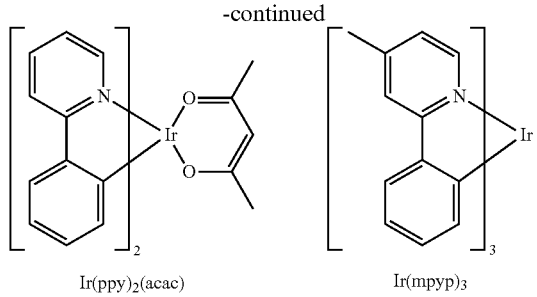

Ir(ppy)₂(acac)  Ir(mpyp)₃

When the EML includes a host and a dopant, an amount of the dopant may be, conventionally, in a range of about 0.01 to about 15 wt % based on 100 wt % of the EML, but the amount of the dopant is not limited thereto.

In some embodiments, a thickness of the EML may be in a range of about 200 Å to about 700 Å. When the thickness of the EML is within these ranges, the EML may have improved luminescent properties without a substantial increase in driving voltage.

Next, an ETL is formed on the EML by using various methods, for example, by vacuum deposition, spin coating, casting, or the like. When the ETL is formed using vacuum deposition or spin coating, the deposition and coating conditions may be similar to those for the formation of the HIL, though the conditions for deposition and coating may vary according to the material that is used to form the ETL. A material for an ETL may be any one of various known electron transporting materials that stably transport electrons injected from an electron injection electrode (cathode). Examples of a known electron transport material are a quinolin derivative, such as, tris(8-quinolinolate)aluminum (Alq₃), 3-(biphenyl-4-yl)-5-(4-tert-butylphenyl)-4-phenyl-4H-1,2,4-triazole (TAZ), aluminum (III) bis(2-methyl-8-quinolinato) 4-phenylphenolate (BAlq), beryllium bis(benzoquinoli-10-nolate) (Bebq₂), 9,10-di(2-naphthyl) anthracene (ADN), Compound 101, Compound 102, and 4,7-diphenyl-1,10-phenanthroline (Bphen), but is not limited thereto.

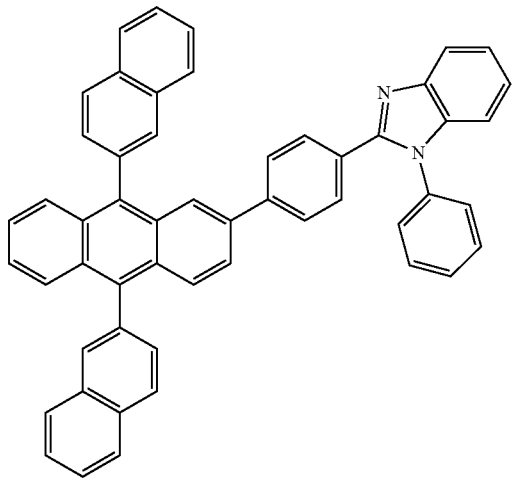

Compound 101

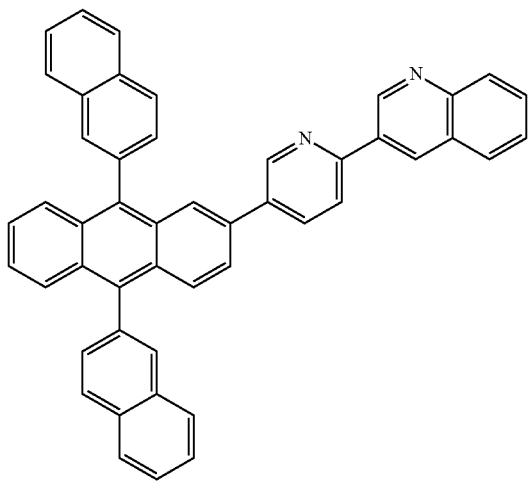

Compound 102

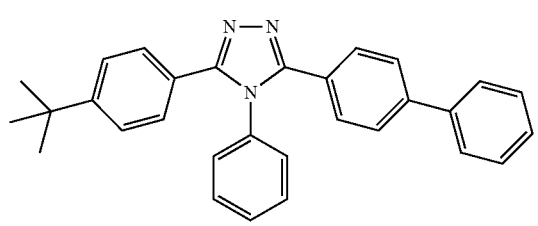

TAZ

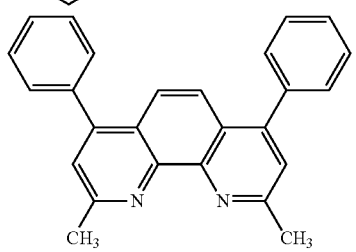

BCP

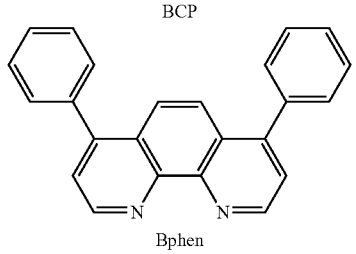

Bphen

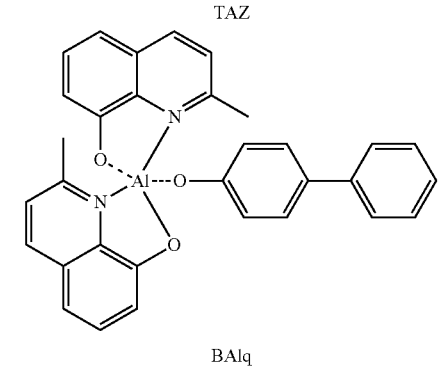

BAlq

In some embodiments, a thickness of the ETL may be in a range of about 100 Å to about 1000 Å, for example, about 150 Å to about 500 Å. When the thickness of the ETL is within these ranges, the ETL may have a satisfactory electron transporting ability without a substantial increase in driving voltage.

In some embodiments, the ETL may further include a metal-containing material, in addition to a known electron transporting inorganic material. In some embodiments, the metal-containing material may include a lithium (Li) complex. Non-limiting examples of the Li complex are lithium quinolate (Liq) and Compound 203 below:

Compound 203

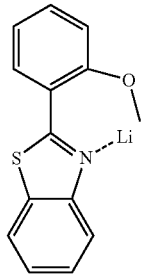

Then, an EIL, which facilitates injection of electrons from the cathode, may be formed on the ETL. Any suitable electron-injecting material may be used to form the EIL.

Non-limiting examples of materials for forming the EIL are LiF, NaCl, CsF, $Li_2O$, and BaO. In some embodiments, the deposition conditions of the EIL may be similar to those used to form the HIL, although the deposition conditions may vary according to the material that is used to form the EIL.

In some embodiments, the thickness of the EIL may be from about 1 Å to about 100 Å, and in some embodiments, may be from about 3 Å to about 90 Å. When the thickness of the EIL is within these ranges, the EIL may have a satisfactory electron injection ability without a substantial increase in driving voltage.

In some embodiments, a second electrode 17 is disposed on the organic layer 15. In some embodiments, the second electrode 17 may be a cathode, which is an electron injection electrode. In some embodiments, a metal for forming the second electrode may be a metal, an alloy, an electrically conductive compound, which all have a low-work function, or a mixture thereof. In some embodiments, lithium (Li), magnesium (Mg), aluminum (Al), aluminum (Al)-lithium (Li), calcium (Ca), magnesium (Mg)-indium (In), magnesium (Mg)-silver (Ag), or the like may be formed as a thin film to form a transmission electrode. In some embodiments, to manufacture a top-emission light-emitting diode, the transmission electrode may be formed of indium tin oxide (ITO) or indium zinc oxide (IZO).

In addition, when a phosphorescent dopant is used in the EML, a triplet exciton or a hole may diffuse to an ETL. To prevent this diffusion, a HBL may be formed between the HTL and the EML or between the H-functional layer and the EML by vacuum deposition, spin coating, casting, LB deposition, or the like. When the HBL is formed using vacuum deposition or spin coating, the deposition and coating conditions may be similar to those for the formation of the HIL, though the conditions for deposition and coating may vary according to the material that is used to form the HBL. Any known hole-blocking material may be used. Non-limiting examples of hole-blocking materials are oxadiazole derivatives, triazole derivatives, and phenanthroline derivatives. For example, bathocuproine (BCP) illustrated below may be used as a hole-blocking material.

In some embodiments, a thickness of the HBL may be in a range of about 20 Å to about 1000 Å, for example, about 30 Å to about 300 Å. When the thickness of the HBL is within these ranges, the HBL may have an improved hole blocking ability without a substantial increase in driving voltage.

Hereinbefore, an OLED according to an embodiment is described with reference to the FIGURE. However, the OLED is not limited thereto.

The unsubstituted $C_1$-$C_{60}$ alkyl group (or $C_1$-$C_{60}$ alkyl group) used herein may be a $C_1$-$C_{60}$ linear or branched alkyl group, such as methyl, ethyl, propyl, isobutyl, sec-butyl, pentyl, iso-amyl, or hexyl, and the substituted $C_1$-$C_{60}$ alkyl group may be prepared by substituting at least one hydrogen of the unsubstituted $C_1$-$C_{60}$ alkyl group with a substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group; a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof; a $C_3$-$C_{10}$ cycloalkyl group, a $C_3$-$C_{10}$ hetero cycloalkyl group, a $C_3$-$C_{10}$ cycloalkenyl group, a $C_3$-$C_{10}$ hetero cycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group; a $C_3$-$C_{10}$ cycloalkyl group, a $C_3$-$C_{10}$ hetero cycloalkyl group, a $C_3$-$C_{10}$ cycloalkenyl group, a $C_3$-$C_{10}$ hetero cycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group, each substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a fluorenyl group, dimethyla fluorenyl group, diphenyla fluorenyl group, carbazolyl, phenylcarbazolyl, a pyridyl group, a pyrimidyl group, a pyrazinyl group, a pyridazinyl group, a triazinyl group, a quinolyl group, and an isoquinolyl group; and —$N(Q_{11})(Q_{12})$; and —$Si(Q_{13})(Q_{14})(Q_{15})$ (herein, $Q_n$ and $Q_{12}$ are each independently a $C_6$-$C_{60}$ aryl group or a $C_2$-$C_{60}$ heteroaryl group, $Q_{13}$ to $Q_{15}$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group).

The unsubstituted $C_1$-$C_{60}$ alkoxy group (or $C_1$-$C_{60}$ alkoxy group) used herein has a formula of —OA (where A is the unsubstituted $C_1$-$C_{60}$ alkyl group described above), and detailed examples thereof are methoxy, ethoxy, and isopropyloxy, and at least one hydrogen atom of these alkoxy groups may be substituted with the same substituent as described above in connection with the substituted $C_1$-$C_{60}$ alkyl group.

The unsubstituted $C_2$-$C_{60}$ alkenyl group (or $C_2$-$C_{60}$ alkenyl group) used herein refers to an unsubstituted $C_2$-$C_{60}$ alkyl group having one or more carbon double bonds at a center or end thereof. Examples of the unsubstituted $C_2$-$C_{60}$ alkenyl group are ethenyl, prophenyl, and butenyl. At least one hydrogen atom of these unsubstituted $C_2$-$C_{60}$ alkenyl groups may be substituted with the same substituent as described above in connection with the substituted $C_1$-$C_{60}$ alkyl group.

The unsubstituted $C_2$-$C_{60}$ alkynyl group (or $C_2$-$C_{60}$ alkynyl group) used herein refers to an unsubstituted $C_2$-$C_{60}$ alkyl group having one or more carbon triple bonds at a center or end thereof. Examples of the unsubstituted $C_2$-$C_{60}$ alkynyl group are ethynyl, propynyl, and the like. At least one hydrogen atom of these alkynyl groups may be substituted with the same substituent as described above in connection with the substituted $C_1$-$C_{60}$ alkyl group.

The unsubstituted $C_3$-$C_{30}$ cycloalkyl group is a monovalent cyclic saturated hydrocarbonate group having 3 to 60 carbon atoms. Examples thereof are cyclopropyl, cyclobutyl, cyclopentyl, cyclohexyl, and cyclooctyl. At least one hydrogen atom of these cycloalkyl groups may be substituted with the same substituent as described above in connection with the substituted $C_1$-$C_{60}$ alkyl group.

The unsubstituted $C_3$-$C_{30}$ cycloalkenyl group refers to a cyclic unsaturated hydrocarbonate group that has one or more carbon double bonds and is not an aromatic cycle, and Examples thereof are cyclopropenyl, cyclobutenyl, cyclopentenyl, cyclohexenyl, cycloheptenyl, 1,3-cyclohexadienyl, 1,4-cyclohexadienyl, 2,4-cycloheptadienyl, and 1,5-cyclooctadienyl. At least one hydrogen atom of these cycloalkenyl groups may be substituted with the same substituent as described above in connection with the substituted $C_1$-$C_{60}$ alkyl group.

The unsubstituted $C_6$-$C_{60}$ aryl group used herein is a monovalent group having a carbocyclic aromatic system having 6 to 60 carbon atoms including at least one aromatic ring. The unsubstituted $C_6$-$C_{60}$ arylene group is a divalent group having a carbocyclic aromatic system having 6 to 60 carbon atoms including at least one aromatic ring. When the aryl group or the arylene group has at least two rings, they may be fused to each other via a single bond. At least one hydrogen atom of the aryl group or the arylene group may be substituted with the same substituent as described above in connection with the substituted $C_1$-$C_{60}$ alkyl group.

Examples of the substituted or unsubstituted $C_6$-$C_{60}$ aryl group are a phenyl group, a $C_1$-$C_{10}$ alkylphenyl group (for example, ethylphenyl group), a $C_1$-$C_{10}$ alkylbiphenyl group (for example, ethylbiphenyl group), a halophenyl group (for example, o-, m- and p-fluorophenyl groups, a dichlorophenyl group), a dicyanophenyl group, a trifluoromethoxyphenyl group, o-, m-, and p-tolyl groups, o-, m- and p-cumenyl groups, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (for example, a fluoronaphthyl group), a $C_1$-$C_{10}$ alkylnaphthyl group (for example, methyla naphthyl group), a $C_1$-$C_{10}$ alkoxynaphthyl group (for example, a methoxynaphthyl group), an anthracenyl group, an azrenyl group, a heptalenyl group, an acenaphthylenyl group, a phenalenyl group, a fluorenyl group, an anthraquinolinyl group, a methylan anthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentasenyl group, a tetraphenylenyl group, a hexaphenyl group, a hexacenyl group, a rubicenyl group, a coroneryl group, a trinaphthylenyl group, a heptaphenyl group, a heptacenyl group, a piranthrenyl group, and an obarenyl group, and examples of the substituted $C_6$-$C_{60}$ aryl group may be easily understood by referring to the examples of the unsubstituted $C_6$-$C_{60}$ aryl group and the substituents of the substituted $C_1$-$C_{60}$ alkyl group. Examples of the substituted or unsubstituted $C_6$-$C_{60}$ arylene group may be easily understood by referring to examples of the substituted or unsubstituted $C_6$-$C_{60}$ aryl group.

The unsubstituted $C_1$-$C_{60}$ heteroaryl group used herein refers to a monovalent group having a system composed of one or more aromatic rings having at least one hetero atom selected from nitrogen (N), oxygen (O), phosphorous (P), and sulfur (S) and carbon atoms as the remaining ring atoms. The unsubstituted $C_1$-$C_{60}$ heteroarylene group used herein refers to a divalent group having a system composed of one or more aromatic rings having at least one hetero atom selected from nitrogen (N), oxygen (O), phosphorous (P), and sulfur (S) and carbon atoms as the remaining ring atoms. When the heteroaryl group and the heteroarylene group have at least two rings, they may be fused to each other via a single bond. At least one hydrogen atom of the heteroaryl group and the heteroarylene group may be substituted with the same substituent described in connection with the $C_1$-$C_{60}$ alkyl group.

Examples of the unsubstituted $C_2$-$C_{60}$ heteroaryl group are a pyrazolyl group, an imidazolyl group, a oxazolyl group, a thiazolyl group, a triazolyl group, tetrazolyl, an oxadiazolyl group, a pyridinyl group, a pyridazinyl group, a pyrimidinyl group, a triazinyl group, a carbazolyl group, an indolyl group, a quinolinyl group, an isoquinolinyl group, a enzoanimidazolyl group, an imidazopyridinyl group, and an imidazopyrimidinyl group. Examples of the unsubstituted $C_2$-$C_{60}$ heteroarylene group may be easily understood by referring to the examples of the substituted or unsubstituted $C_2$-$C_{60}$ arylene group.

The substituted or unsubstituted $C_6$-$C_{60}$ aryloxy group is represented by —OA$_2$ (wherein, A$_2$ is the substituted or unsubstituted $C_6$-$C_{60}$ aryl group), and the substituted or unsubstituted $C_6$-$C_{60}$ arylthio group is represented by -SA$_3$ (wherein, A$_3$ is the substituted or unsubstituted $C_6$-$C_{60}$ aryl group).

Hereinafter, one or more embodiments of the present invention will be described in detail with reference to the following examples. These examples are not intended to limit the purpose and scope of the one or more embodiments of the present invention.

EXAMPLE

Synthesis Example 1

Synthesis of Compound 7

Intermediate A-1 was synthesized according to the following reaction scheme, which is a known method (Chem. Commun., 2008, pp. 2143-2145).

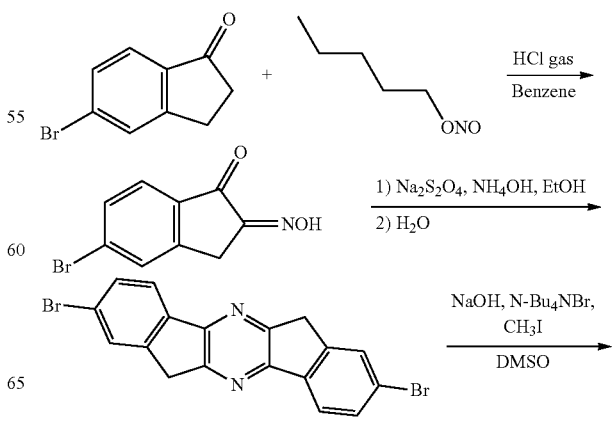

Synthesis of Intermediate 1A

Intermediate 1A was synthesized according to Reaction Scheme 1 below.

Reaction Scheme 1

Intermediate A-1 (4.70 g, 10.0 mmol), diphenylamine (1.52 g, 9.0 mmol), Pd$_2$(dba)$_3$ (0.45 g, 0.5 mmol), t-BuONa (1.15 g, 12 mmol), and (t-Bu)$_3$P (0.20 g, 1.0 mmol) were added to of toluene (100 mL) under a nitrogen atmosphere, and the resulting mixture was refluxed for 24 hours. When the reaction was completed, the solvent was removed therefrom by evaporation. Then, methylene chloride and water were separately added thereto to extract an organic layer, which was then dried by using anhydrous magnesium sulfate. Subsequently, the result was recrystallized to obtain Intermediate 1A (1.28 g, yield of 23%).

Synthesis of Compound 7

Compound 7 was synthesized according to Reaction Scheme 2 below.

Reaction Scheme 2

Intermediate 1A (1.28 g, 2.3 mmol), 4-(diphenylamino)phenylboronic acid (1.0 g, 3.5 mmol), Pd(PPh$_3$)$_4$ (0.14 g, 0.12 mmol), an aqueous solution of 2M K$_2$CO$_3$ (3 mL), toluene (10 mL) and ethanol (10 mL) were mixed, and then, the resulting mixture was refluxed and stirred for 24 hours. The result was washed with distilled water and then subjected to extraction with ethylacetate. An organic layer was dried with anhydrous MgSO$_4$, and a solvent was removed therefrom by evaporation. The result was purified by silica gel column chromatography to obtain Compound 7 (0.85 g, yield of 51%).

$^1$H-NMR (CDCl$_3$, 300 MHz, ppm): 7.9-7.8 (m, 2H), 7.5-7.4 (m, 3H), 7.2-7.1 (m, 9H), 6.8-6.5 (m, 16H), 1.7 (s, 12H).

MS (MALDI-TOF) m/z: 722 [M]$^+$.

Synthesis Example 2

Synthesis of Compound 36

Synthesis of Intermediate 2A

Reaction Scheme 3

83

-continued

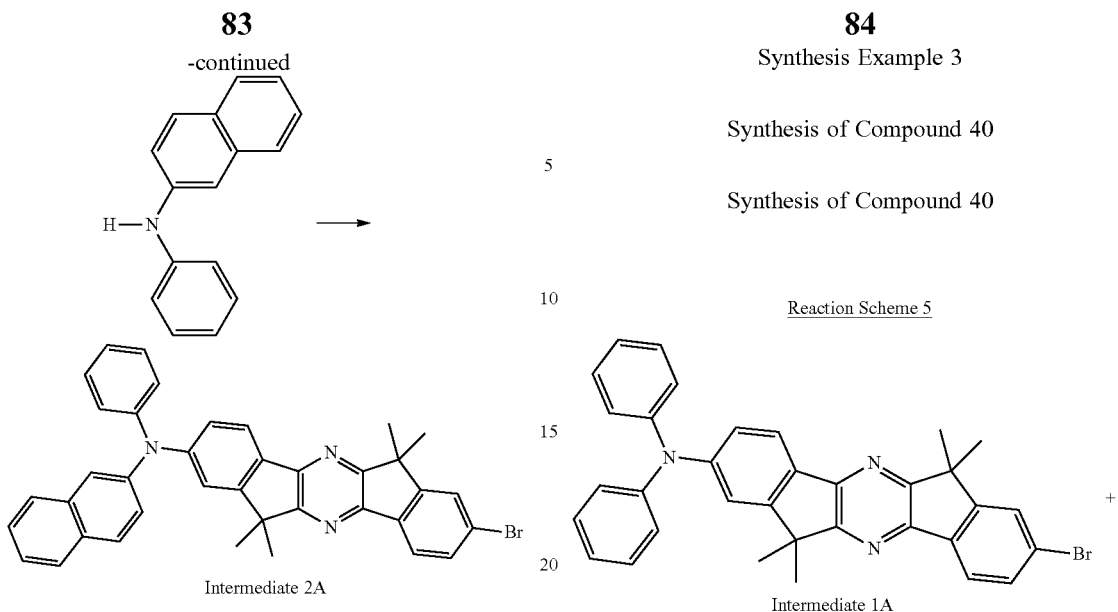

Intermediate 2A was synthesized in the same manner as used to synthesize Intermediate 1A, except that 2-naphthylphenylamine was used instead of diphenylamine.

Synthesis of Compound 36

Reaction Scheme 4

Compound 36 was synthesized in the same manner as used to synthesize Compound 7, except that Intermediate 2A was used instead of Intermediate 1A, and a 2-naphthylboronic acid was used instead of a 4-(diphenylamino)phenylboronic acid.

$^1$H-NMR (CDCl$_3$, 300 MHz, ppm): 8.0-7.9 (m, 6H), 7.8-7.7 (m, 4H), 7.6-7.4 (m, 7H), 7.2-7.1 (m, 3H), 6.8-6.5 (m, 5H), 1.7 (s, 12H).

MS (MALDI-TOF) m/z: 655 [M]$^+$.

84

Synthesis Example 3

Synthesis of Compound 40

Synthesis of Compound 40

Reaction Scheme 5

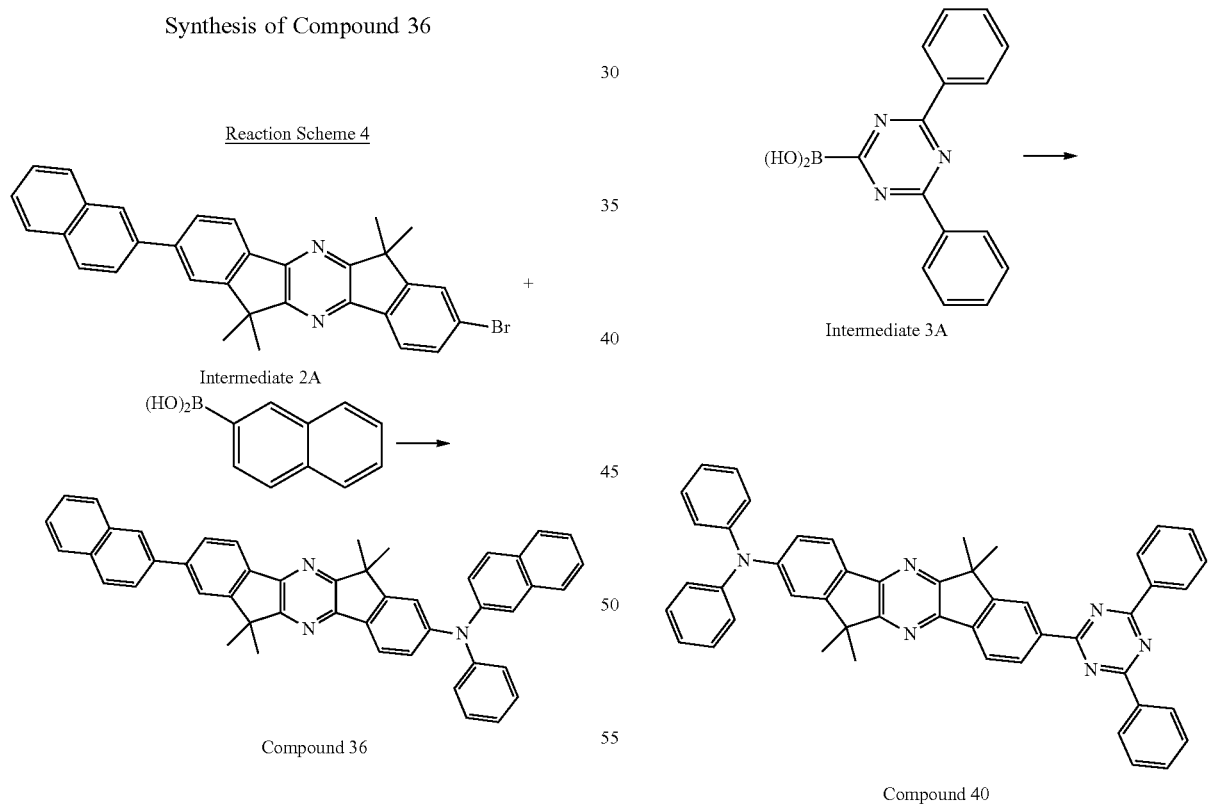

Compound 40 was synthesized in the same manner as used to synthesize Compound 7, except that Intermediate 3A was used instead of 4-(diphenylamino)phenylboronic acid.

$^1$H-NMR (CDCl$_3$, 300 MHz, ppm): 8.2-7.9 (m, 5H), 7.8-7.7 (m, 2H), 7.5-7.4 (m, 7H), 7.2-7.1 (m, 4H), 6.8-6.5 (m, 8H), 1.7 (s, 12H).

MS (MALDI-TOF) m/z: 710 [M]$^+$.

Synthesis Example 4

Synthesis of Compound 41

Synthesis of Intermediate 4A

Reaction Scheme 6

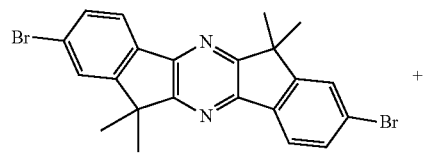

A-1

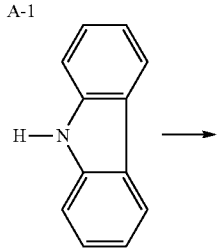

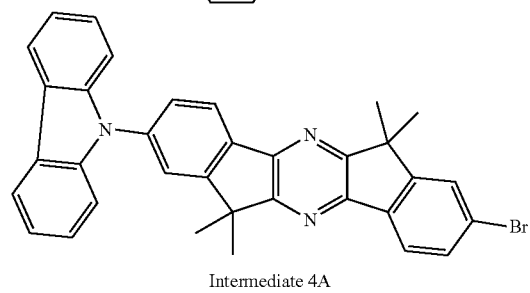

Intermediate 4A

Intermediate 4A was synthesized in the same manner as used to synthesize Intermediate 1A, except that carbazole was used instead of diphenylamine.

Synthesis of Compound 41

Reaction Scheme 7

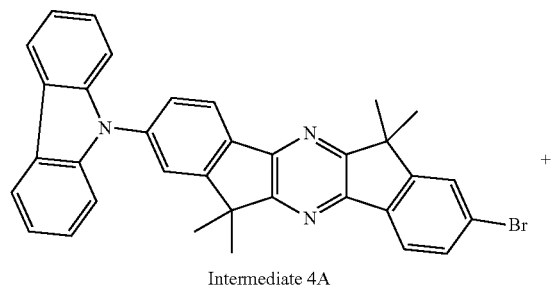

Intermediate 4A

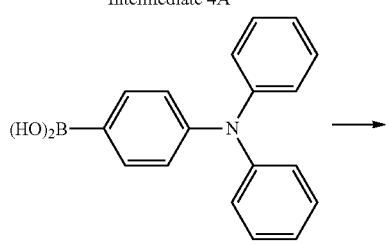

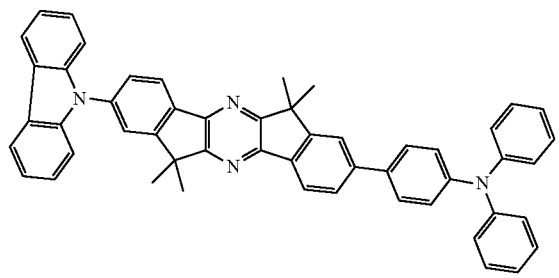

Compound 41

Compound 41 (36->41) was synthesized in the same manner as used to synthesize Compound 7, except that Intermediate 4A was used instead of Intermediate 1A.

$^1$H-NMR (CDCl$_3$, 300 MHz, ppm): 8.5 (d, 1H), 8.1 (d, 1H), 7.9-7.7 (m, 5H), 7.6-7.5 (m, 5H), 7.3-7.1 (m, 8H), 6.8-6.6 (m, 8H), 1.7 (s, 12H).

MS (MALDI-TOF) m/z: 720 [M]$^+$.

Synthesis Example 5

Synthesis of Compound 52

Reaction Scheme 8

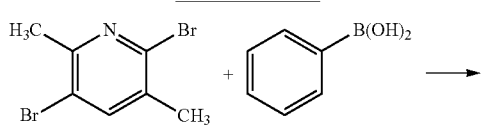

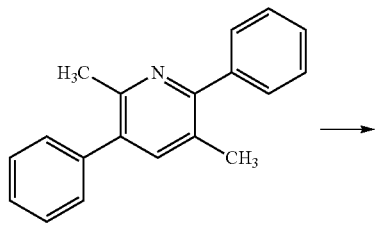

Intermediate 5A

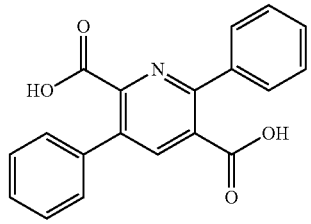

Intermediate 5B

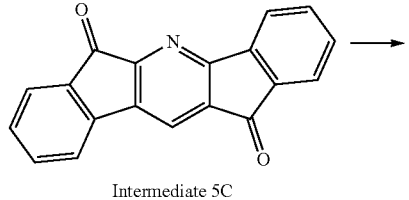

Intermediate 5C

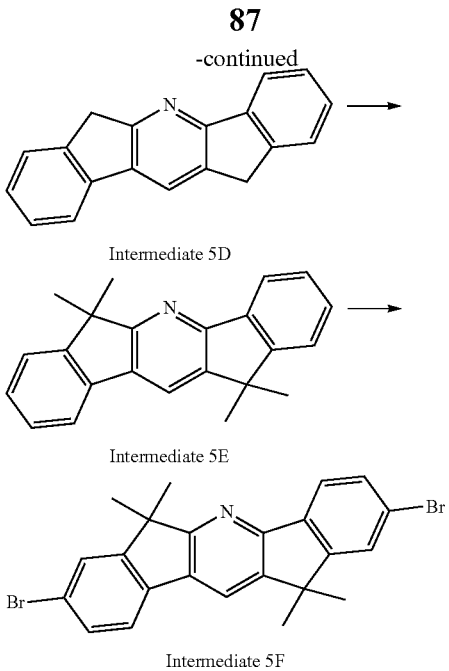

Intermediate 5D

Intermediate 5E

Intermediate 5F

Synthesis of Intermediate 5A

Intermediate 5A was synthesized in the same manner as used to synthesize Compound 7, except that 2,5-dibromo-3,6-dimethylpyridine was used instead of Intermediate 1A, and 3.0 eq. of a phenylboronic acid was used instead of a 4-(diphenylamino)phenylboronic acid.

Synthesis of Intermediate 5B

Intermediate 5A (2.60 g, 10.0 mmol), potassium permanganate (7.40 g), and water (5 mL) were added to pyridine (50 mL), and then, the resulting mixture was refluxed for 2 hours. Thereafter, every 30 minutes, water (10 mL) and potassium permanganate (3.00 g) were added thereto. After 6 additions, water (50 mL) was added thereto and the resultant mixture was refluxed for 12 hours. After the reaction was terminated, the formed $MnO_2$ precipitate was removed by using hot water, and then, the result was filtered with celite and activated carbon, and then strong HCl was added thereto and the generated solid was obtained by filtering, followed by drying in an oven to obtain Intermediate 5B (2.80 g, yield of 88%).

Synthesis of Intermediate 5C

Intermediate 5B (2.80 g, 8.8 mmol) was dissolved in 100 mL of $H_2SO_4$ and then, stirred at room temperature for 2 hours. When the reaction was terminated, the reaction product in a flask was placed in an iced bath, and then, the formed solid was neutralized by using an aqueous solution of potassium carbonate, and then, the solid was collected by filtering and then dried in an oven to obtain Intermediate 5C (1.82 g, yield of 73%).

Synthesis of Intermediate 5D

Intermediate 5C (1.82 g, 6.4 mmol) and 10 mL of hydrazine monohydrate (98%) were added to 150 mL of ethylenegylcol, and then 8.6 g of KOH was added thereto and the result was refluxed for 24 hours. A hot reaction solution was poured into an HCl solution to which ice had been added, and the formed solid was obtained by filtering. The obtained solid was recrystallized to obtain Intermediate 5D (1.47 g, yield of 90%).

Synthesis of Intermediate 5E

In a nitrogen atmosphere, Intermediate 5D (1.47 g, 5.76 mmol) was added to THF (200 mL) and then the mixture in a flask was cooled in an iced bath to a temperature of −78° C. n-BuLi (9.0 mL, 14.4 mmol, 1.6 M in Hex.) was slowly added thereto and then the result was stirred at a temperature of −78° C. for one hour. $CH_3I$ (1.08 mL, 17.3 mmol) was added thereto, and the temperature was slowly raised to room temperature, and then, the mixture was stirred for one hour. Then, the result was cooled to −78° C., and then n-BuLi (10.8 mL, 17.3 mmol, 1.6 M in Hex.) was slowly added thereto, and then, the mixture was stirred at a temperature of −78° C. for one hour. Finally, $CH_3I$ (1.25 mL, 20.1 mmol) was added thereto, and the temperature was increased to room temperature, and the mixture was stirred for one hour. When the reaction was terminated, the reaction solution was washed with distilled water, and then subjected to extraction with $CH_2Cl_2$, and then, dried with anhydrous $MgSO_4$, and distilled under reduced pressure. The obtained solid was placed into a flask, and then, hexane (200 mL) was added thereto, and the mixture was boiled while stirring. In this regard, materials that did not dissolve even when hexane was boiled were filtered and then dried well to obtain Intermediate 5E (1.18 g, yield of 66%).

Synthesis of Intermediate 5F

Intermediate 5E (1.18 g, 3.8 mmol) was loaded into a 30 mL round-bottom flask, and then vacuum-dried, and then the flask was filled with nitrogen gas. Subsequently, chloroform (10 mL) was added to the flask, and then, surrounded by a foil to prevent exposure to light. The flask was cooled to 0° C. and then $FeCl_3$ (10 mg, 58 μmol) was added thereto, and bromine (1.3 g, 8.0 mmol) dissolved in chloroform (3 mL) was added thereto for 30 minutes. The temperature was raised to room temperature, and then the result was stirred for 5 hours. When the reaction was terminated, the reaction mixture was poured into a saturated aqueous solution of sodium thiosulfate (15 mL). The mixture was stirred until red color disappeared, and then, subjected to extraction with chloroform and dried with anhydrous $MgSO_4$ and distilled under reduced pressure. The obtained material was placed into a flask, and then, hexane (200 mL) was added thereto, and the mixture was boiled while stirring. In this regard, materials that did not dissolve even when hexane was boiled were filtered and then dried well to obtain Intermediate 5E (1.52 g, yield of 85%).

Reaction Scheme 9

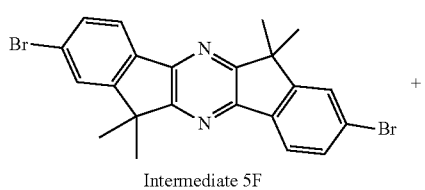

Intermediate 5F

89
-continued

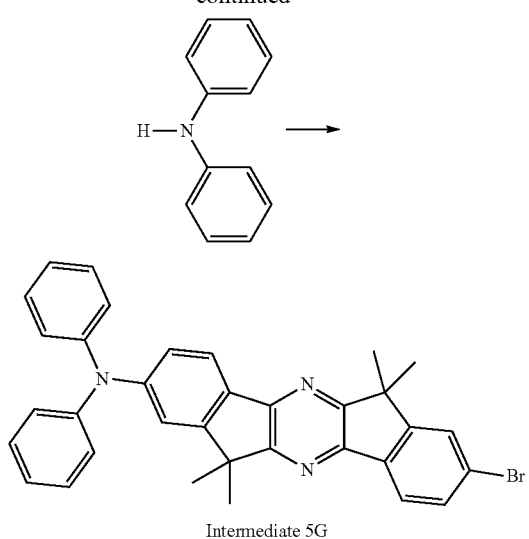

Intermediate 5G

Synthesis of Intermediate 5G

Intermediate 5G was synthesized in the same manner as used to synthesize Intermediate 1A, except that Intermediate 5F was used instead of Intermediate A-1.

<Reaction Scheme 10>

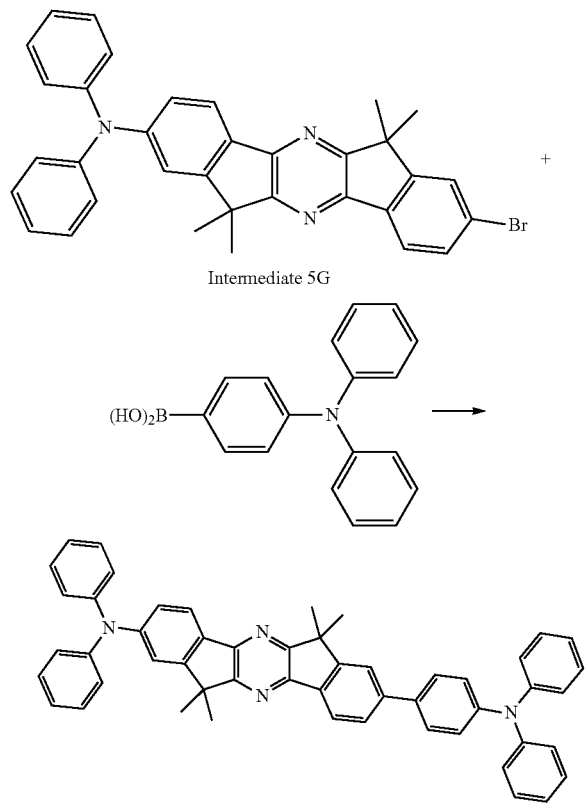

Compound 52

90
Synthesis of Compound 52

Compound 52 was synthesized in the same manner as used to synthesize Compound 7, except that Intermediate 5G was used instead of Intermediate 1A.

$^1$H-NMR (CDCl$_3$, 300 MHz, ppm): 8.0-7.8 (m, 3H), 7.6-7.5 (m, 3H), 7.2-7.1 (m, 9H), 6.8-6.5 (m, 16H), 1.7 (s, 12H).

MS (MALDI-TOF) m/z: 721 [M]$^+$.

Example 1

An anode was prepared by cutting a Corning 15Ω/cm$^2$ (1200 Å) ITO glass substrate to a size of 50 mm×50 mm×0.7 mm, ultrasonically cleaning the glass substrate using isopropyl alcohol and pure water for 5 minutes each, and then exposure to irradiation of UV light for 30 minutes and ozone to clean the ITO glass substrate. Then, the ITO glass substrate was loaded into a vacuum deposition apparatus.

m-MTDATA was vacuum deposited on the ITO glass substrate to form a HIL with a thickness of 300 Å. NPB was vacuum deposited on the HIL to form a HTL having a thickness of 300 Å.

2-methyl-9,10-di-naphthalene-2-yl-anthracene (MADN, host) and Compound 7 (dopant) were co-deposited on the HTL at a weight ratio of 95:5 to form an EML having a thickness of 200 Å.

Alq$_3$ was vacuum deposited on the EML to form an ETL having a thickness of 300 Å, and LiF was vacuum-deposited on the ETL to form an EIL having a thickness of 10 Å, and Al was vacuum deposited on the EIL to form a second electrode (cathode) having a thickness of 2000 Å, thereby completing the manufacturing of an OLED.

Example 2

An OLED was manufactured in the same manner as in Example 1, except that as a dopant material, Compound 36 was used instead of Compound 7.

Example 3

An OLED was manufactured in the same manner as in Example 1, except that as a dopant material, Compound 40 was used instead of Compound 7.

Example 4

An OLED was manufactured in the same manner as in Example 1, except that as a dopant material, Compound 41 was used instead of Compound 7.

Example 5

An OLED was manufactured in the same manner as in Example 1, except that as a dopant material, Compound 52 was used instead of Compound 7.

Comparative Example 1

An OLED was manufactured in the same manner as in Example 1, except that in forming the EML, Compound A was used instead of Compound 7.

Compound A

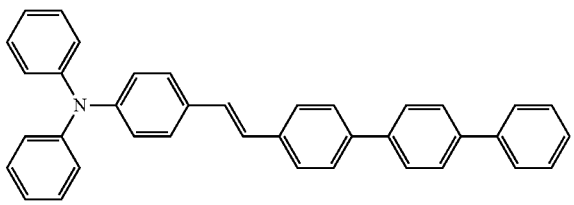

Comparative Example 2

An OLED was manufactured in the same manner as in Example 1, except that in forming the EML, Compound B was used instead of Compound 7.

Compound B

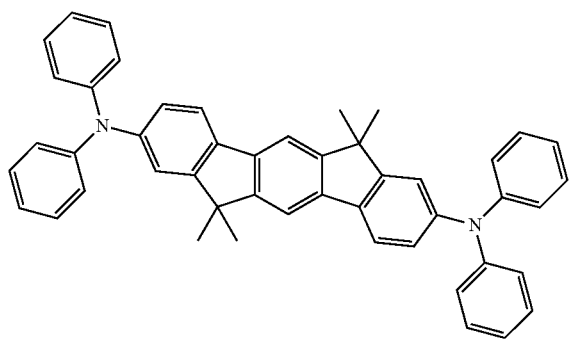

Comparative Example 3

An OLED was manufactured in the same manner as in Example 1, except that in forming the EML, Compound C was used instead of Compound 7.

Compound C

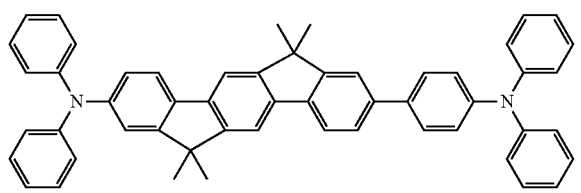

Evaluation Example 1

The driving voltage, current density, and color purity of the OLEDs manufactured according to Examples 1 to 5 and Comparative Examples 1 to 3 were measured by using Kethley SMU 236 and luminance meter PR650. Results thereof are shown in Table 1:

TABLE 1

| | Dopant | Driving voltage (V) | Efficiency (cd/A) | Color coordinate CIE | Half lifetime (hr @ 10 mA/cm$^2$) |
|---|---|---|---|---|---|
| Comparative Example 1: | Compound A | 5.7 | 2.8 | (0.15, 0.12) | 230 |
| Comparative Example 2: | Compound B | 5.4 | 3.4 | (0.14, 0.11) | 298 |
| Comparative Example 3: | Compound C | 5.2 | 3.3 | (0.15, 0.092) | 337 |
| Example 1 | Compound 7 | 4.7 | 3.8 | (0.15, 0.087) | 515 |
| Example 2 | Compound 36 | 4.2 | 3.7 | (0.15, 0.078) | 431 |
| Example 3 | Compound 40 | 4.3 | 3.3 | (0.15, 0.075) | 450 |
| Example 4 | Compound 41 | 4.2 | 3.7 | (0.15, 0.080) | 553 |
| Example 5 | Compound 52 | 4.4 | 3.5 | (0.15, 0.086) | 494 |

In general, in blue light-emitting OLEDs, when the y value of the color coordinate decreases, the manufactured diode may have a substantial decrease in lifespan and efficiency.

Referring to Table 1, the OLEDs manufactured according to Examples 1 to 5 had high efficiency and long lifespans, although the y value of the color coordinate is small. The OLEDs manufactured according to Examples 1 to 5 had the y value of the color coordinate as low as about 0.0075, and longer lifespans than those of Comparative Examples 1-3 by 30% to 200%.

That is, each of the OLEDs manufactured according to Examples 1 to 5 had a lower driving voltage, a higher efficiency, and a longer lifespan than the OLEDs manufactured according to Comparative Examples 1 to 3.

The compound of Formula 1 may be suitable for a blue light OLED, and provides high color purity. Also, the compound of Formula 1 may have excellent electron transport and hole transport characteristics. Accordingly, the heteroary-based compound may contribute to a decrease in driving voltage and an increase in luminescent efficiency of an OLED. Accordingly, an OLED manufactured by using the compound of Formula 1 may have high quality.

While the present embodiments have been particularly shown and described with reference to exemplary embodiments thereof, it will be understood by those of ordinary skill in the art that various changes in form and details may be made therein without departing from the spirit and scope of the present embodiments as defined by the following claims.

What is claimed is:
1. A compound represented by Formula 1 below:

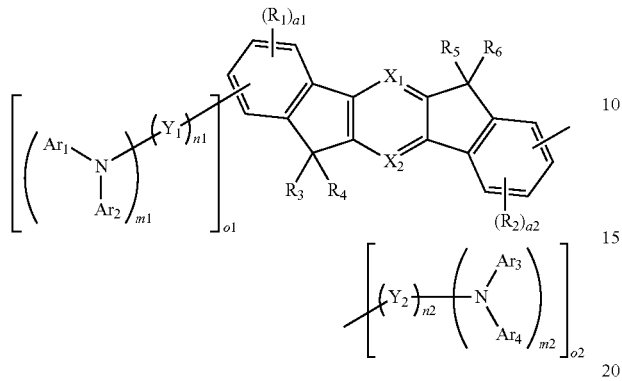

Formula 1 wherein, in Formula 1, $X_1$ is selected from $C(R_{11})$ and N (nitrogen), $X_2$ is selected from $C(R_{12})$ and N (nitrogen), provided that when $X_1$ is $C(R_{11})$ then $X_2$ is N (nitrogen), and when $X_2$ is $C(R_{12})$ then $X_1$ is N (nitrogen);

$Y_1$ and $Y_2$ are each independently selected from a substituted or unsubstituted $C_6$-$C_{30}$ arylene group and a substituted or unsubstituted $C_2$-$C_{30}$ heteroarylene group;

n1 is an integer of 0 to 5, n2 is an integer of 1 to 5, and when n1 is an integer of 2 or more, a plurality of $Y_1$ are identical to or different from each other, and when n2 is an integer of 2 or more, a plurality of $Y_2$ are identical to or different from each other;

$Ar_1$ to $Ar_4$ are each independently selected from a substituted or unsubstituted $C_6$-$C_{30}$ aryl group and a substituted or unsubstituted $C_2$-$C_{30}$ heteroaryl group;

$R_{11}$, $R_{12}$ and $R_1$ to $R_6$ are each independently selected from a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a substituted or unsubstituted $C_1$-$C_{30}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{30}$ aryl group, and a substituted or unsubstituted $C_2$-$C_{30}$ heteroaryl group;

m1 and m2 are each independently an integer of 1 or 2, and when m1 is 2, two of a moiety represented by

may be identical to or different from each other, and when m2 is 2, two of a moiety represented by

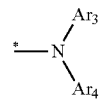

may be identical to or different from each other;

o1 is an integer of 0 to 5, o2 is an integer of 1 to 5, and when o1 is an integer of 2 or more, a plurality of moieties each represented by

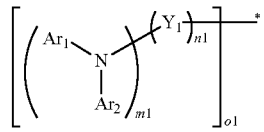

may be identical to or different from each other, and when o2 is an integer of 2 or more, a plurality of moieties each represented by

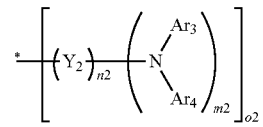

may be identical to or different from each other, provided that o1 and o2 are not 0 at the same time;

a1 and a2 are each independently an integer of 0 to 4, and when a1 is an integer of 2 or more, a plurality of $R_1$ are identical to or different from each other; and when a2 is an integer of 2 or more, a plurality of $R_2$ are identical to or different from each other.

2. The heteroaryl-based compound of claim 1, wherein $X_1$ is $C(R_{11})$ and $X_2$ is N (nitrogen), or $X_1$ is N (nitrogen) and $X_2$ is $C(R_{12})$.

3. The heteroaryl-based compound of claim 1, wherein $X_1$ and $X_2$ are both N (nitrogen).

4. The heteroaryl-based compound of claim 1, wherein $Y_1$ and $Y_2$ are each independently selected from phenylene, naphthylene, phenanthrenylene, pyridinylene, indolyl, carbazolyl, quinolinylene, thiophenylene and thienothiophenylene; and phenylene and carbazolyl, each substituted with at least one of a methyl group and a phenyl group.

5. The heteroaryl-based compound of claim 1, wherein n1 and n2 are each independently an integer of 1 or 2.

6. The heteroaryl-based compound of claim 1, wherein moieties represented by $(Y_1)_{n1}$ and $(Y_2)_{n2}$ are each independently one of Formulae 2a to 2q below:

2a

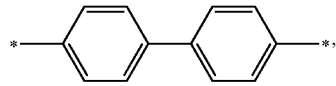

2b

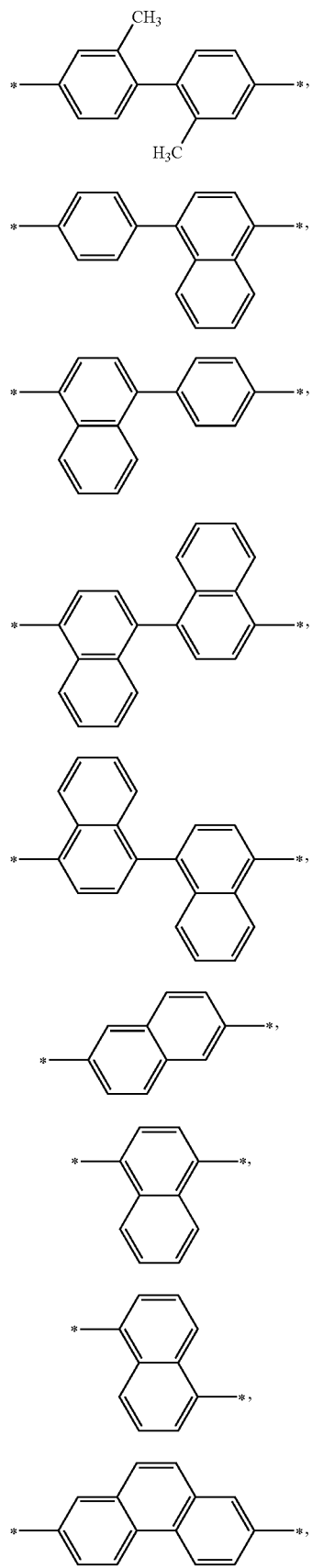

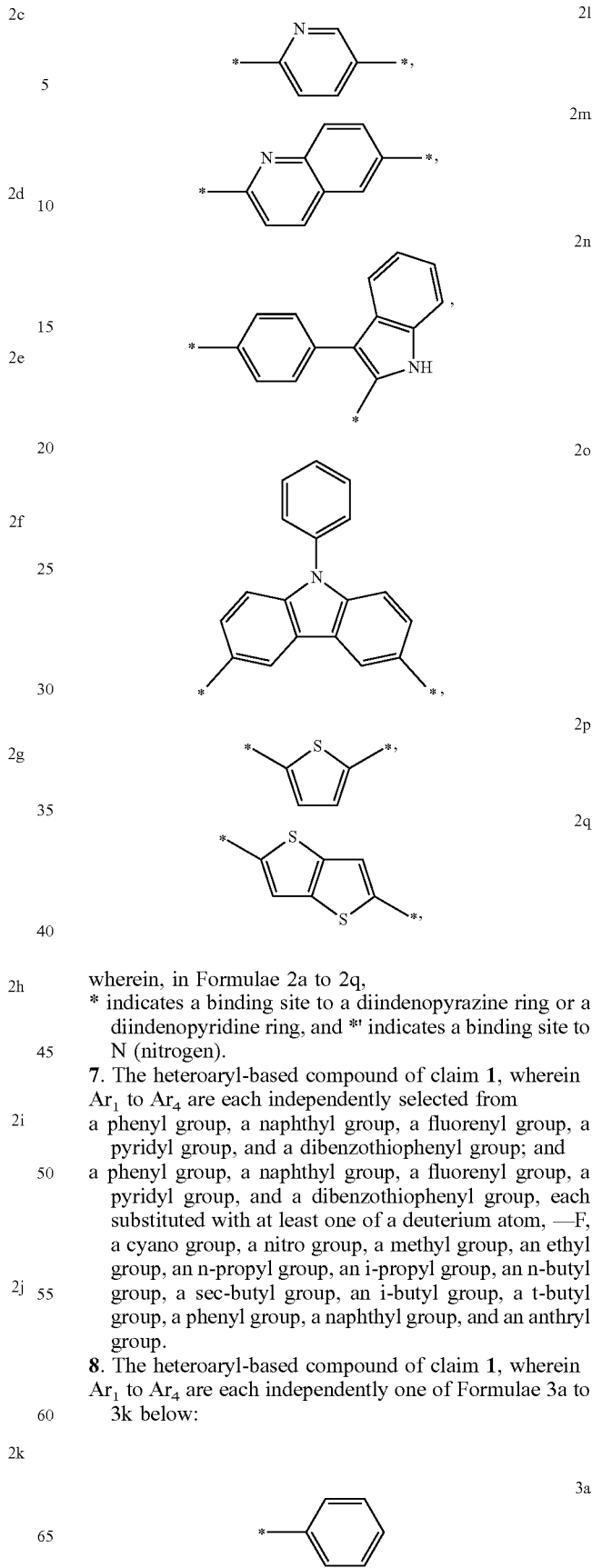

wherein, in Formulae 2a to 2q,
* indicates a binding site to a diindenopyrazine ring or a diindenopyridine ring, and *' indicates a binding site to N (nitrogen).

7. The heteroaryl-based compound of claim 1, wherein Ar₁ to Ar₄ are each independently selected from
   a phenyl group, a naphthyl group, a fluorenyl group, a pyridyl group, and a dibenzothiophenyl group; and
   a phenyl group, a naphthyl group, a fluorenyl group, a pyridyl group, and a dibenzothiophenyl group, each substituted with at least one of a deuterium atom, —F, a cyano group, a nitro group, a methyl group, an ethyl group, an n-propyl group, an i-propyl group, an n-butyl group, a sec-butyl group, an i-butyl group, a t-butyl group, a phenyl group, a naphthyl group, and an anthryl group.

8. The heteroaryl-based compound of claim 1, wherein Ar₁ to Ar₄ are each independently one of Formulae 3a to 3k below:

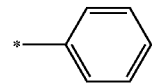

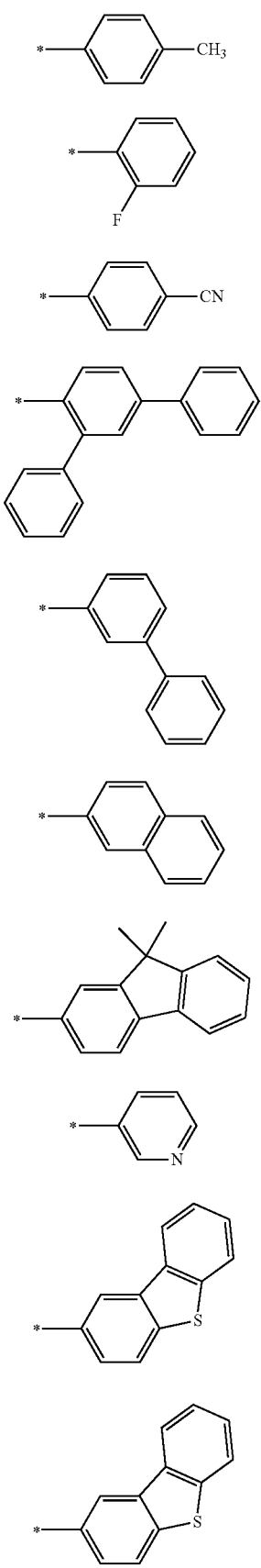

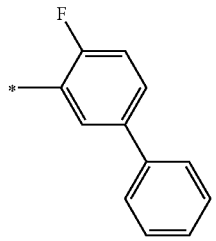

wherein, in Formulae 3a to 3k.

9. The heteroaryl-based compound of claim 1, wherein $R_{11}$ and $R_{12}$ are each independently selected from a hydrogen atom and a deuterium atom.

10. The heteroaryl-based compound of claim 1, wherein $R_1$ and $R_2$ are each independently selected from a hydrogen atom and a deuterium atom;
a phenyl group, a naphthyl group, a phenanthrenyl group, a triazinyl group, a carbazole group, an isoquinoline group and a dibenzothiophenyl group; and
a phenyl group, a naphthyl group, a phenanthrenyl group, a carbazole group, a triazinyl group, an isoquinoline group, and a dibenzothiophenyl group, each substituted with at least one of a phenyl group, a naphthyl group, an anthracenyl group and a carbazole group.

11. The heteroaryl-based compound of claim 1, wherein $R_3$ to $R_6$ are each independently selected from a methyl group and a phenyl group.

12. The heteroaryl-based compound of claim 1, wherein m1 and m2 are 1.

13. The heteroaryl-based compound of claim 1, wherein o1 and o2 are each independently 0 or 1, provided that o1 and o2 are not both 0.

14. The heteroaryl-based compound of claim 1, wherein the heteroaryl-based compound is represented by Formula 1a below:

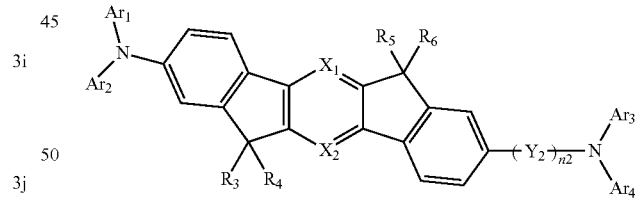

wherein, in Formula 1a,
a moiety represented by $(Y_2)_{n2}$ is one of Formulae 2a to 2q below;

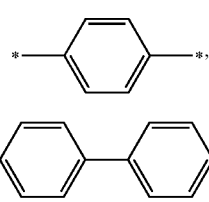

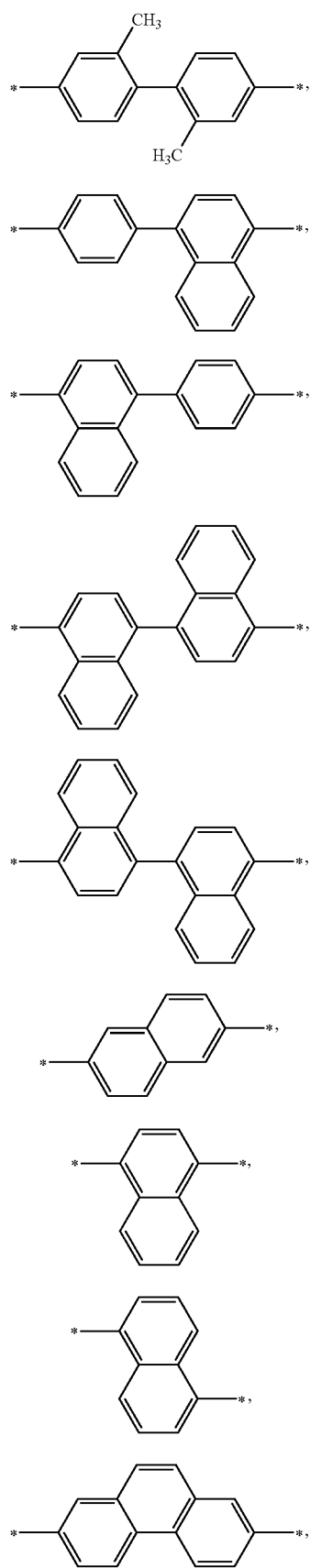
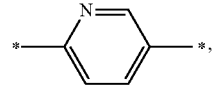
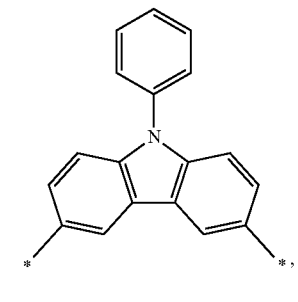
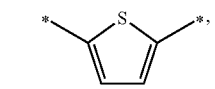
wherein, in Formulae 2a to 2q,
* indicates a binding site to a diindenopyrazin ring or a diindenopyridin ring, and *' indicates a binding site to N (nitrogen);
Ar$_1$ to Ar$_4$ are each independently one of Formulae 3a to 3k below;
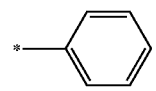
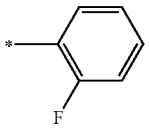

-continued

3d 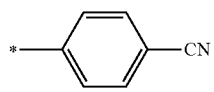

3e 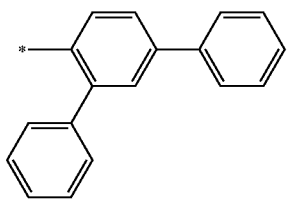

3f 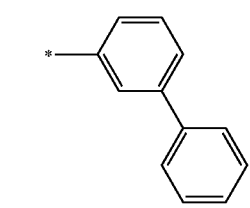

3g 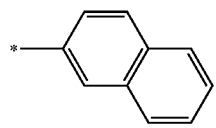

3h 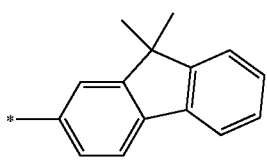

3i 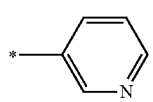

3j 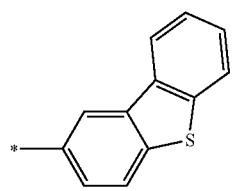

-continued

3k 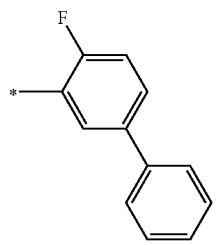

wherein, in Formulae 3a to 3k,
* is a binding site to N (nitrogen);
$R_{11}$ and $R_{12}$ are each independently selected from a hydrogen atom and a deuterium atom; and
$R_3$ to $R_6$ are each independently selected from a methyl group and a phenyl group.

15. A compound represented by Formula 1b below:

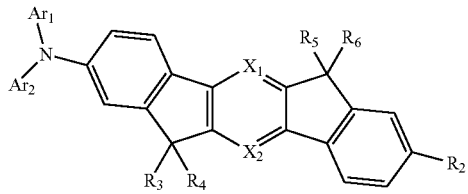

Formula 1b wherein, in Formula 1b,
$X_1$ is selected from $C(R_{11})$ and N (nitrogen), $X_2$ is selected from $C(R_{12})$ and N (nitrogen), provided that when $X_1$ is $C(R_{11})$ then $X_2$ is N (nitrogen), and when $X_2$ is $C(R_{12})$ then $X_1$ is N (nitrogen);
$Ar_1$ and $Ar_2$ are each independently selected from a substituted or unsubstituted $C_6$-$C_{30}$ aryl group and a substituted or unsubstituted $C_2$-$C_{30}$ heteroaryl group;
$R_{11}$, $R_{12}$, and $R_3$ to $R_6$ are each independently selected from a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a substituted or unsubstituted $C_1$-$C_{30}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{30}$ aryl group, and a substituted or unsubstituted $C_2$-$C_{30}$ heteroaryl group; and;
$R_2$ is each independently selected from a phenyl group, a naphthyl group, a phenanthrenyl group, a triazinyl group, an isoquinoline group, and a dibenzothiophenyl group; and
a phenyl group, a naphthyl group, a phenanthrenyl group, a triazinyl group, an isoquinoline group, and a dibenzothiophenyl group, each substituted with at least one of a phenyl group, a naphthyl group, an anthracenyl group, and a carbazol group.

16. The heteroaryl-based compound of claim 1, wherein the heteroaryl-based compound is one of Compounds 7 to 34, 41 to 43, 45, 52 to 79, 86 to 88, and 90 below:

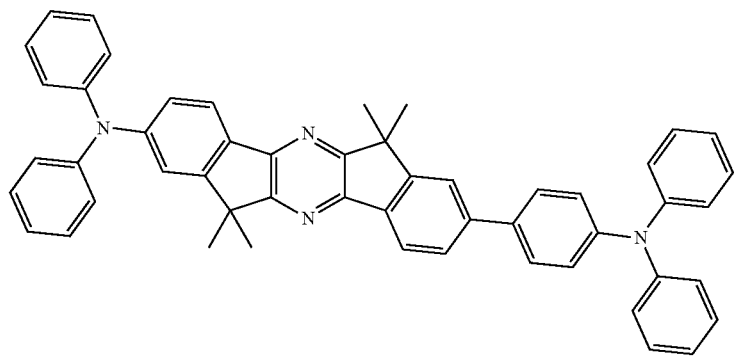
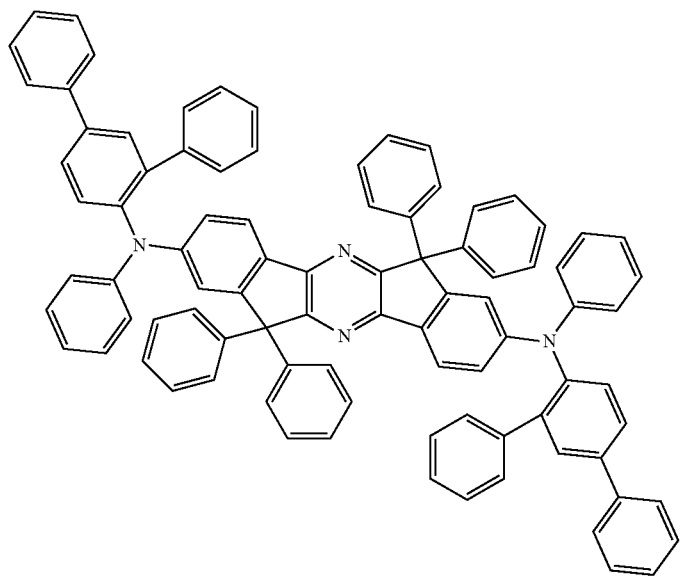
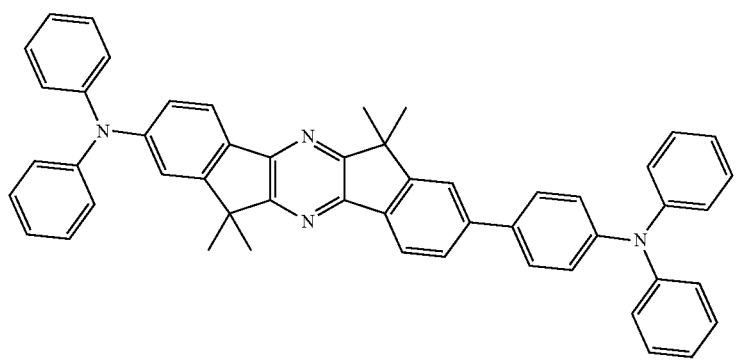

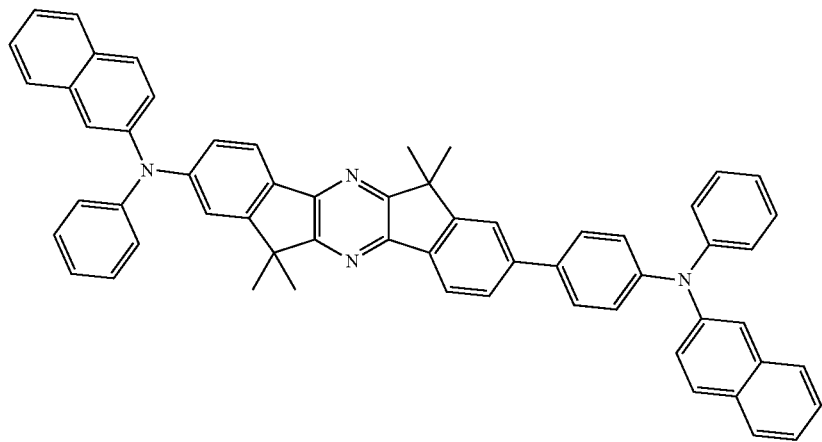
8
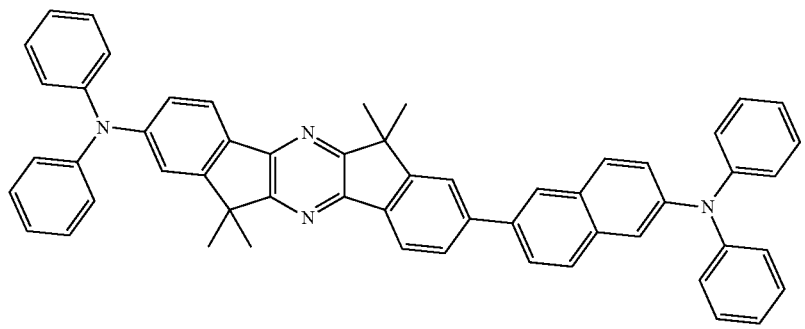
9
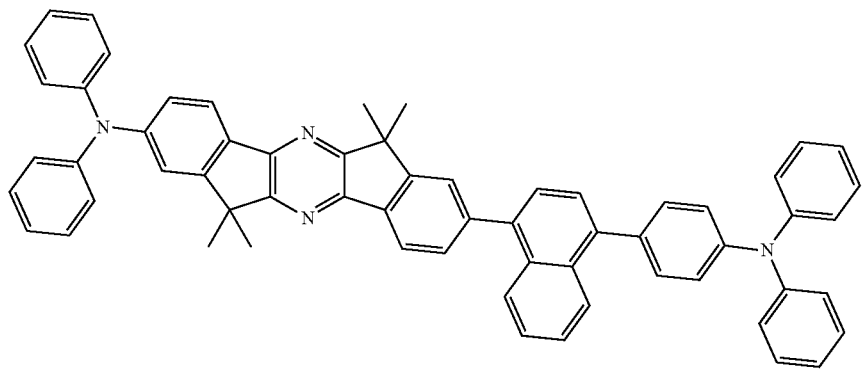
10
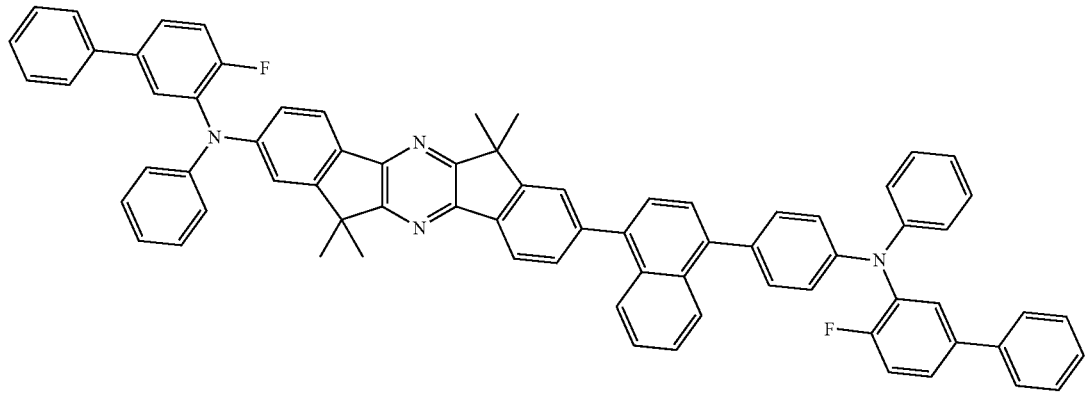
11

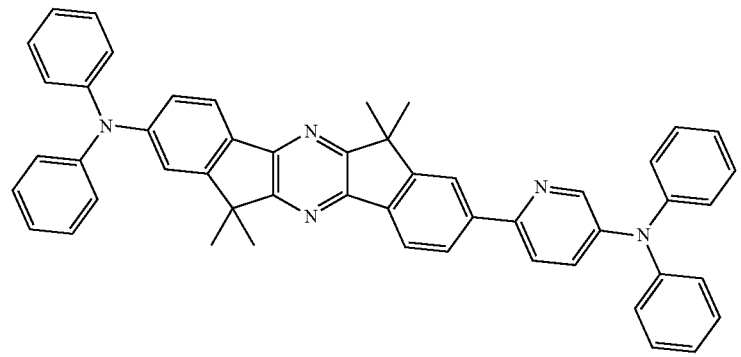
12
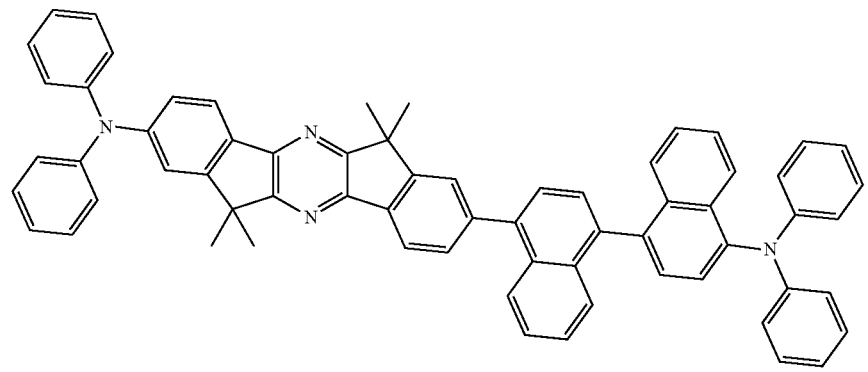
13
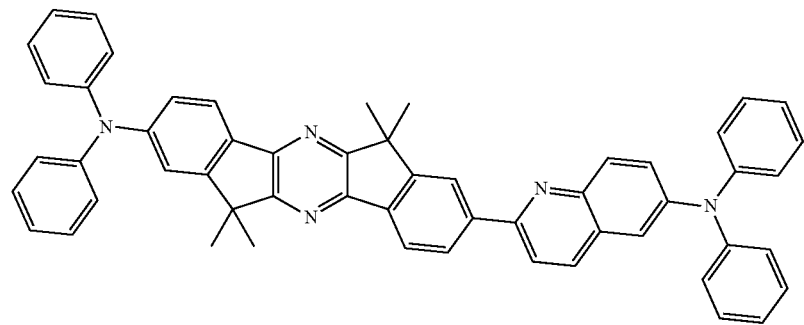
14
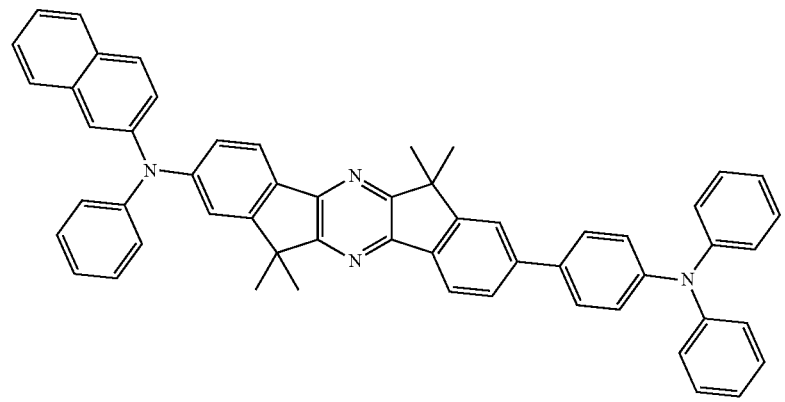
15

-continued
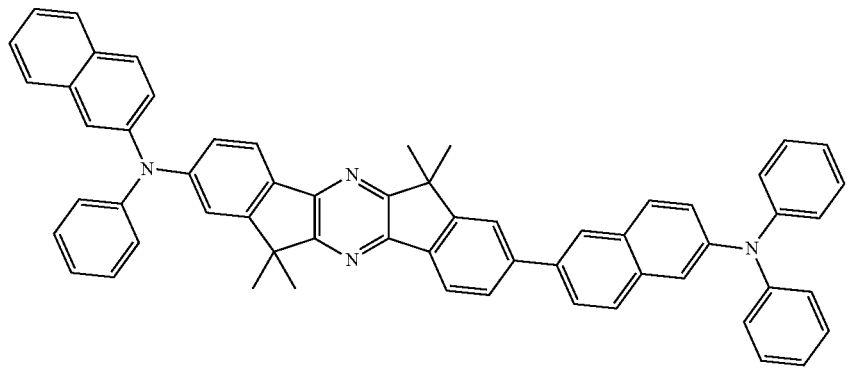
16
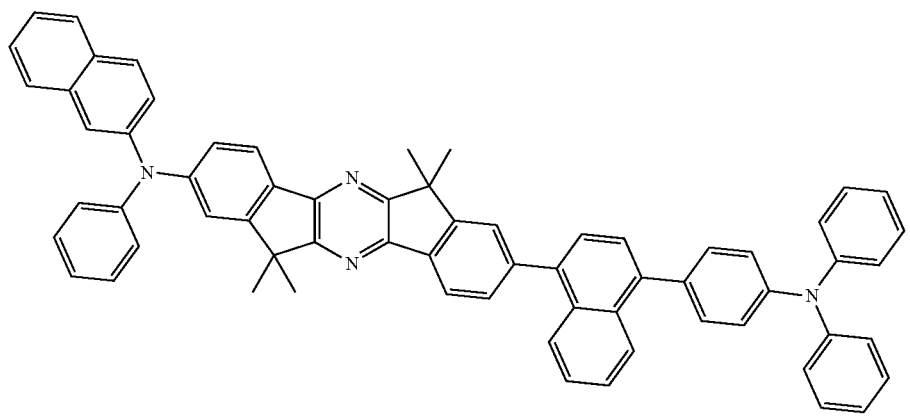
17
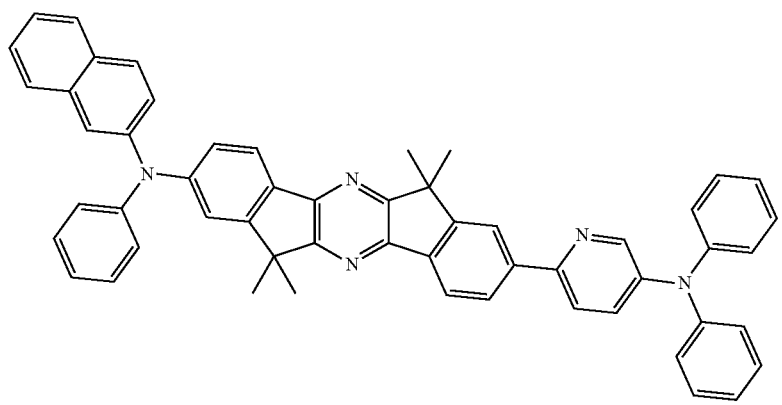
18
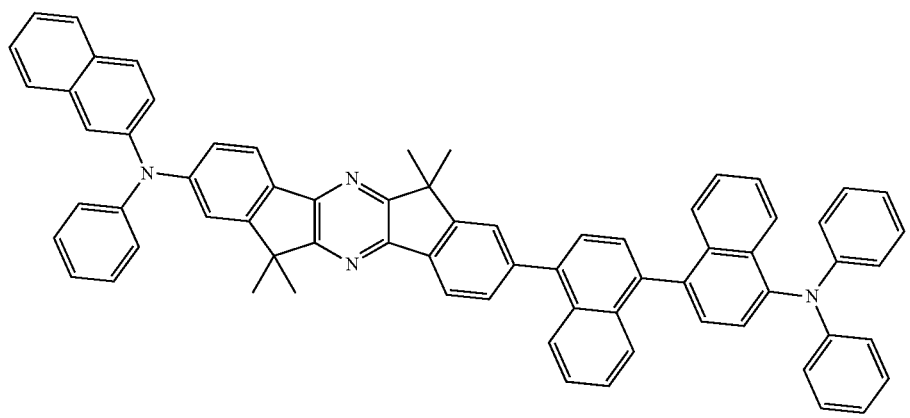
19

-continued
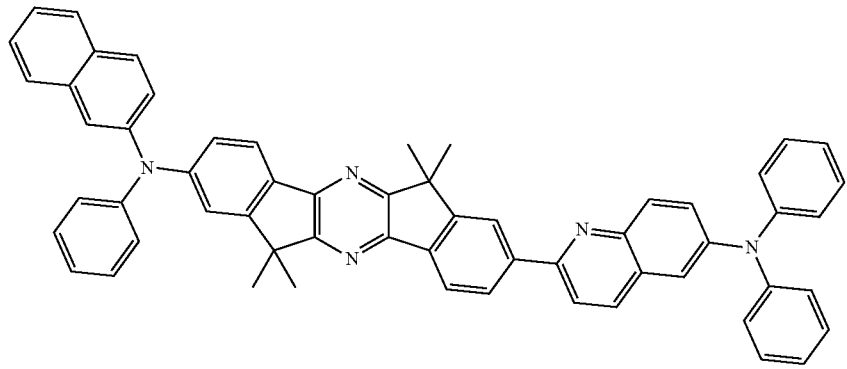
20
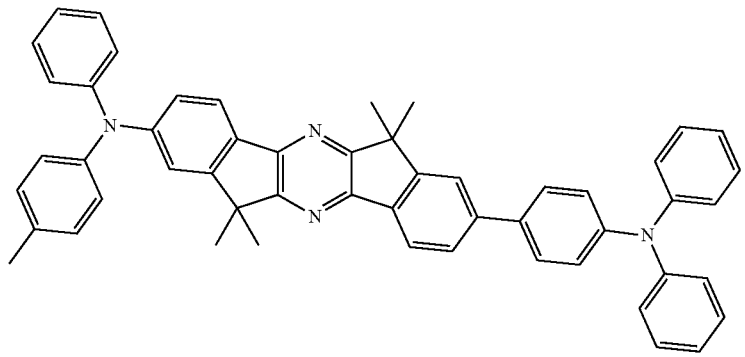
21
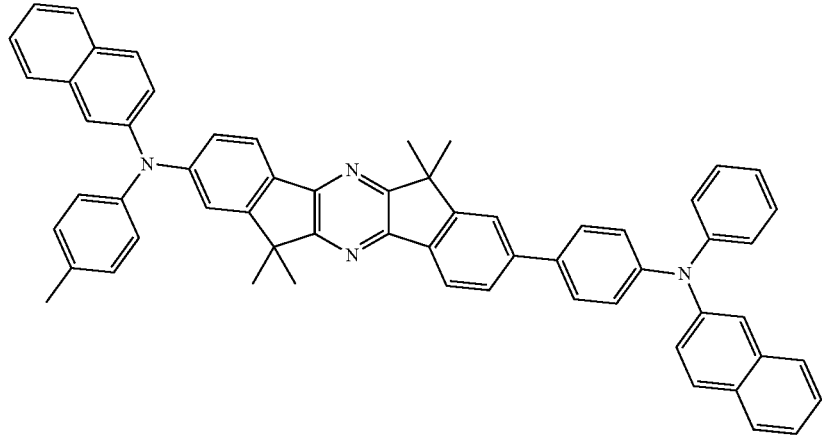
22
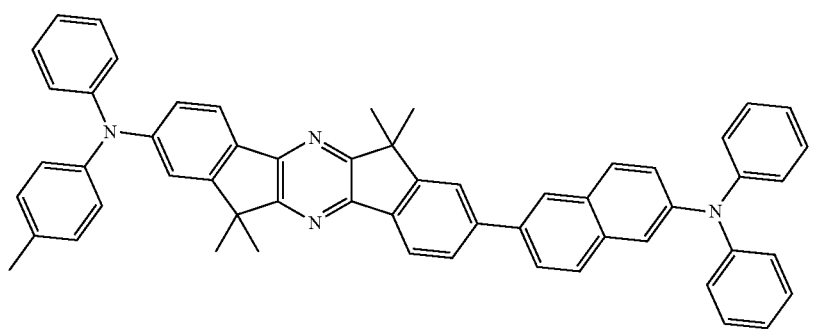
23

24
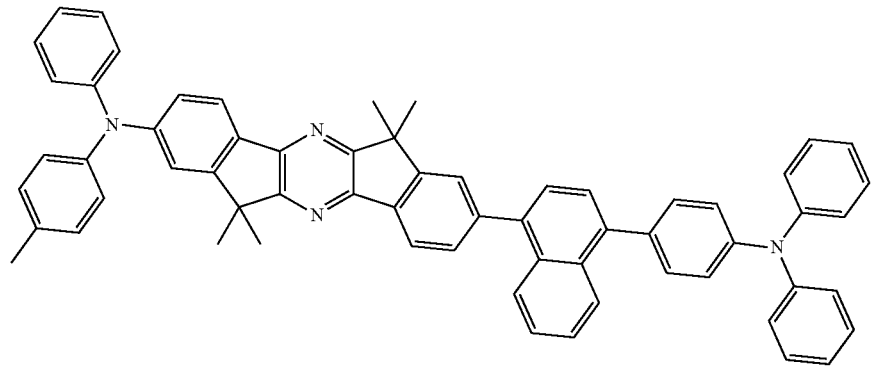
25
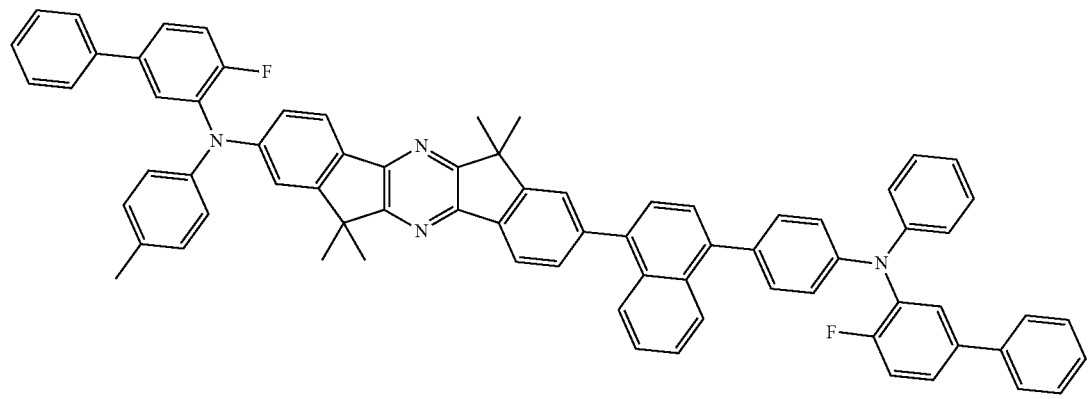
26
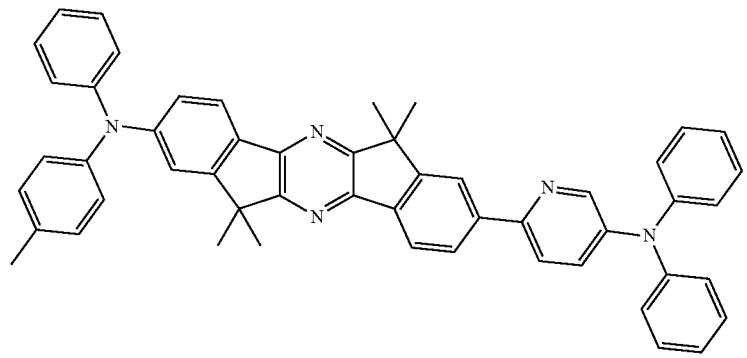
27
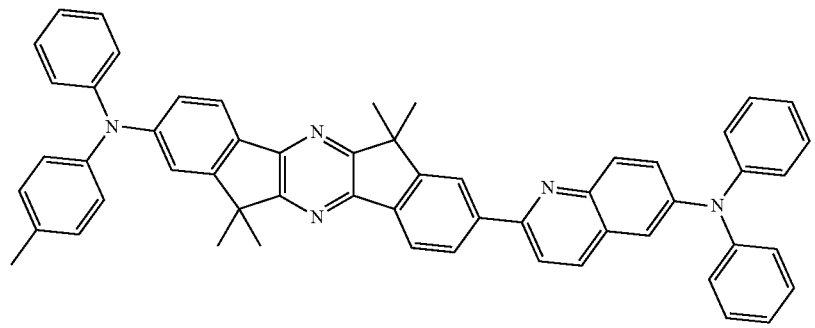

28
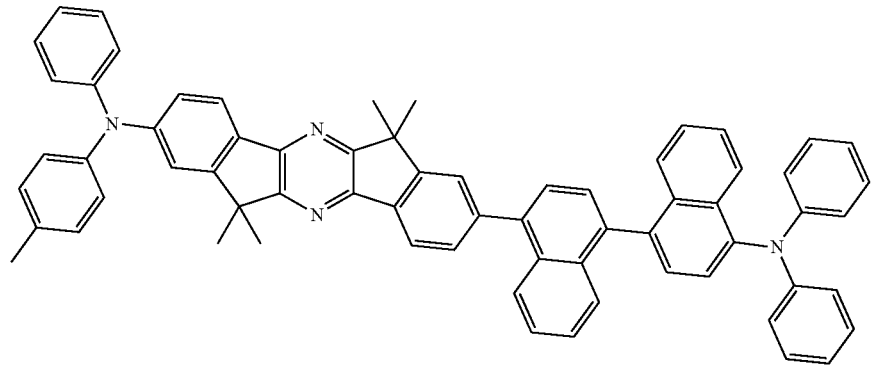
29
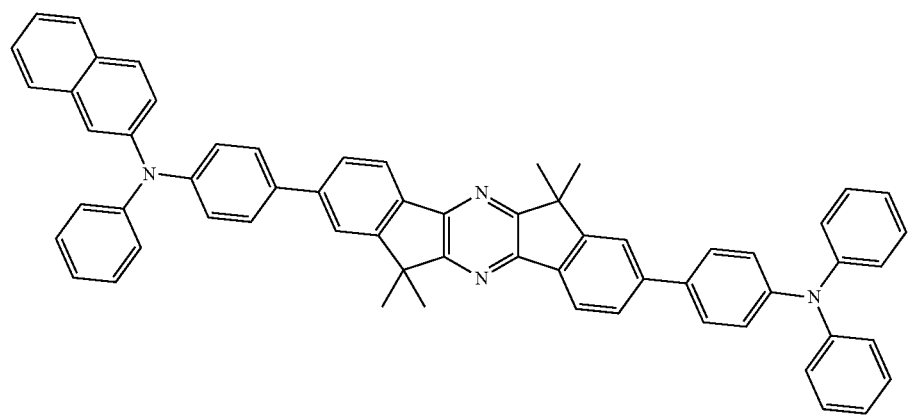
30
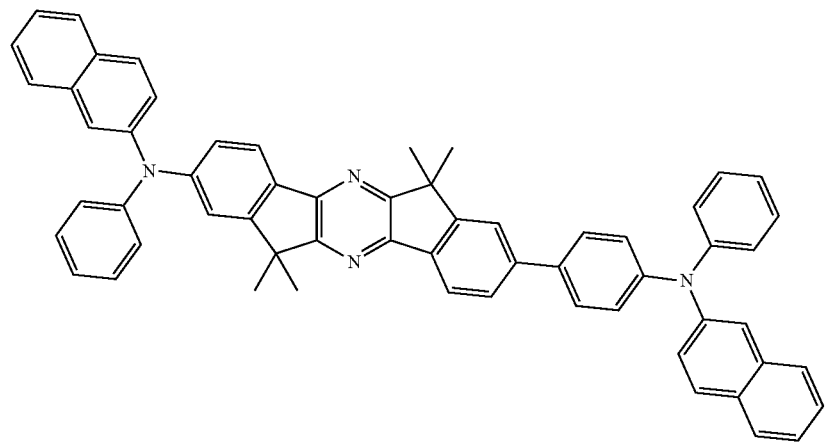
31
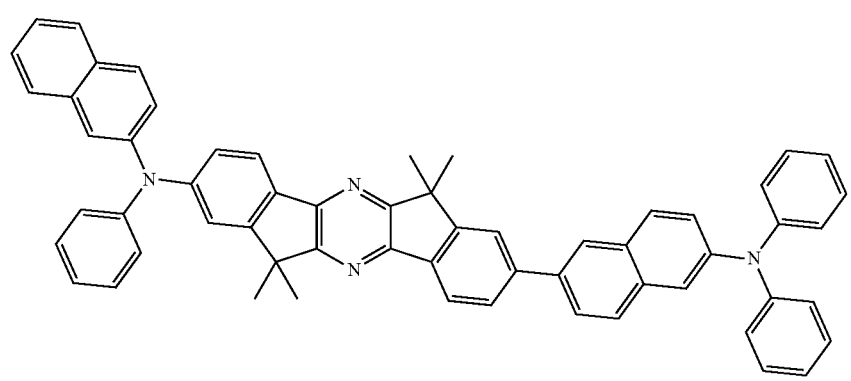

-continued
32
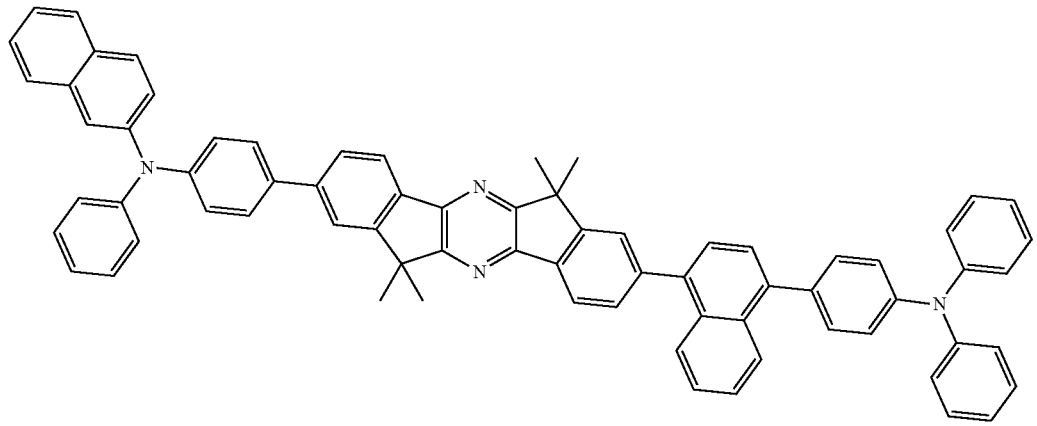
33
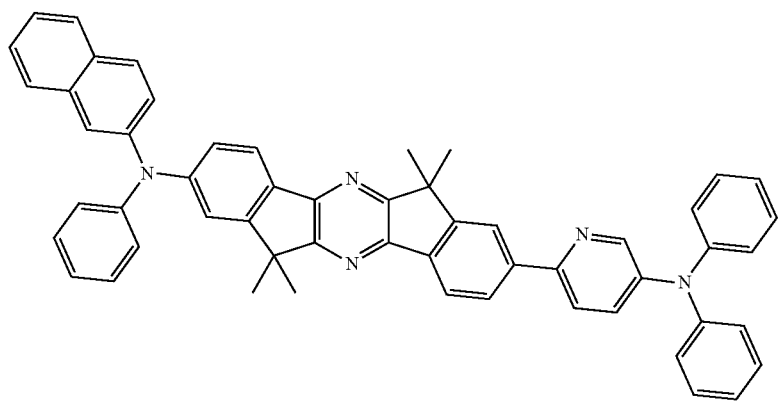
34
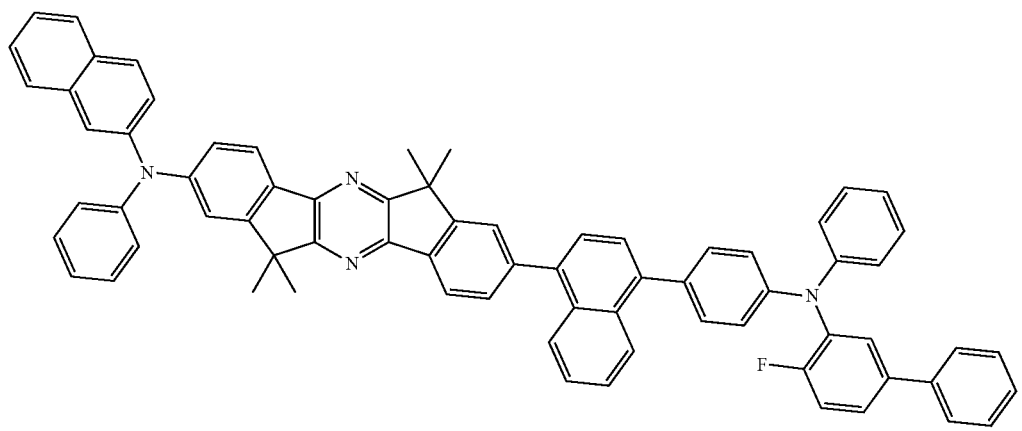
35
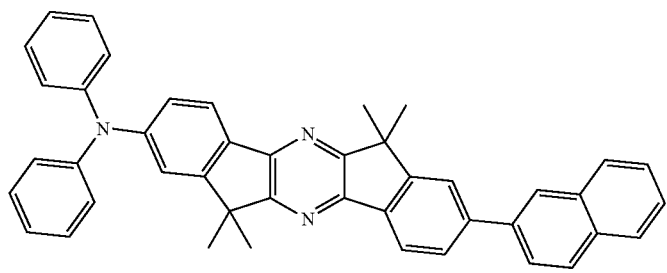

36
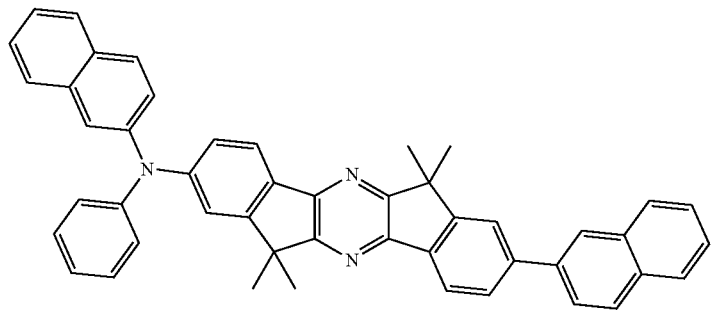
37
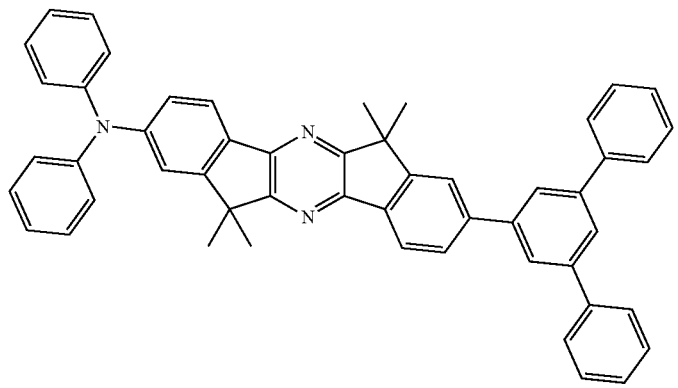
38
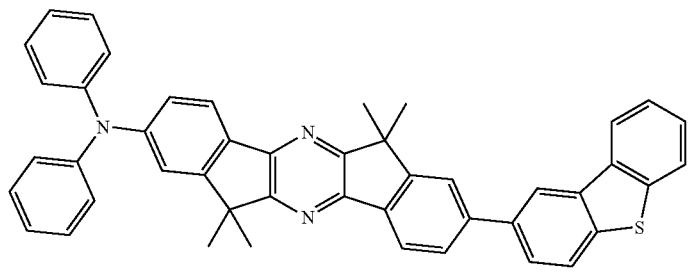
39
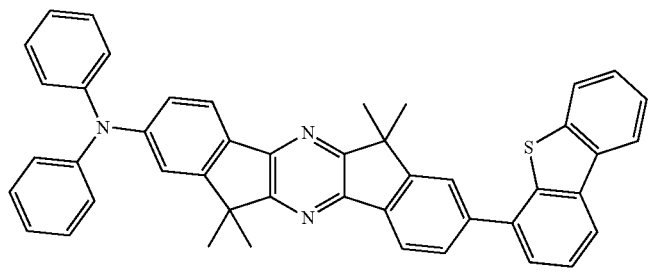
40
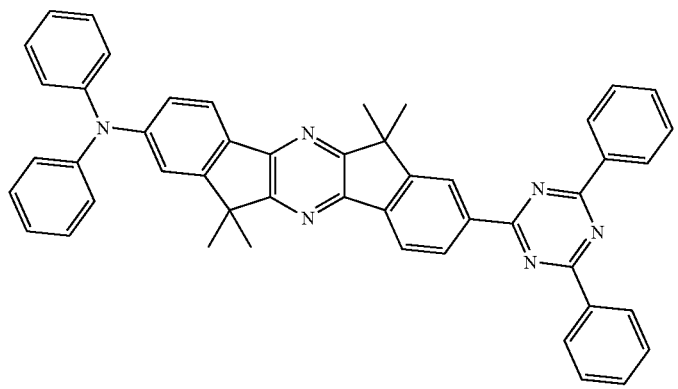

-continued
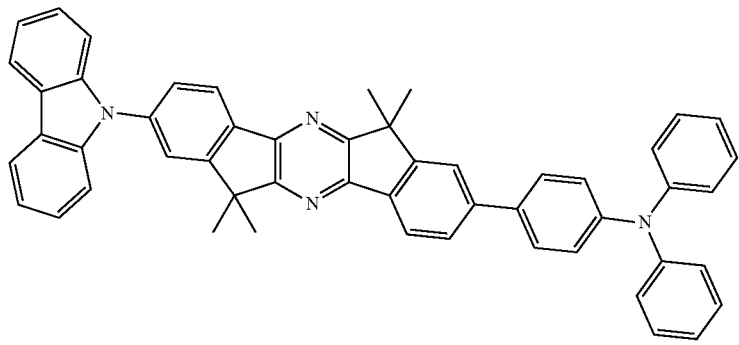
41
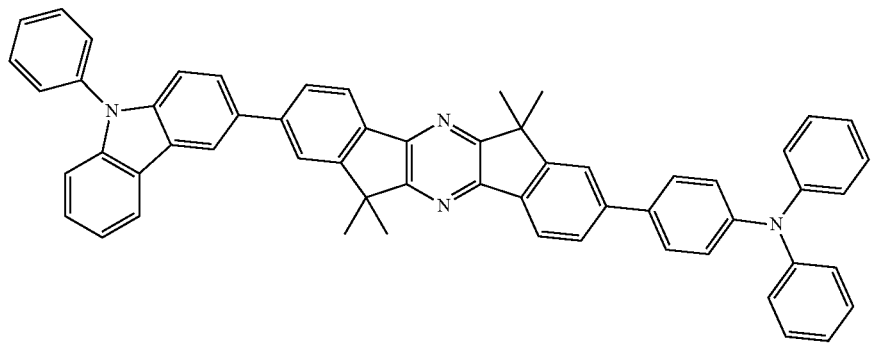
42
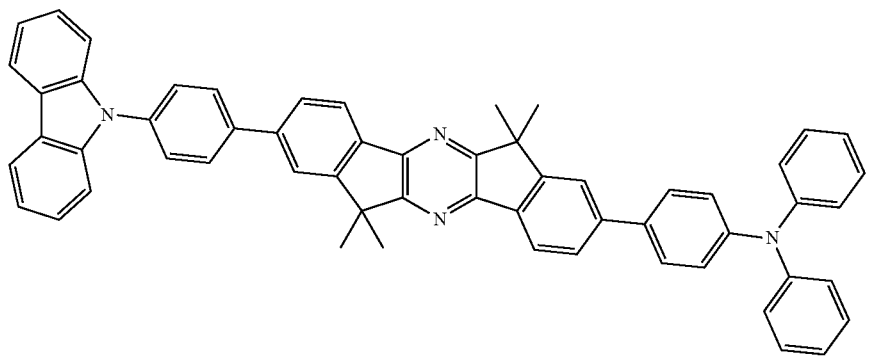
43
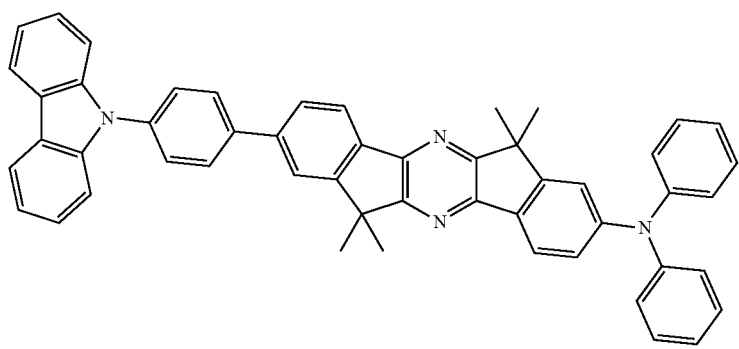
44

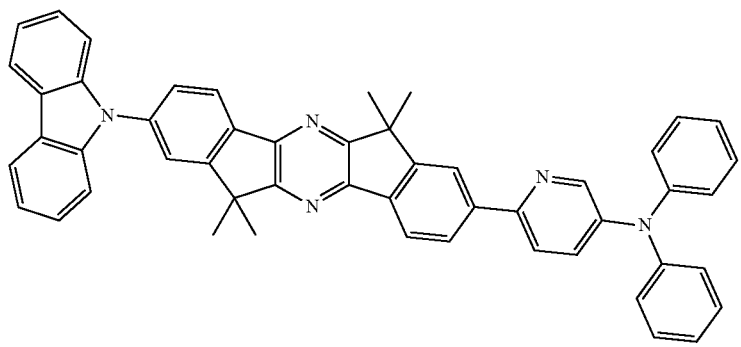
45
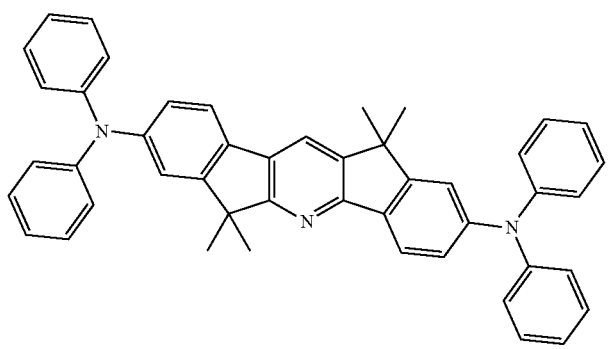
46
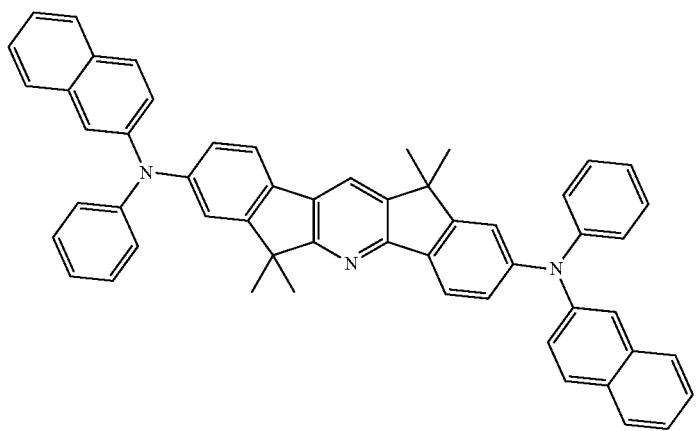
47

48
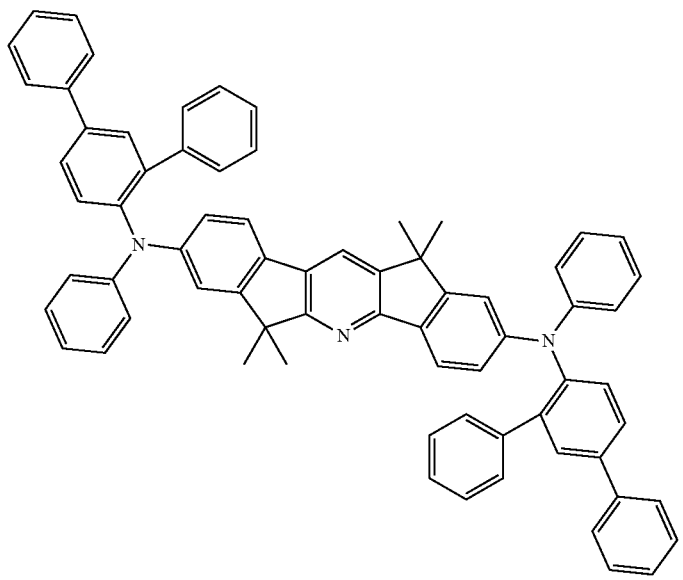
49
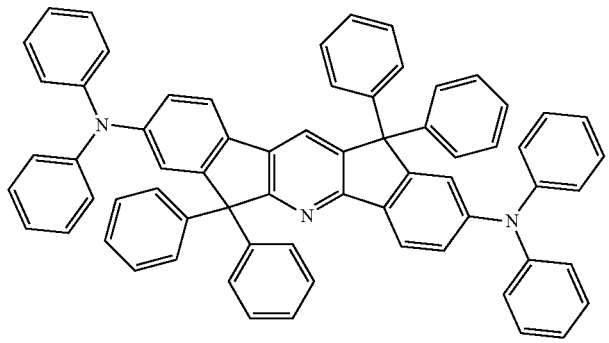
50
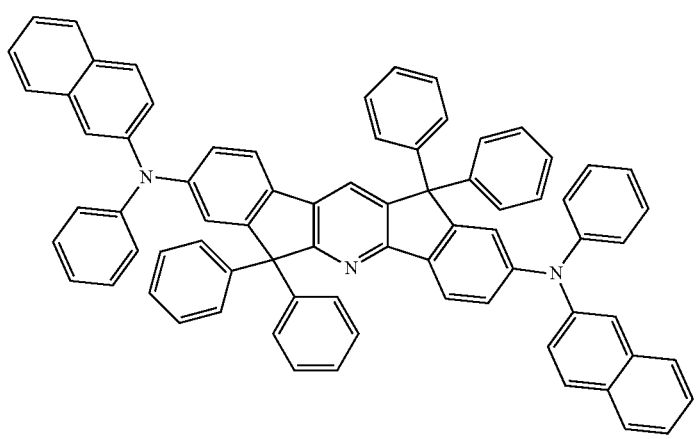

51
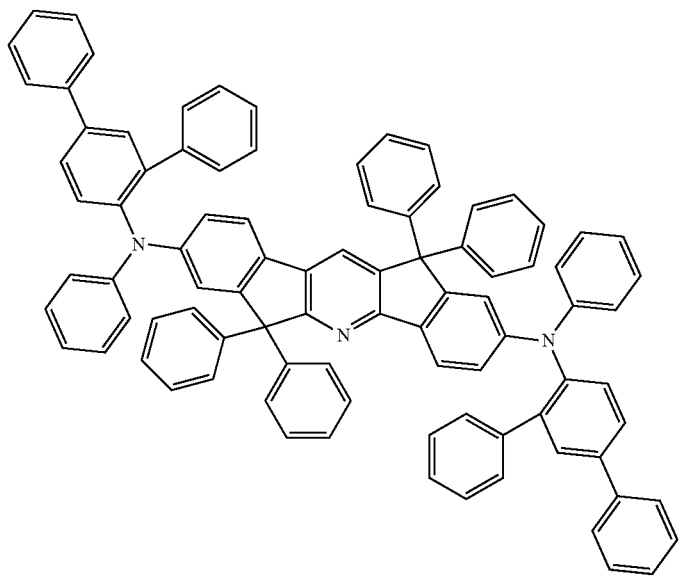
52
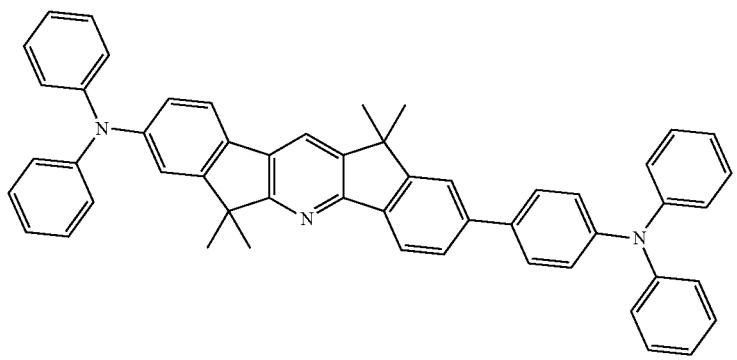
53
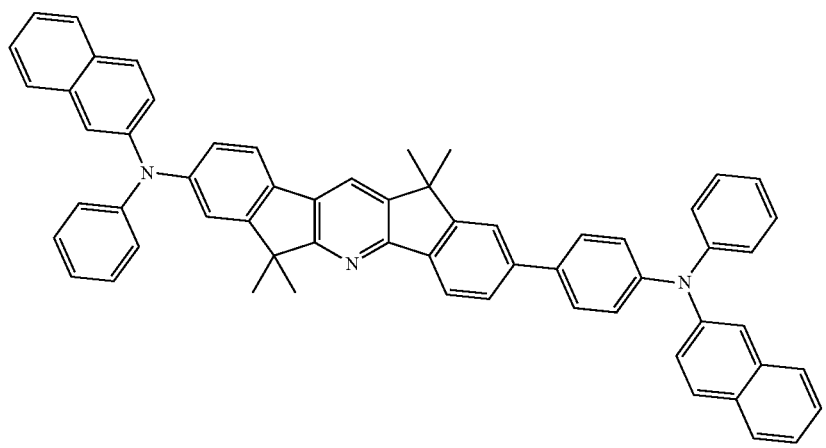

-continued
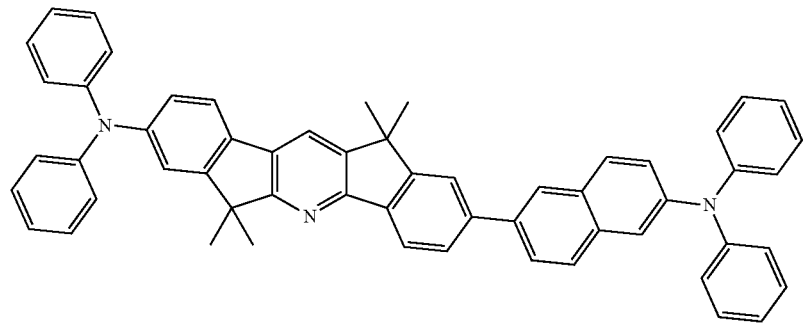
54
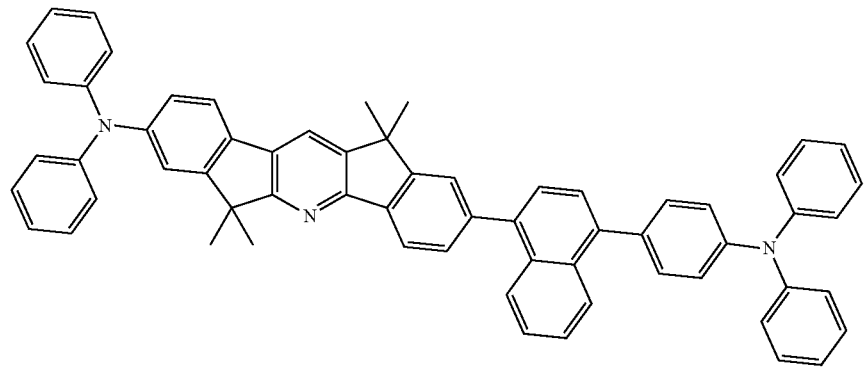
55
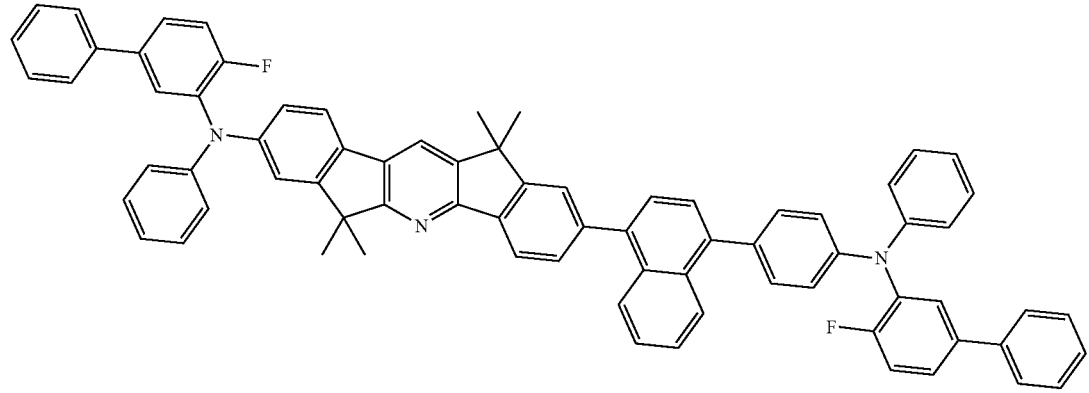
56
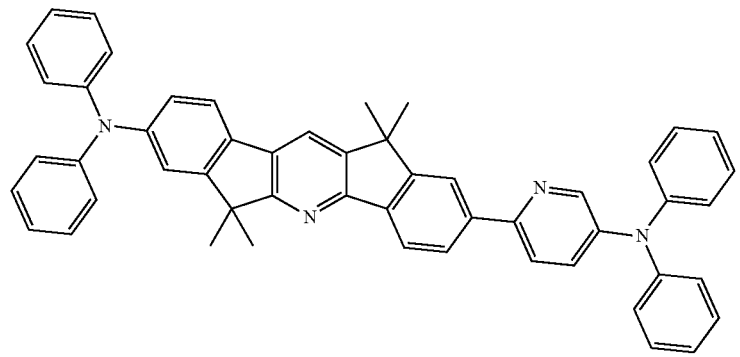
57

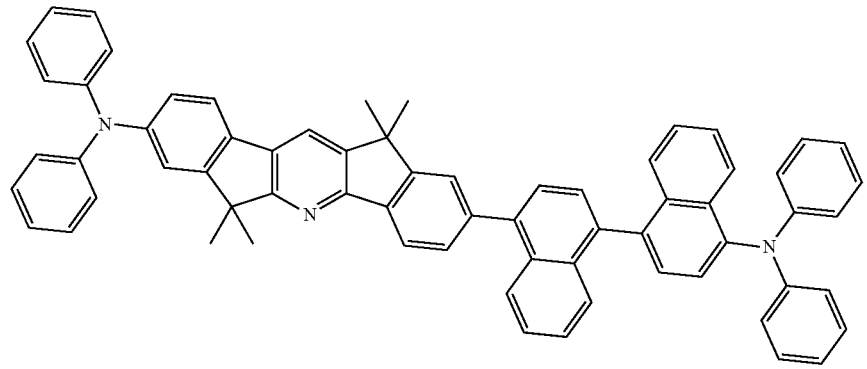
58
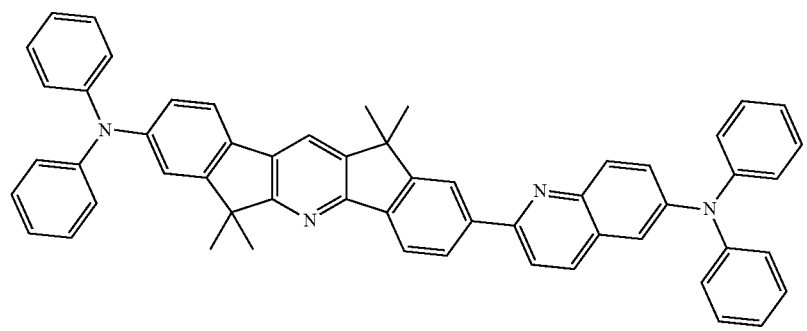
59
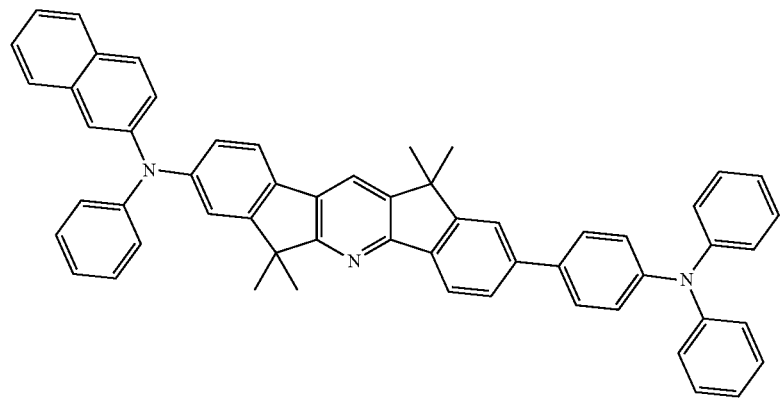
60
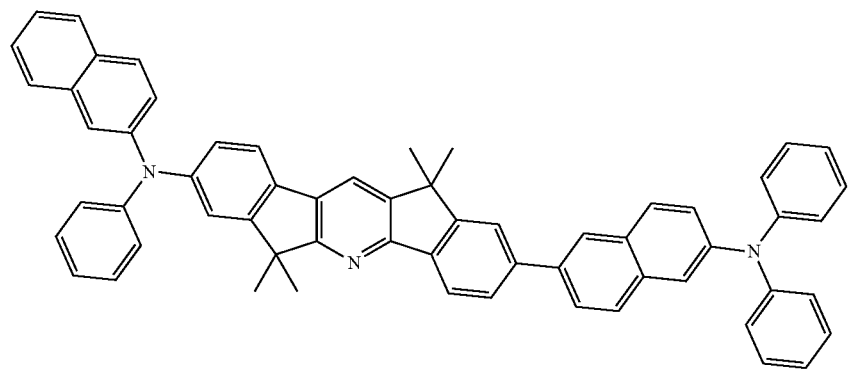
61

-continued
62
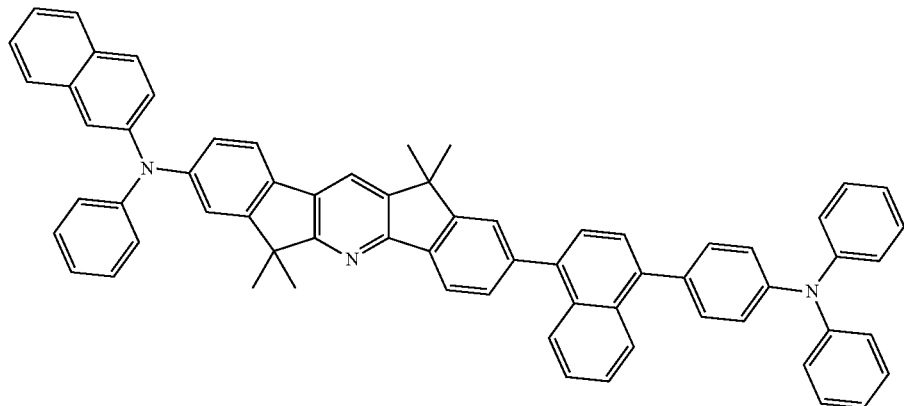
63
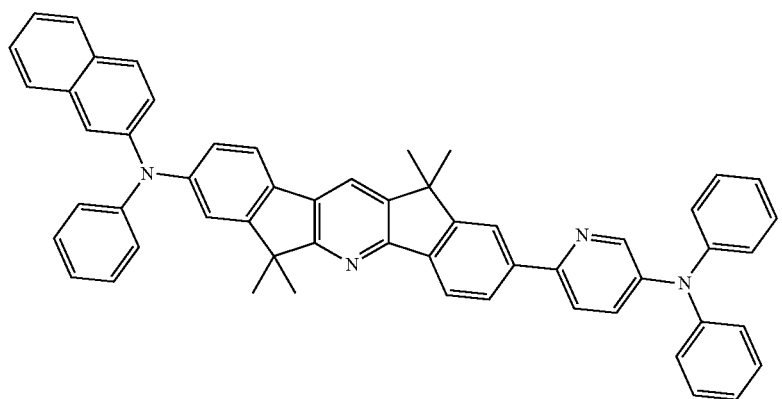
64
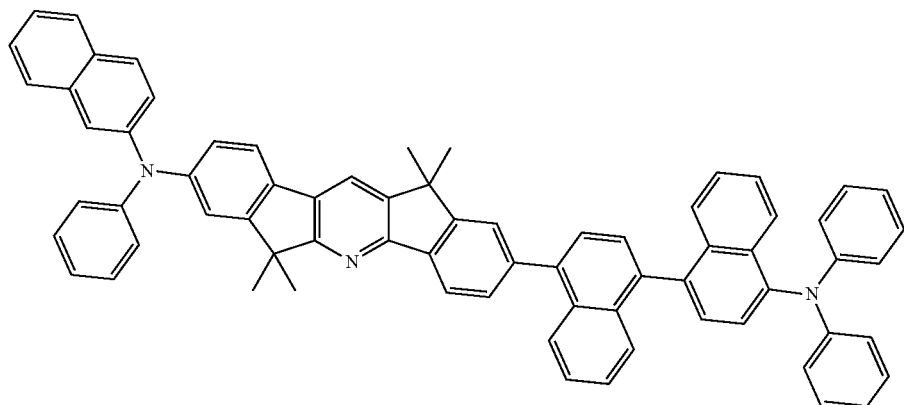
65
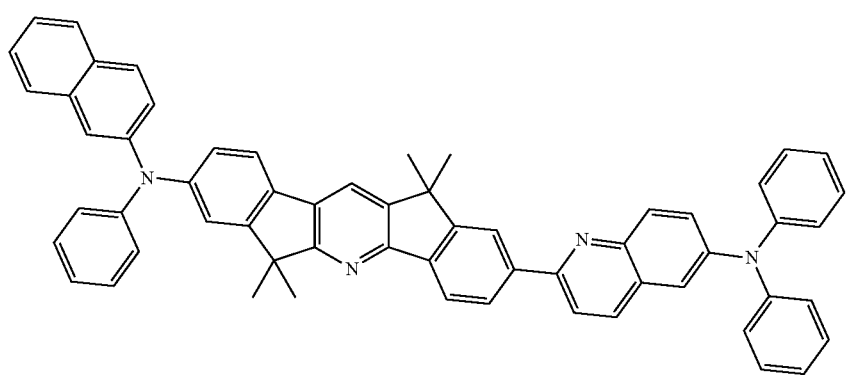

66
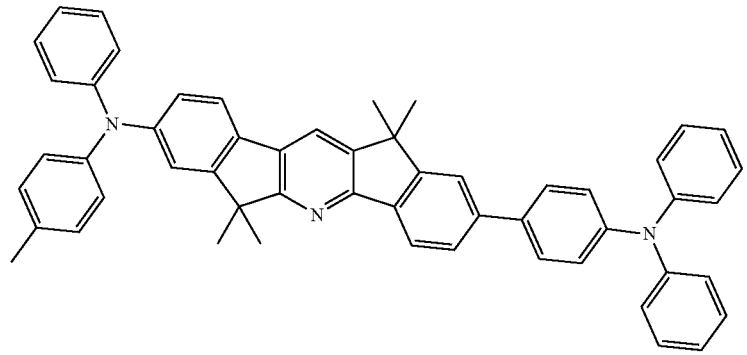
67
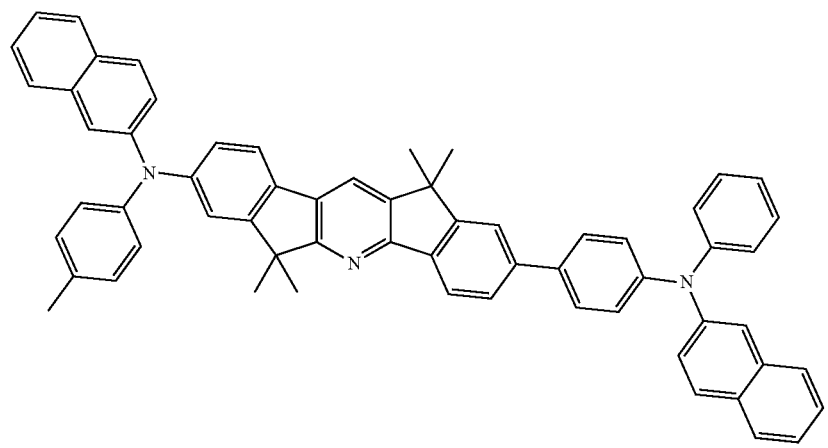
68
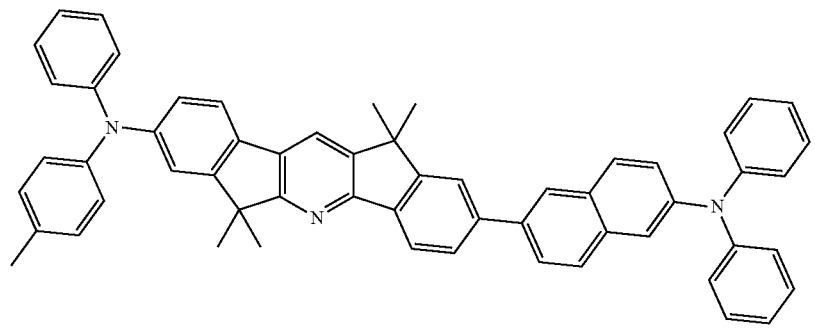
69
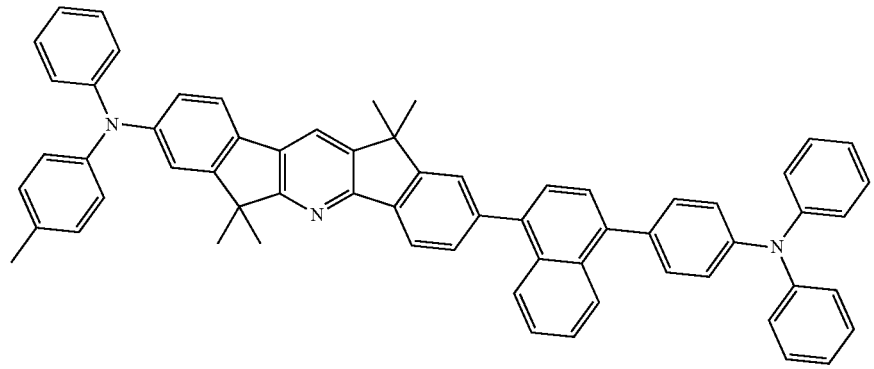

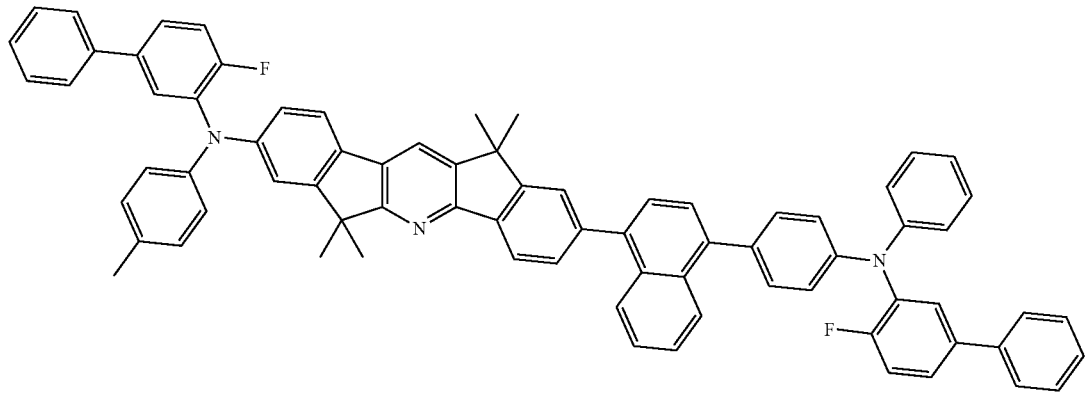
70
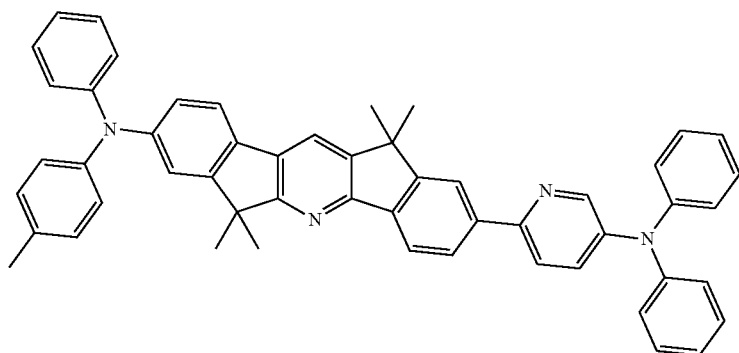
71
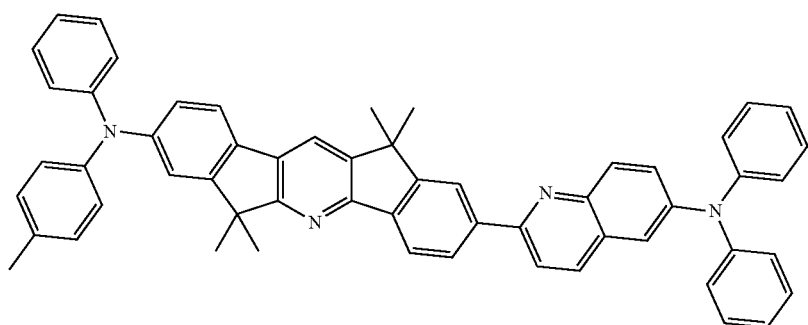
72
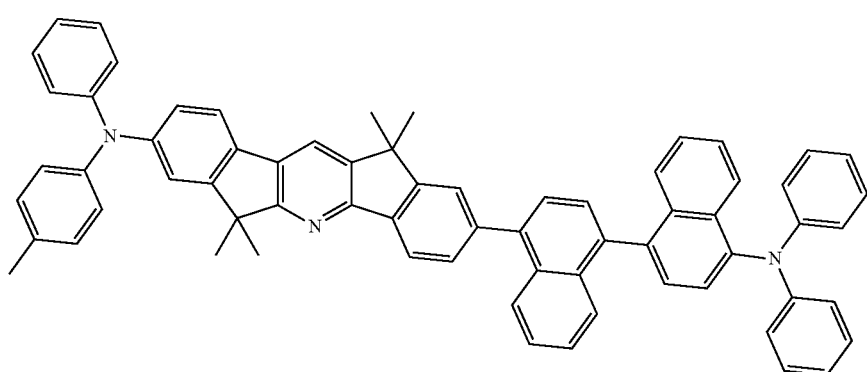
73

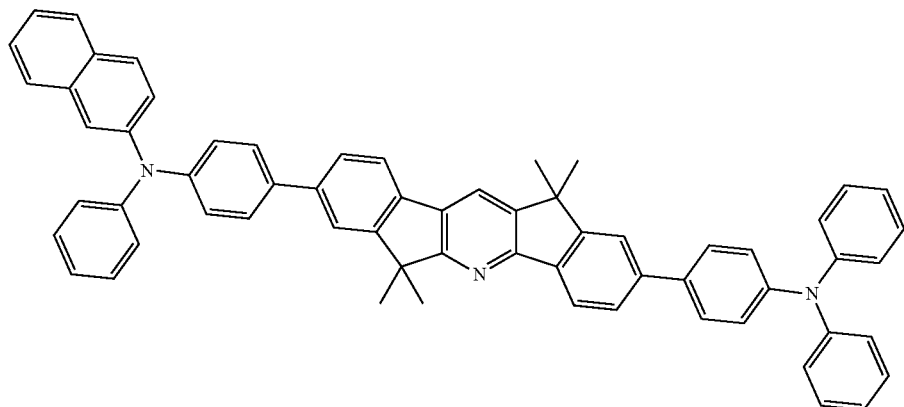
74
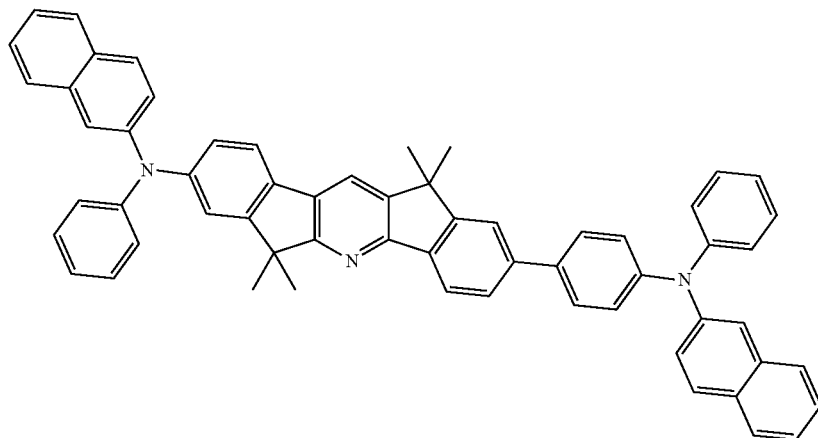
75
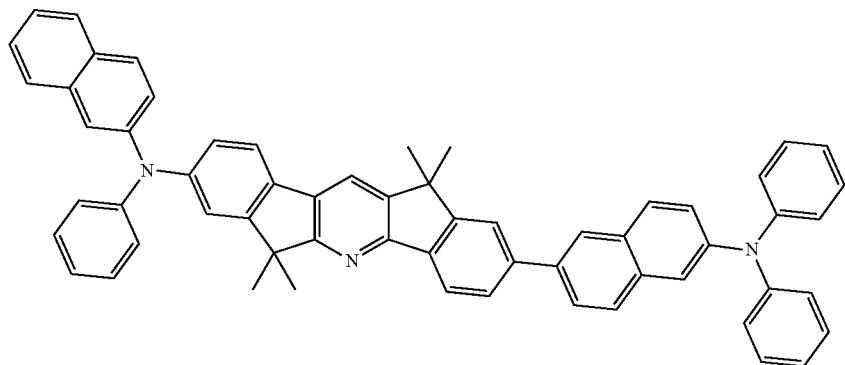
76
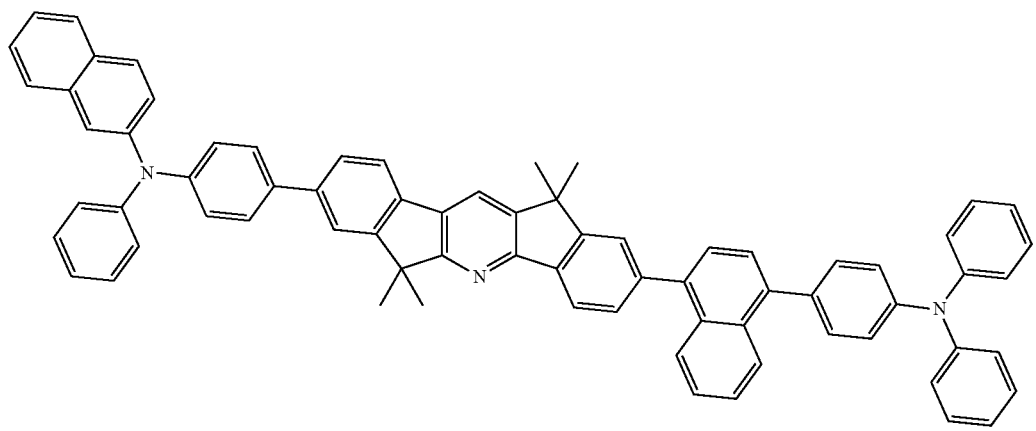
77

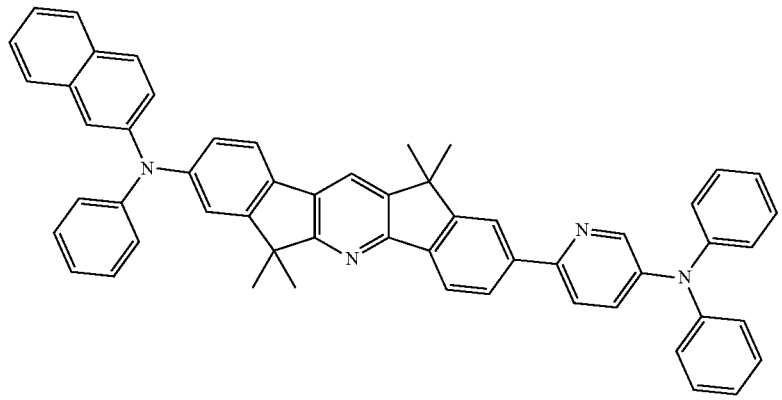
78
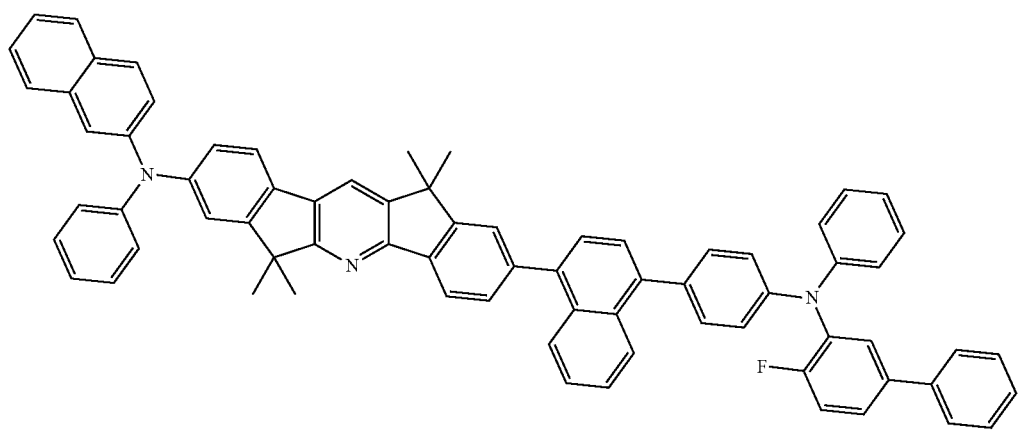
79
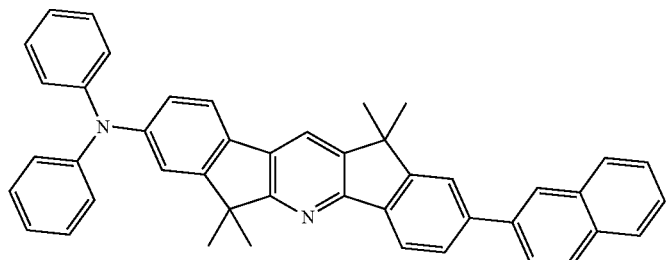
80
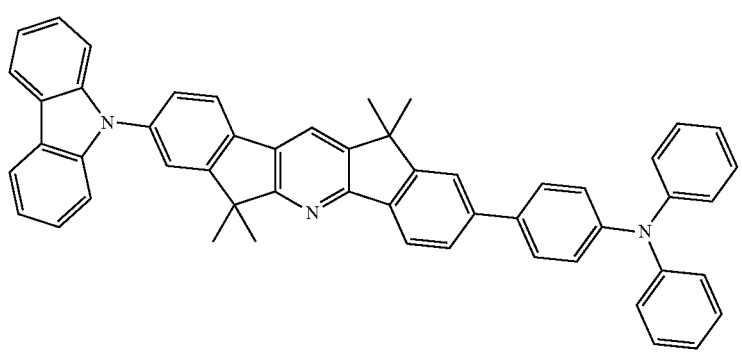
86

-continued

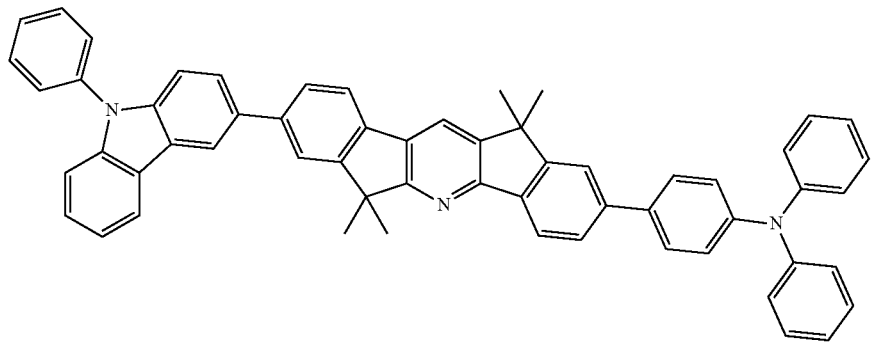

87

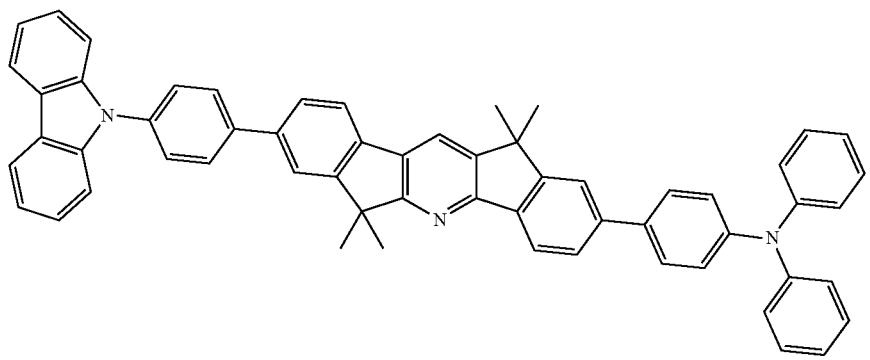

88

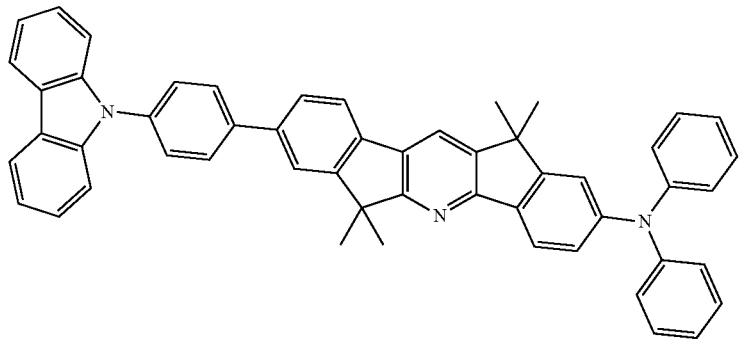

89

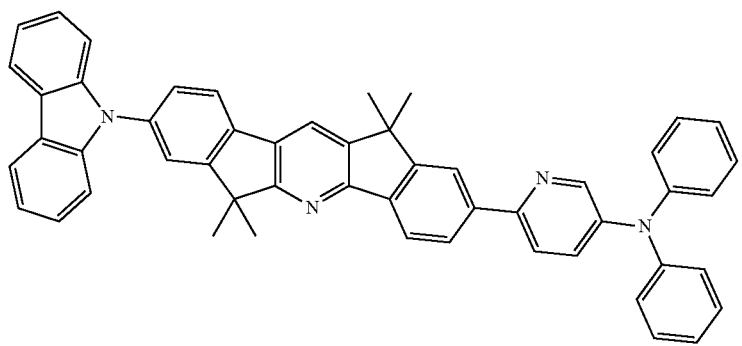

90

17. An organic light-emitting diode (OLED) comprising: a substrate; a first electrode; a second electrode facing the first electrode; and an organic layer interposed between the first electrode and the second electrode and comprising an emission layer, wherein the organic layer includes the compound of claim 1.

18. The OLED of claim 17, wherein the organic layer comprises a hole transportation region that is disposed between the first electrode and the emission layer and that comprises at least one of a hole injection layer (HIL), a hole transportation layer (HTL), a functional layer having a hole injection capability and a hole transport capability, a buffer layer, and an electron blocking layer (EBL), and an electron transportation region that is disposed between the emission layer and the second electrode and that comprises at least one of a hole blocking layer (HBL), an electron transportation layer (ETL), and an electron injection layer (EIL).

19. The OLED of claim 17, wherein the compound exists in the emission layer.
20. The OLED of claim 19, wherein the emission layer further comprises a host, and the compound acts as a dopant.
21. The heteroaryl-based compound of claim 15, wherein the heteroaryl-based compound is one of Compounds 35 to 40, 44, 80 to 85 and 89 below:
35
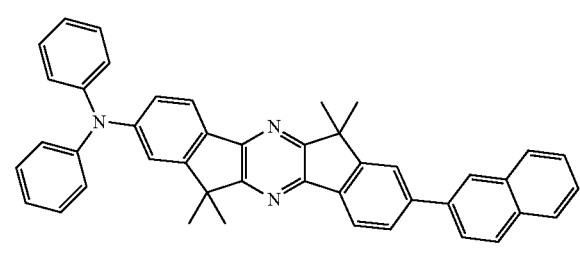
36
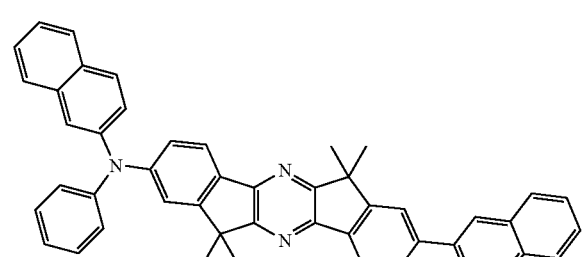
37
38
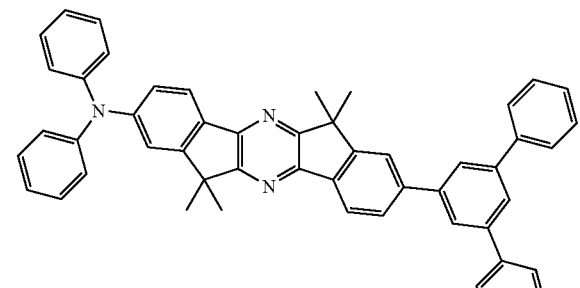
39
-continued
40
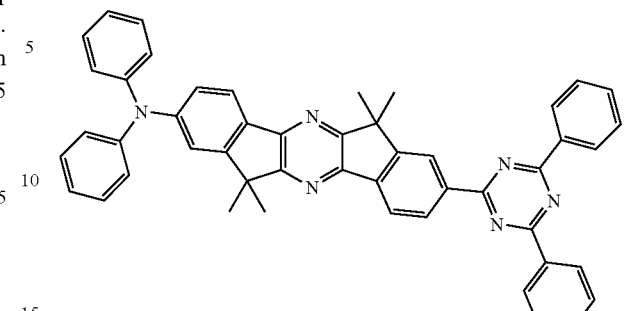
44
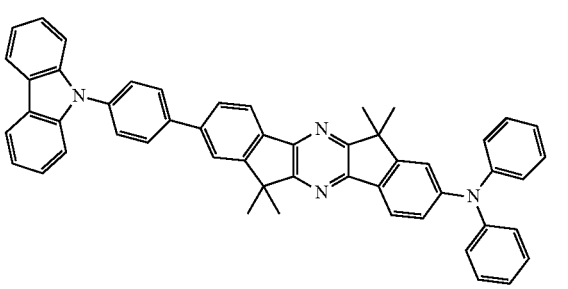
80
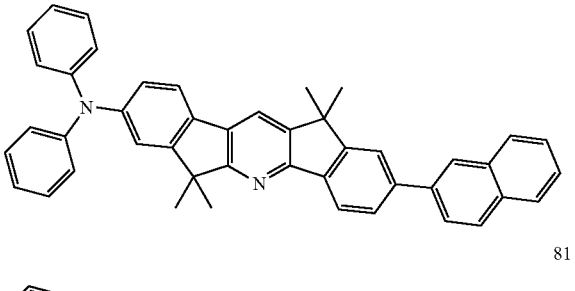
81
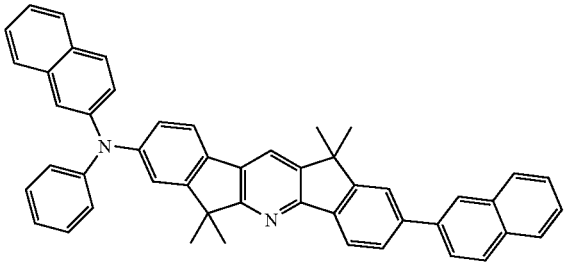
82
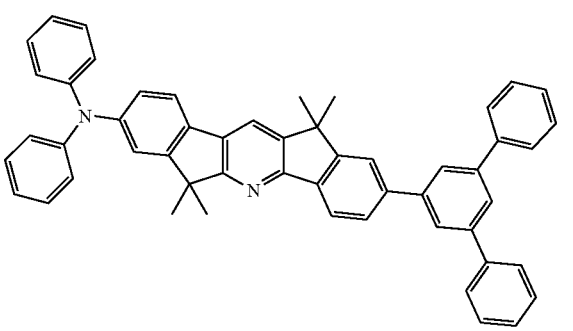

-continued
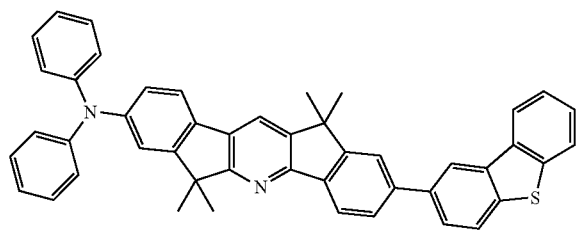
83
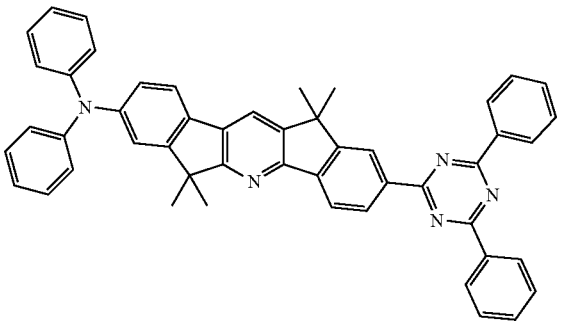
85
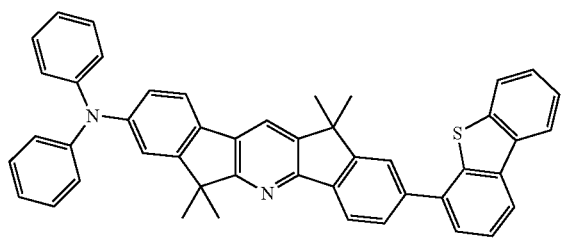
84
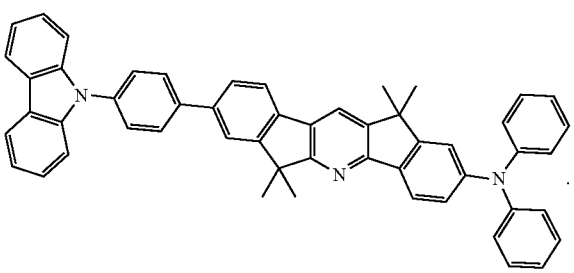
89
* * * * *